United States Patent
Lee et al.

(10) Patent No.: US 9,806,271 B2
(45) Date of Patent: Oct. 31, 2017

(54) ORGANIC ELECTROLUMINESCENT COMPOUND AND ORGANIC ELECTROLUMINESCENT DEVICE COMPRISING THE SAME

(71) Applicant: Rohm and Haas Electronic Materials Korea Ltd., Cheonan (KR)

(72) Inventors: Mi-Ja Lee, Cheonan (KR); Bitnari Kim, Cheonan (KR); Nam-Kyun Kim, Yongin (KR); Hee-Ryong Kang, Seoul (KR)

(73) Assignee: ROHM AND HAAS ELECTRONIC MATERIALS KOREA LTD., Cheonan (KR)

( * ) Notice: Subject to any disclaimer, the term of this patent is extended or adjusted under 35 U.S.C. 154(b) by 0 days.

(21) Appl. No.: 15/325,140

(22) PCT Filed: Jul. 10, 2015

(86) PCT No.: PCT/KR2015/007175
§ 371 (c)(1),
(2) Date: Jan. 10, 2017

(87) PCT Pub. No.: WO2016/006959
PCT Pub. Date: Jan. 14, 2016

(65) Prior Publication Data
US 2017/0162797 A1 Jun. 8, 2017

(30) Foreign Application Priority Data

Jul. 10, 2014 (KR) .................. 10-2014-0086690
Jul. 8, 2015 (KR) .................. 10-2015-0096899

(51) Int. Cl.
C07D 487/04 (2006.01)
H01L 51/00 (2006.01)
C09K 11/02 (2006.01)
H01L 51/50 (2006.01)

(52) U.S. Cl.
CPC ........ *H01L 51/0072* (2013.01); *C07D 487/04* (2013.01); *C09K 11/025* (2013.01); *H01L 51/5016* (2013.01)

(58) Field of Classification Search
CPC .................. H01L 51/0072; H01L 51/5016
See application file for complete search history.

(56) References Cited

U.S. PATENT DOCUMENTS

| 2014/0114069 | A1* | 4/2014 | Kim | .................. C09K 11/06 544/229 |
| 2014/0117331 | A1* | 5/2014 | Kim | .................. H01L 51/0067 257/40 |
| 2015/0357583 | A1* | 12/2015 | Ahn | .................. C07D 405/14 257/40 |
| 2016/0225992 | A1* | 8/2016 | Ito | .................. H01L 51/0072 |
| 2017/0047527 | A1* | 2/2017 | Lee | .................. H01L 51/0065 |
| 2017/0047528 | A1* | 2/2017 | Kang | .................. C09K 11/025 |
| 2017/0062730 | A1* | 3/2017 | Ahn | .................. C09K 11/06 |
| 2017/0077423 | A1* | 3/2017 | Ahn | .................. H01L 51/0072 |

FOREIGN PATENT DOCUMENTS

| KR | 20100007780 A | 1/2010 |
| KR | 20130059265 A | 6/2013 |
| KR | 20140120090 A | 10/2014 |

OTHER PUBLICATIONS

CAS Abstract of B.G. Shin et al., KR 2014120090 (2014).*
Machine Translation of B.G. Shin et al., KR 2014120090 (2014).*

* cited by examiner

*Primary Examiner* — Alexander R Pagano
(74) *Attorney, Agent, or Firm* — Jae-Choon You; Zhiqiang Zhao

(57) ABSTRACT

The present disclosure relates to an organic electroluminescent compound of Formula 1 (variables $Y_1$, $Y_2$ and $R_1$ to $R_4$ defined herein), and an organic electroluminescent device comprising the same. The organic electroluminescent compound according to the present disclosure can be used for the manufacture of an organic electroluminescent device showing improvement in luminous efficiency, especially in current efficiency.

Formula 1

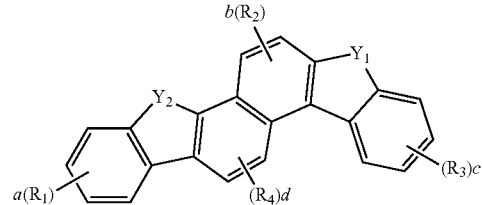

8 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent (EL) device is a self-light-emitting device which has advantages in that it provides a wider viewing angle, a greater contrast ratio, and a faster response time. An organic EL device was first developed by Eastman Kodak, by using small aromatic diamine molecules and aluminum complexes as materials to form a light-emitting layer [Appl. Phys. Lett. 51, 913, 1987].

The most important factor determining luminous efficiency in the organic EL device is light-emitting materials. Until now, fluorescent materials have been widely used as light-emitting material. However, in view of electroluminescent mechanisms, since phosphorescent materials theoretically enhance luminous efficiency by four (4) times compared to fluorescent materials, phosphorescent light-emitting materials have been widely researched. Iridium(III) complexes have been widely known as phosphorescent materials, including bis(2-(2'-benzothienyl)-pyridinato-N,C-3')iridium(acetylacetonate) ((acac)Ir(btp)$_2$), tris(2-phenylpyridine)iridium (Ir(ppy)$_3$) and bis(4,6-difluorophenylpyridinato-N,C2)picolinate iridium (Firpic) as red-, green-, and blue-emitting materials, respectively.

At present, 4,4'-N,N'-dicarbazol-biphenyl (CBP) is the most widely known host material for phosphorescent materials. Recently, Pioneer (Japan) et al., developed a high performance organic EL device using bathocuproine (BCP) and aluminum(III) bis(2-methyl-8-quinolinate)(4-phenylphenolate) (BAlq), etc., as host materials, which were known as hole blocking materials.

Although these materials provide good luminous characteristics, they have the following disadvantages: (1) Due to their low glass transition temperature and poor thermal stability, their degradation may occur during a high-temperature deposition process in a vacuum. (2) The power efficiency of the organic EL device is given by [(π/voltage)× current efficiency], and the power efficiency is inversely proportional to the voltage. Although the organic EL device comprising phosphorescent host materials provides higher current efficiency (cd/A) than one comprising fluorescent materials, a significantly high driving voltage is necessary. Thus, there is no merit in terms of power efficiency (lm/W). (3) Furthermore, the operational lifespan of the organic EL device is short, and luminous efficiency is still required to be improved.

Korean Patent Application Laying-open No. 10-2013-0059265 discloses a compound for an organic electroluminescent device, having a backbone in which a benzene ring of carbazole is fused with benzothiophene or benzofuran. However, it fails to disclose a compound having a backbone in which a benzene ring of carbazole is fused with dibenzothiophene, dibenzofuran, fluorene, or a benzene ring of another carbazole.

DISCLOSURE OF THE INVENTION

Problems to be Solved

The objective of the present disclosure is to provide an organic electroluminescent compound, which can provide an organic electroluminescent device showing high luminous efficiency, and an organic electroluminescent device comprising the same.

Solution to Problems

The present inventors found that the above objective can be achieved by an organic electroluminescent compound represented by the following formula 1.

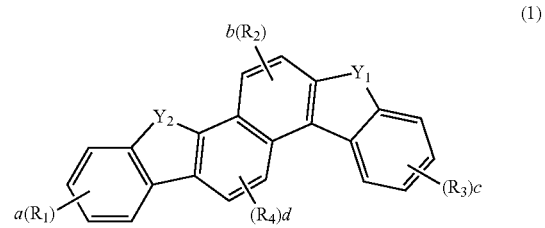

wherein $Y_1$ and $Y_2$, each independently, represent $NR_{11}$, $CR_{12}R_{13}$, O, or S; with the proviso that at least one of $Y_1$ and $Y_2$ represents $NR_{11}$;

$R_{11}$ represents *-$L_1$-Ar;

* represents a bonding site;

$L_1$ represents a single bond, a substituted or unsubstituted (C6-C30)arylene, or a substituted or unsubstituted 5- to 30-membered heteroarylene;

Ar represents a substituted or unsubstituted (C6-C30)aryl, or a substituted or unsubstituted 5- to 30-membered heteroaryl;

$R_{12}$ and $R_{13}$, each independently, represent a substituted or unsubstituted (C1-C30)alkyl, a substituted or unsubstituted (C6-C30)aryl, or a substituted or unsubstituted 5- to 30-membered heteroaryl; or may be linked to an adjacent substituent(s) to form a substituted or unsubstituted, (C3-C30), mono- or polycyclic, alicyclic or aromatic ring, whose carbon atom(s) may be replaced with at least one hetero atom selected from nitrogen, oxygen, and sulfur;

$R_1$ and $R_3$, each independently, represent hydrogen, deuterium, a halogen, a cyano, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted 3- to 7-membered heterocycloalkyl, a substituted or unsubstituted (C1-C30)alkoxy, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent(s) to form a substituted or unsubstituted, (C3-C30), mono- or polycyclic, alicyclic or aromatic ring, whose carbon atom(s) may be replaced with at least one hetero atom selected from nitrogen, oxygen, and sulfur;

$R_2$ and $R_4$, each independently, represent hydrogen, deuterium, a halogen, a cyano, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted 3- to 7-membered heterocycloalkyl, a substituted or unsubstituted (C1-C30)alkoxy, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

a and c, each independently, represent an integer of 1 to 4; where a or c is an integer of 2 or more, each of $R_1$ or $R_3$ may be the same or different;

b and d, each independently, represent an integer of 1 to 2; where b or d is an integer of 2 or more, each of $R_2$ or $R_4$ may be the same or different; and the heteroaryl(ene) and heterocycloalkyl, each independently, contain at least one hetero atom selected from B, N, O, S, Si, and P.

Effects of the Invention

The organic electroluminescent compound of the present disclosure can provide an organic electroluminescent device showing excellence in luminous efficiency, especially in current efficiency.

EMBODIMENTS OF THE INVENTION

Hereinafter, the present disclosure will be described in detail. However, the following description is intended to explain the invention, and is not meant in any way to restrict the scope of the invention.

The present disclosure provides the organic electroluminescent compound represented by formula 1 above, an organic electroluminescent material comprising the organic electroluminescent compound, and an organic electroluminescent device comprising the compound.

The details of the organic electroluminescent compound of formula 1 are as follows.

Herein, "alkyl" includes methyl, ethyl, n-propyl, isopropyl, n-butyl, isobutyl, tert-butyl, etc. "Alkenyl" includes vinyl, 1-propenyl, 2-propenyl, 1-butenyl, 2-butenyl, 3-butenyl, 2-methylbut-2-enyl, etc. "Alkynyl" includes ethynyl, 1-propynyl, 2-propynyl, 1-butynyl, 2-butynyl, 3-butynyl, 1-methylpent-2-ynyl, etc. "Cycloalkyl" includes cyclopropyl, cyclobutyl, cyclopentyl, cyclohexyl, etc. "(3- to 7-membered)heterocycloalkyl" indicates a cycloalkyl having 3 to 7 ring backbone atoms including at least one hetero atom selected from B, N, O, S, Si, and P, preferably O, S, and N, and includes tetrahydrofuran, pyrrolidine, thiolan, tetrahydropyran, etc. Furthermore, "aryl(ene)" indicates a monocyclic or fused ring radical derived from an aromatic hydrocarbon, and includes a spiro compound in which two rings are connected through one atom. The aryl includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "5- to 30-membered heteroaryl(ene)" indicates an aryl group having 5 to 30 ring backbone atoms including at least one, preferably 1 to 4, hetero atom selected from the group consisting of B, N, O, S, Si, and P; may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidyl, pyridazinyl, etc., and a fused ring-type heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, naphthylidinyl, cinnolinyl, quinazolinyl, quinoxalinyl, carbazolyl, phenoxazinyl, phenanthridinyl, benzodioxolyl, dihydroacridinyl, etc. Furthermore, "halogen" includes F, Cl, Br, and I.

Herein, "substituted" in the expression, "substituted or unsubstituted," means that a hydrogen atom in a certain functional group is replaced with another atom or group, i.e. a substituent. In the present disclosure, the substituents for the substituted alkyl, the substituted aryl(ene), the substituted heteroaryl(ene), the substituted cycloalkyl, the substituted heterocycloalkyl, the substituted alkoxy, the substituted trialkylsilyl, the substituted triarylsilyl, the substituted dialkylarylsilyl, the substituted alkyldiarylsilyl, the substituted mono- or di-alkylamino, the substituted mono- or di-arylamino, the substituted alkylarylamino, and the substituted mono- or polycyclic, alicyclic or aromatic ring in $L_1$, $L_{1a}$, $L_{1b}$, $L_4$, M, Ar, $Ar_a$, $Ar_b$, $R_1$ to $R_4$, $R_{12}$, $R_{13}$, $R_{31}$ to $R_{37}$, $R_{41}$ to $R_{43}$, $R_{100}$ to $R_{109}$, $R_{111}$ to $R_{127}$ and $R_{201}$ to $R_{211}$, each independently, may be at least one selected from the group consisting of deuterium, a halogen, a cyano, a carboxy, a nitro, a hydroxy, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 3- to 30-membered heteroaryl unsubstituted or substituted with a (C6-C30)aryl, a (C6-C30)aryl unsubstituted or substituted with a 3- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

In formula 1, preferably, at least one of $Y_1$ and $Y_2$ may represent $NR_1$ in which $L_1$ represents a single bond or a substituted or unsubstituted (C6-C21)arylene and Ar represents a substituted or unsubstituted 5- to 30-membered heteroaryl. $L_1$ may be specifically, a single bond, a substituted or unsubstituted phenylene, a substituted or unsubstituted biphenylene, or a substituted or unsubstituted naphthylene. Where Ar is a substituted or unsubstituted heteroaryl, Ar may be specifically, a substituted or unsubstituted pyridyl, a substituted or unsubstituted pyrimidyl, a substituted or unsubstituted triazinyl, a substituted or unsubstituted pyrazinyl, a substituted or unsubstituted quinolyl, a substituted or unsubstituted isoquinolyl, a substituted or unsubstituted quinazolinyl, a substituted or unsubstituted quinoxalinyl, a substituted or unsubstituted naphthylidinyl, a substituted or unsubstituted carbazolyl, a substituted or unsubstituted dibenzothiophenyl, or a substituted or unsubstituted dibenzofuranyl.

Preferably, one of $Y_1$ and $Y_2$ may represent $NR_{11a}$ and the other may represent $NR_{11b}$, $CR_{12}R_{13}$, O, or S; $R_{11a}$ may represent *-$L_{1a}$-$Ar_a$; $R_{11b}$ may represent *-$L_{1b}$-$Ar_b$; $L_{1a}$ and $L_{1b}$, each independently, may represent a single bond or a substituted or unsubstituted (C6-C21)arylene; $Ar_a$ may represent a substituted or unsubstituted 5- to 30-membered heteroaryl; $Ar_b$ may represent a substituted or unsubstituted (C6-C30)aryl; and $R_{12}$ and $R_{13}$ may be as defined in formula 1 above. Specifically, $L_{1a}$ and $L_{1b}$, each independently, may represent a single bond, a substituted or unsubstituted phenylene, a substituted or unsubstituted biphenylene, or a substituted or unsubstituted naphthylene. Preferably, $Ar_a$ may represent a substituted or unsubstituted nitrogen-containing 5- to 21-membered heteroaryl. Specifically, $Ar_a$ may represent a substituted or unsubstituted pyridyl, a substituted or unsubstituted pyrimidyl, a substituted or unsubstituted triazinyl, a substituted or unsubstituted pyrazinyl, a substituted or unsubstituted quinolyl, a substituted or unsubstituted isoquinolyl, a substituted or unsubstituted quinazolinyl, a substituted or unsubstituted quinoxalinyl, a substituted or unsubstituted naphthylidinyl, a substituted or unsubstituted carbazolyl, a substituted or unsubstituted dibenzothiophenyl, or a substituted or unsubstituted dibenzofuranyl. Specifically, $Ar_b$ may represent a substituted or unsubstituted phenyl, a substituted or unsubstituted biphenyl, or a substituted or unsubstituted naphthyl.

More specifically, Ar and $Ar_a$, each independently, may be selected from the following formulae 2-1 to 2-7.

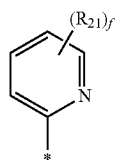
(2-1)

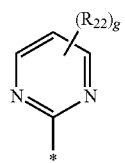
(2-2)

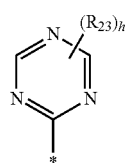
(2-3)

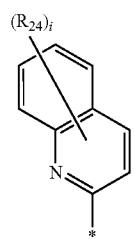
(2-4)

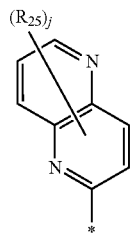
(2-5)

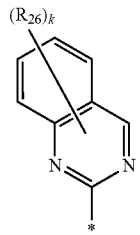
(2-6)

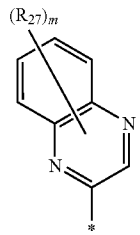
(2-7)

wherein $R_{21}$ to $R_{27}$, each independently, represent hydrogen, deuterium, a halogen, a cyano, a (C1-C30)alkyl, a (C3-C30)cycloalkyl, a (C6-C30)aryl unsubstituted or substituted with a halogen, a cyano, a (C1-C30)alkyl, a 5- to 18-membered heteroaryl, a di(C1-C30)alkyl(C6-C30)arylsilyl, a (C1-C30)alkyldi(C6-C30)arylsilyl, or a tri(C6-C30)arylsilyl, a 5- to 30-membered heteroaryl unsubstituted or substituted with a halogen, a cyano, a (C1-C30)alkyl, a (C6-C18)aryl, a di(C1-C30)alkyl(C6-C30)arylsilyl, a (C1-C30)alkyldi(C6-C30)arylsilyl, or a tri(C6-C30)arylsilyl, a di(C1-C30)alkyl(C6-C30)arylsilyl, a (C1-C30)alkyldi(C6-C30)arylsilyl, or a tri(C6-C30)arylsilyl;

f represents an integer of 1 to 4; g represents an integer of 1 to 3; h represents an integer of 1 to 2; i represents an integer of 1 to 6; j, k, and m, each independently, represent an integer of 1 to 5; where f, g, h, i, j, k, or m is an integer of 2 or more, each of $R_{21}$, $R_{22}$, $R_{23}$, $R_{24}$, $R_{25}$, $R_{26}$, or $R_{27}$ may be the same or different; and the heteroaryl contains at least one hetero atom selected from N, O, and S.

Preferably, $R_{12}$ and $R_{13}$, each independently, may represent a substituted or unsubstituted (C1-C10)alkyl, a substituted or unsubstituted (C6-C21)aryl, or a substituted or unsubstituted 5- to 21-membered heteroaryl, or may be linked to an adjacent substituent(s) to form a substituted or unsubstituted, (C3-C30), mono- or polycyclic aromatic ring. More preferably, $R_{12}$ and $R_{13}$, each independently, may represent a substituted or unsubstituted (C1-C10)alkyl or a substituted or unsubstituted (C6-C18)aryl, or may form a substituted or unsubstituted polycyclic aromatic ring with C of $CR_{12}R_{13}$. Specifically, $R_{12}$ and $R_{13}$, each independently, may represent an unsubstituted (C1-C10)alkyl or an unsubstituted phenyl, or may form a fluorene with C of $CR_{12}R_{13}$.

According to one embodiment of the present disclosure, one of $Y_1$ and $Y_2$ is $NR_{11a}$ and the other is $NR_{11b}$, $CR_{12}R_{13}$, O, or S; $R_{11a}$ represents *-$L_{1a}$-$Ar_a$; $R_{11b}$ represents *-$L_{1b}$-

Ar$_b$; L$_{1a}$ and L$_{1b}$, each independently, represent a single bond or a substituted or unsubstituted (C6-C21)arylene; Ar$_a$ represents a substituted or unsubstituted 5- to 30-membered heteroaryl; Ar$_b$ represents a substituted or unsubstituted (C6-C30)aryl; and R$_{12}$ and R$_{13}$, each independently, represent a substituted or unsubstituted (C1-C10)alkyl, a substituted or unsubstituted (C6-C21)aryl, or a substituted or unsubstituted 5- to 21-membered heteroaryl, or may be linked to an adjacent substituent(s) to form a substituted or unsubstituted, (C3-C30), mono- or polycyclic aromatic ring More specifically, the organic electroluminescent compound of the present disclosure includes the following, but is not limited thereto:

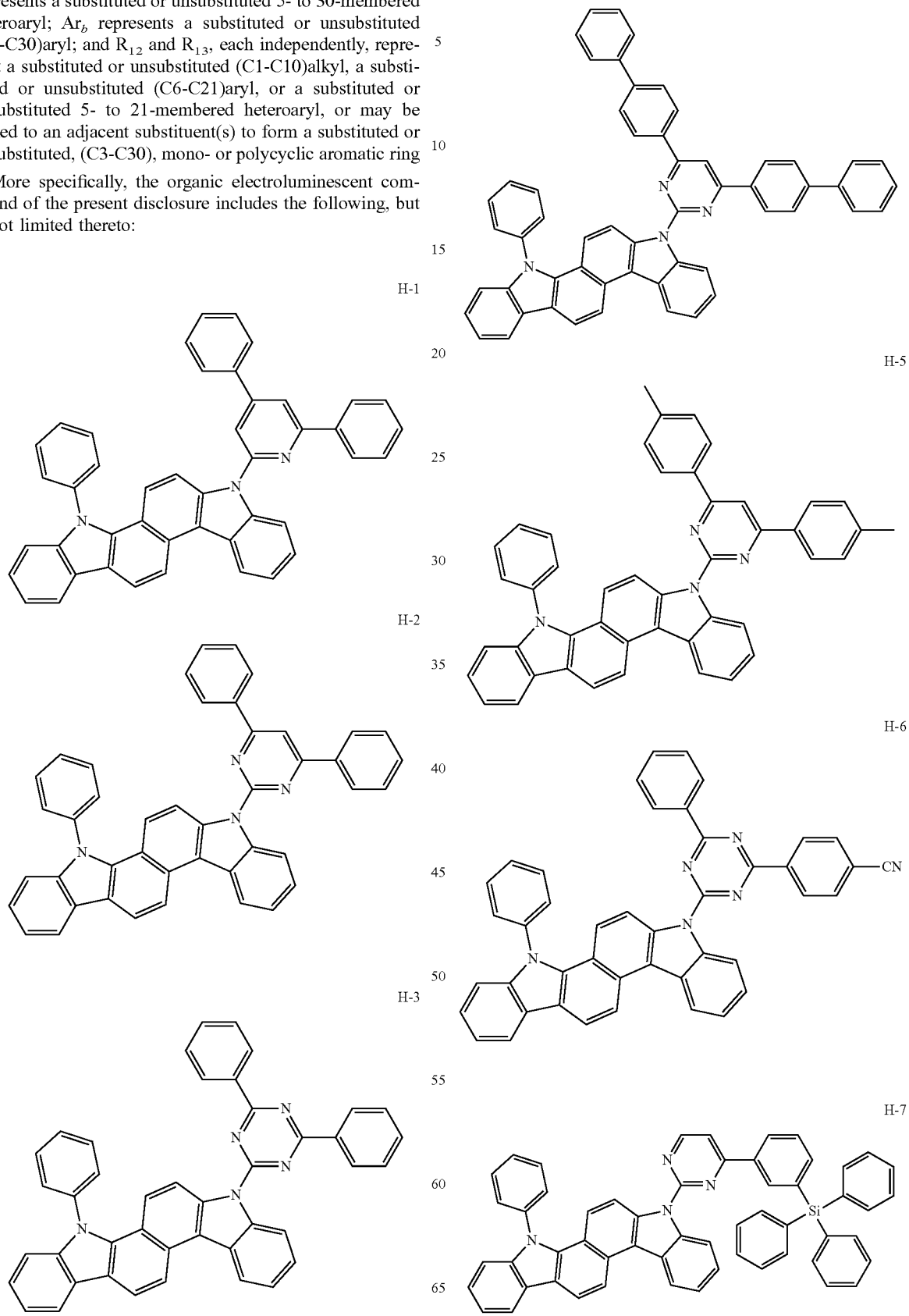

-continued
H-8
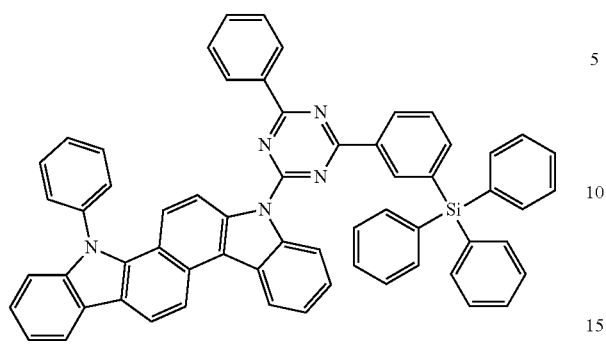
H-9
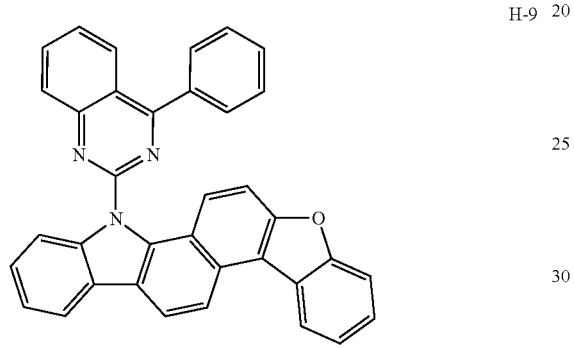
H-10
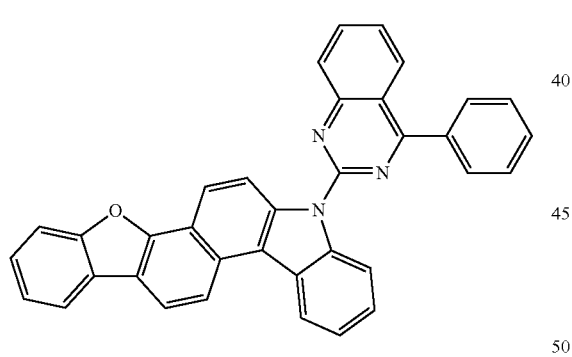
H-11
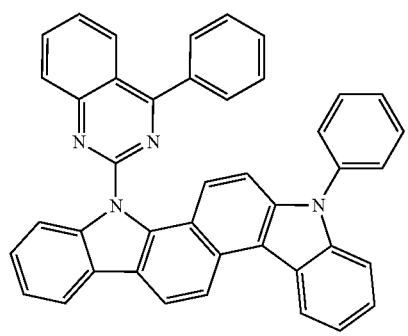
-continued
H-12
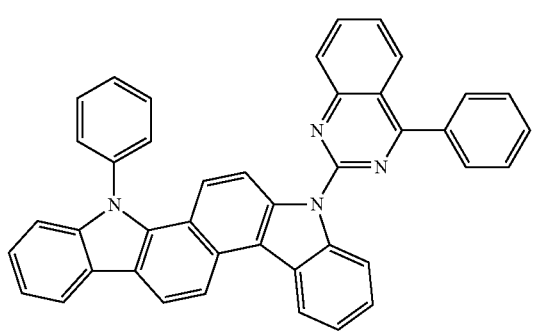
H-13
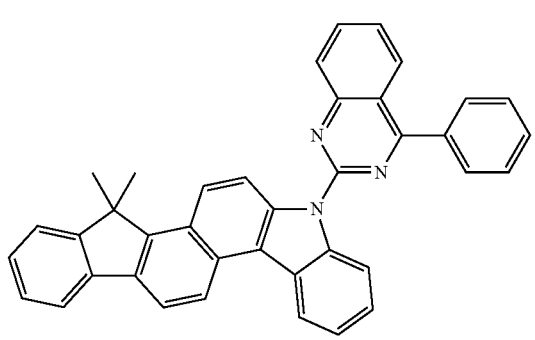
H-14
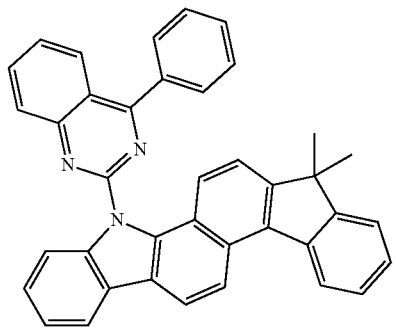
H-15
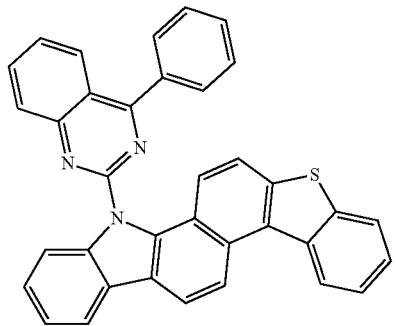

-continued
H-16
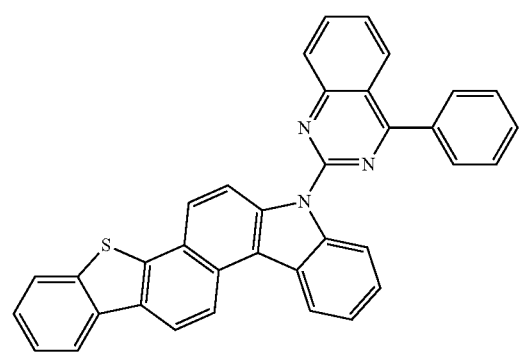
H-17
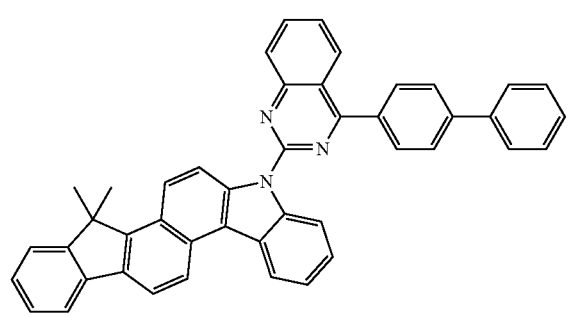
H-18
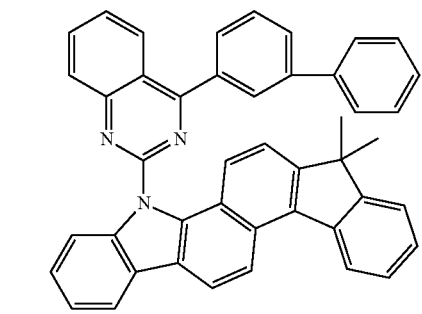
H-19
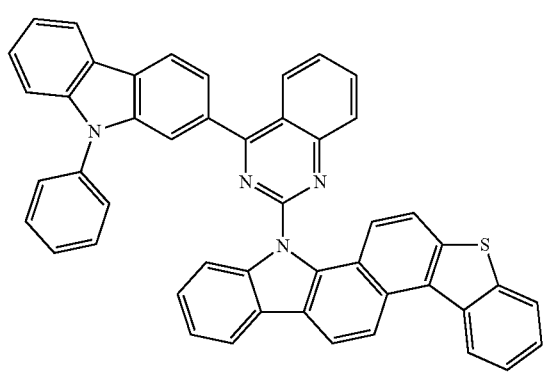
-continued
H-20
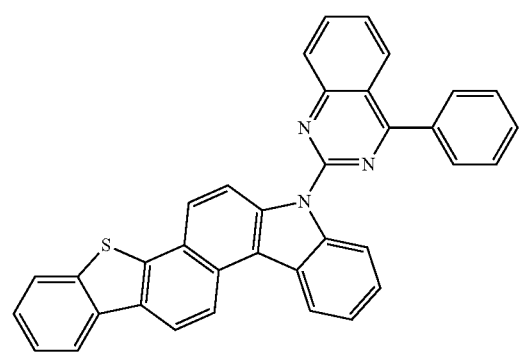
H-21
H-22
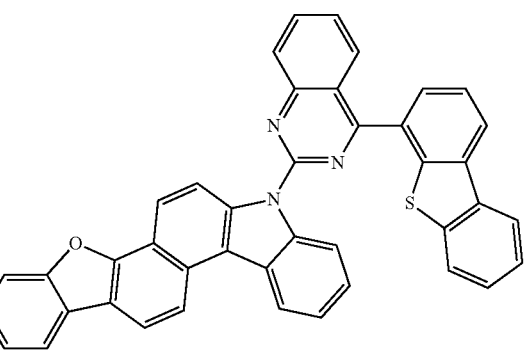
H-23
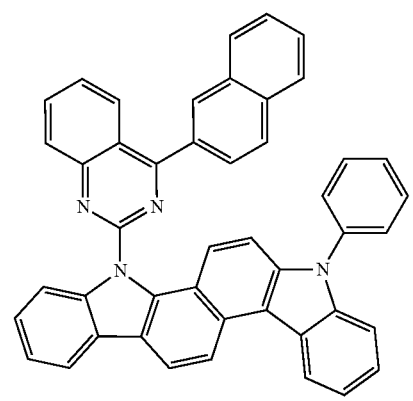

H-24
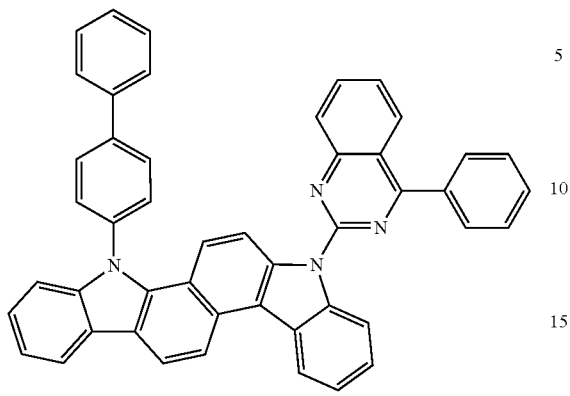
H-25
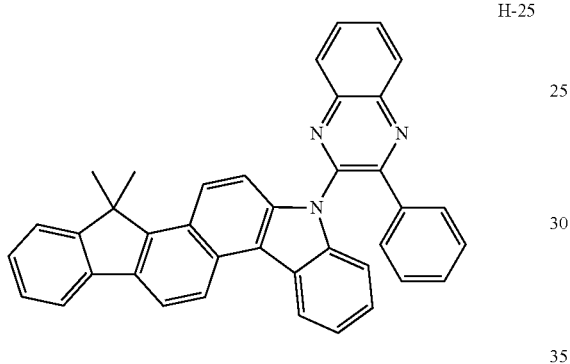
H-26
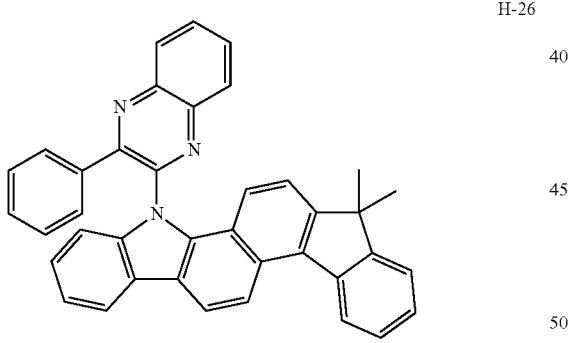
H-27
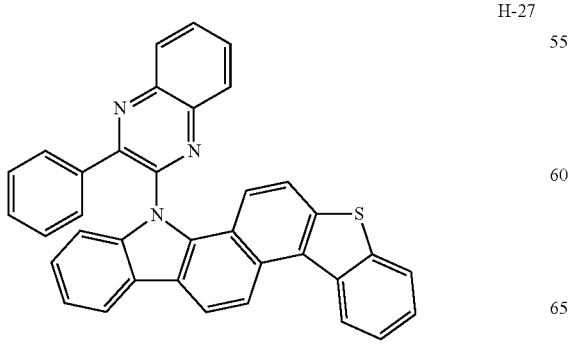
H-28
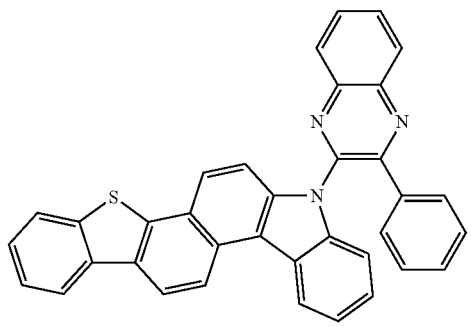
H-29
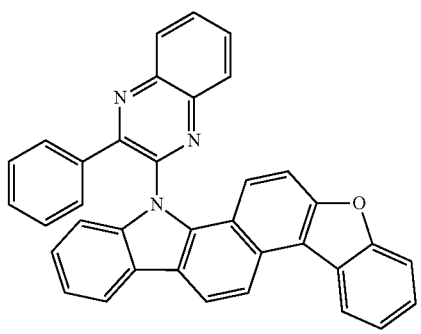
H-30
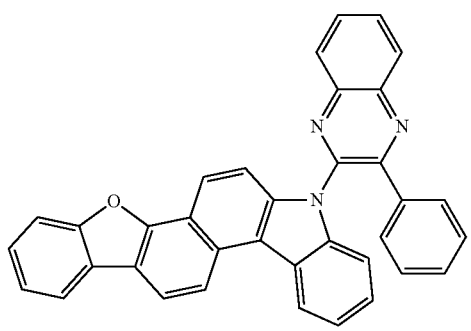
H-31
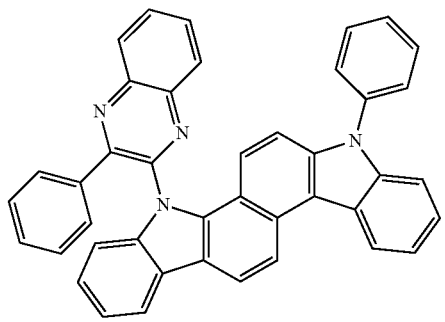

-continued
H-32
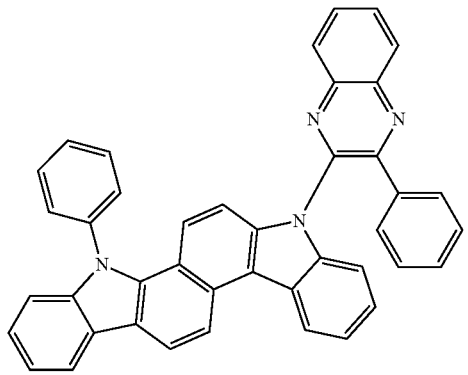
H-33
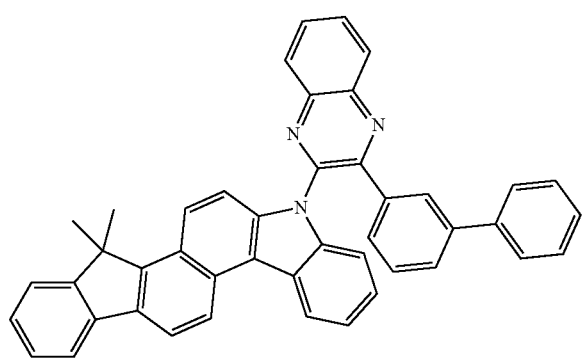
H-34
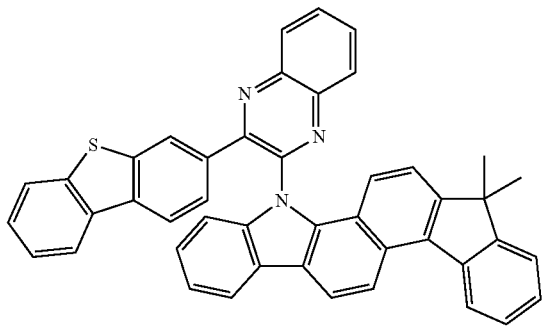
H-35
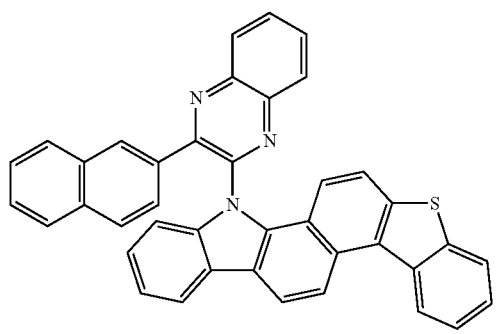
-continued
H-36
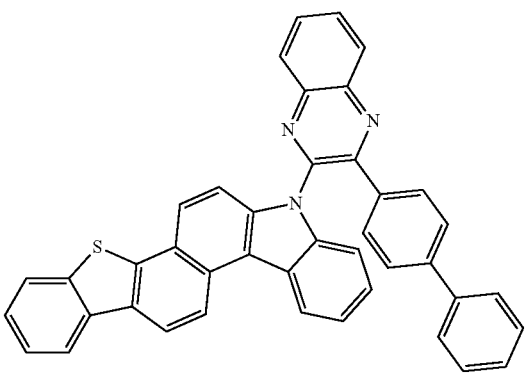
H-37
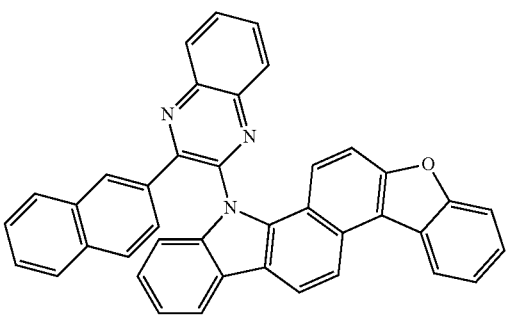
H-38
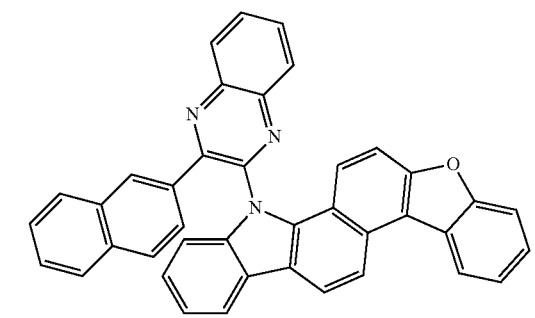
H-39
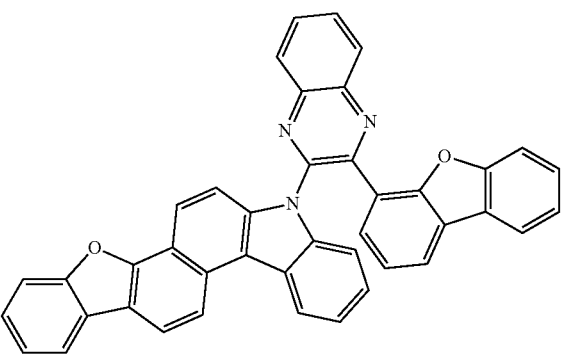

H-40
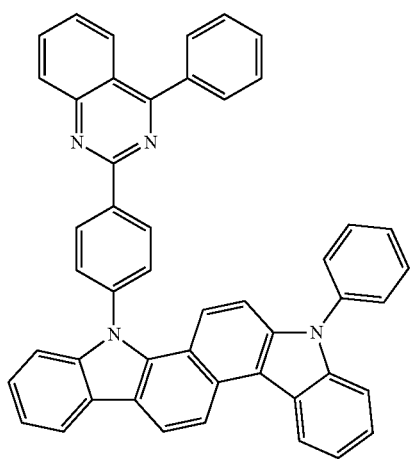
H-41
H-43
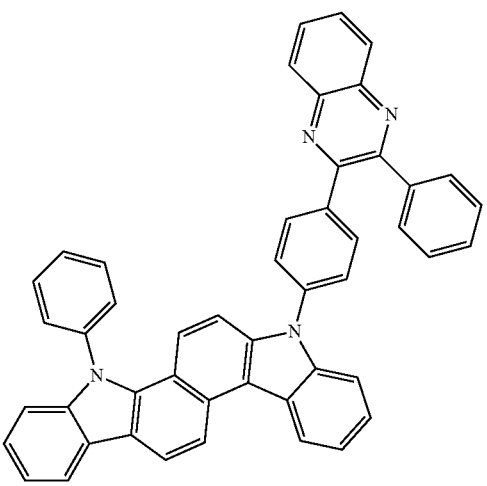
H-44
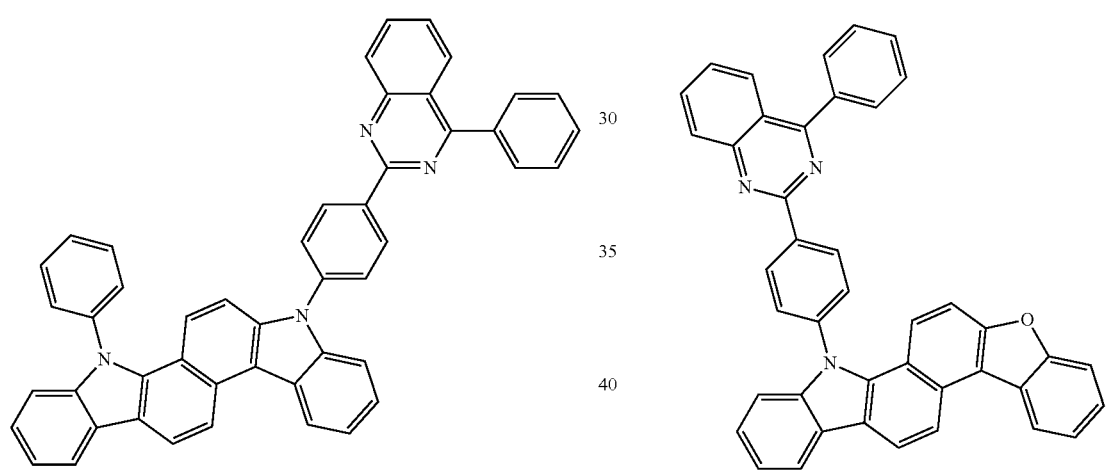
H-42
H-45
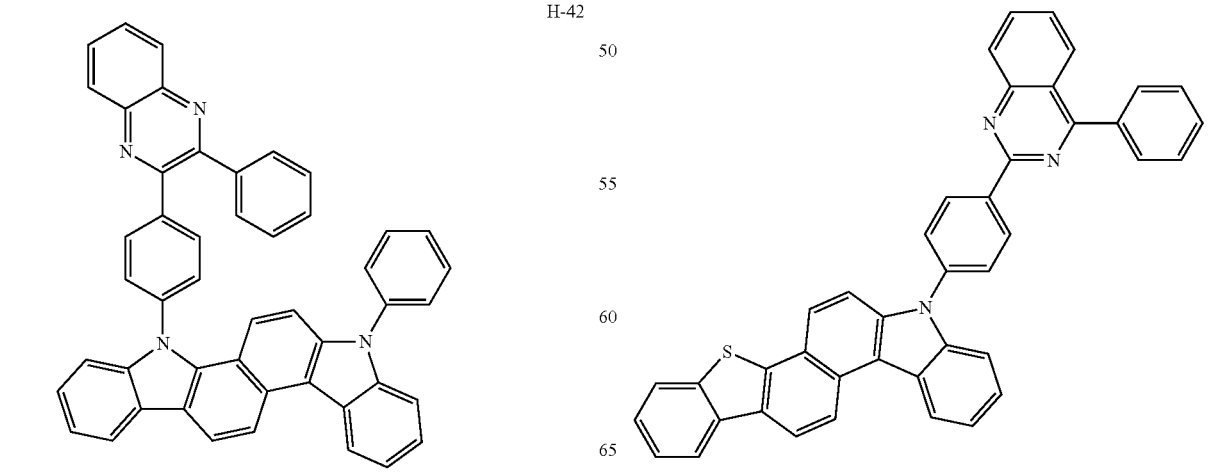

H-46
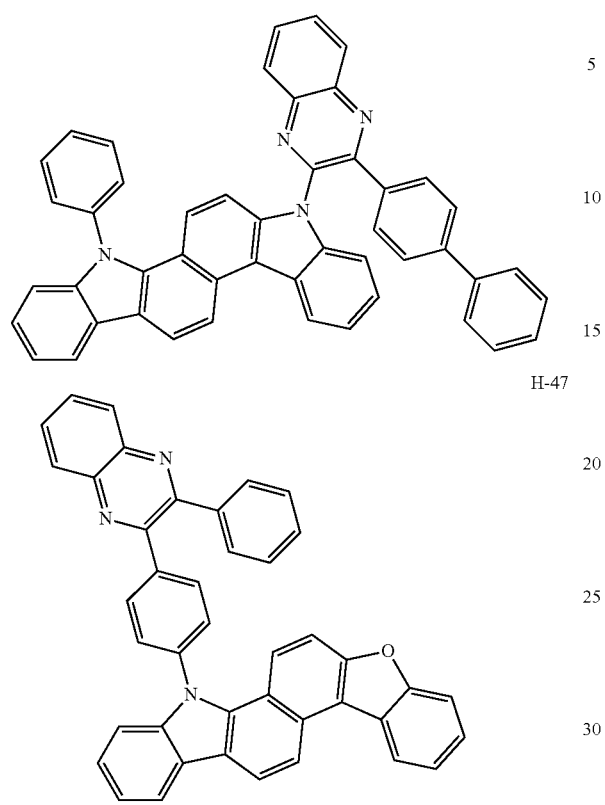
H-47
H-48
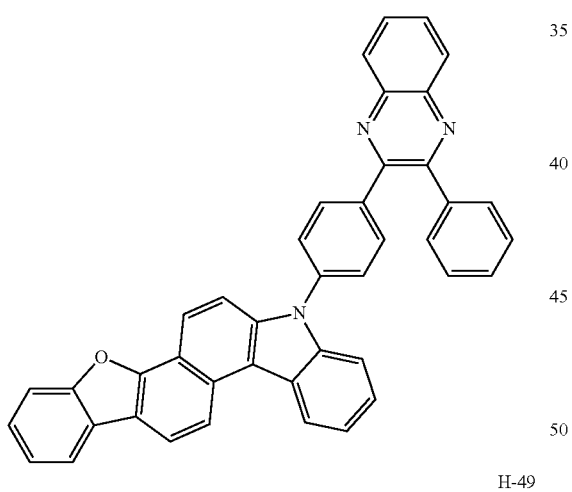
H-49
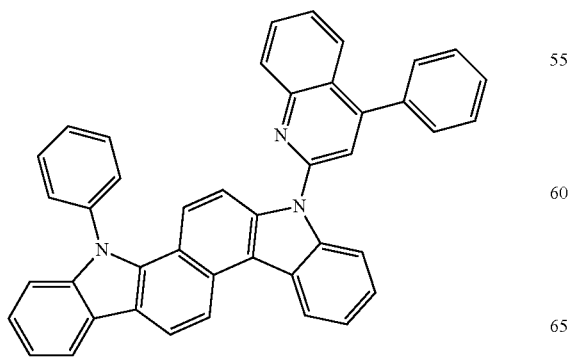
H-50
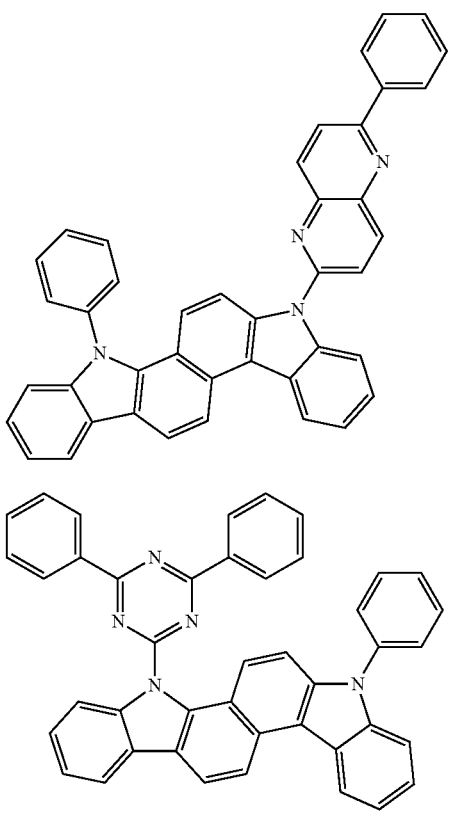
H-51
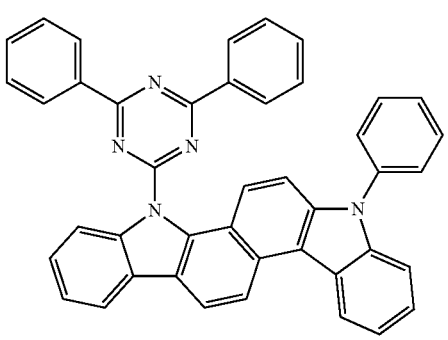
H-52
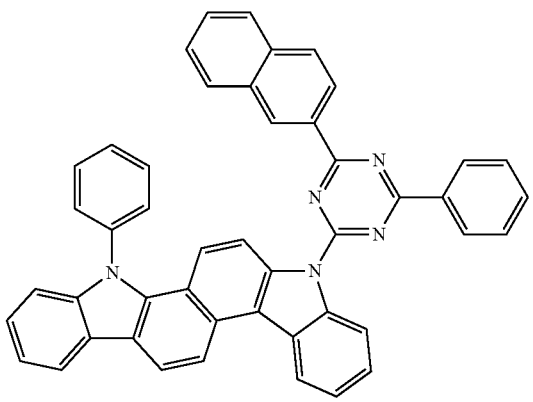
H-53
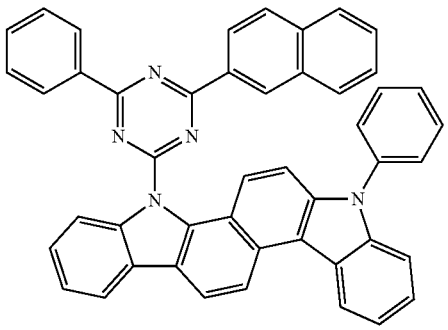

-continued
H-54
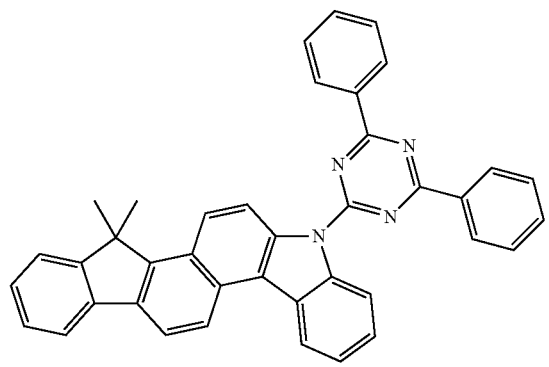
H-55
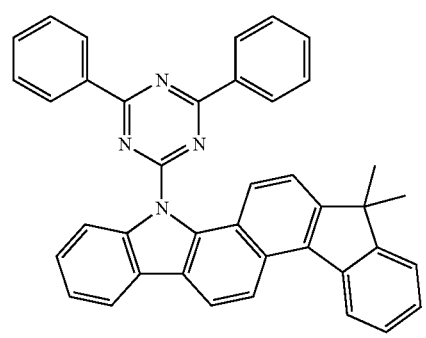
H-56
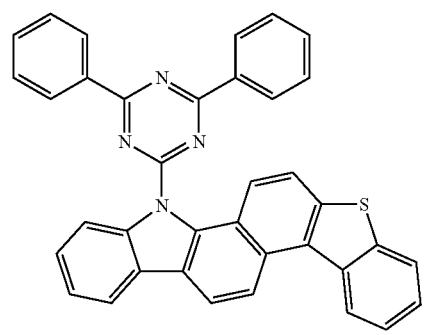
H-57
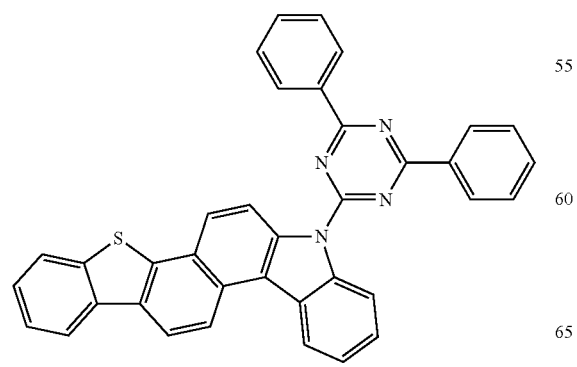
-continued
H-58
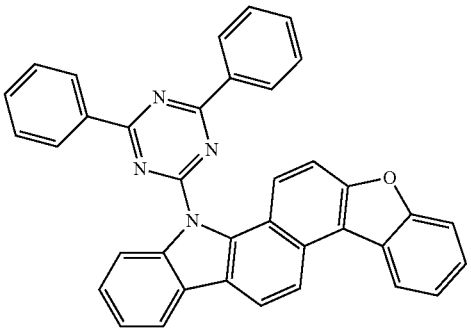
H-59
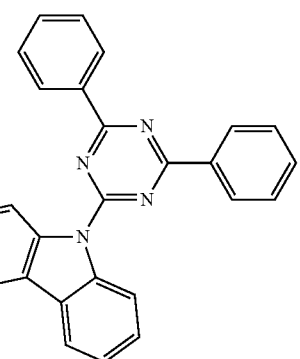
H-60
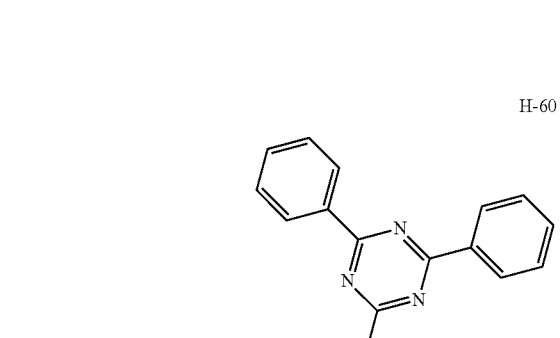
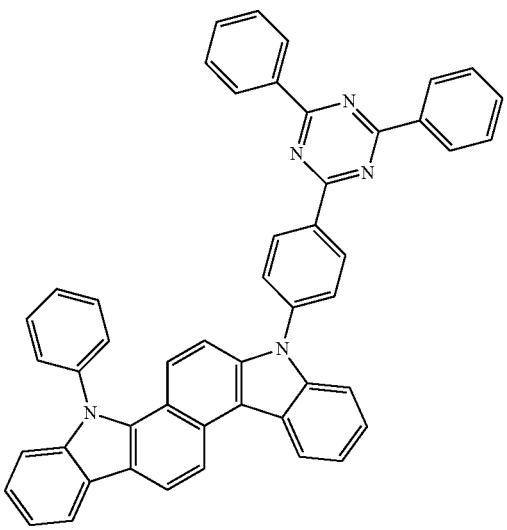

H-61
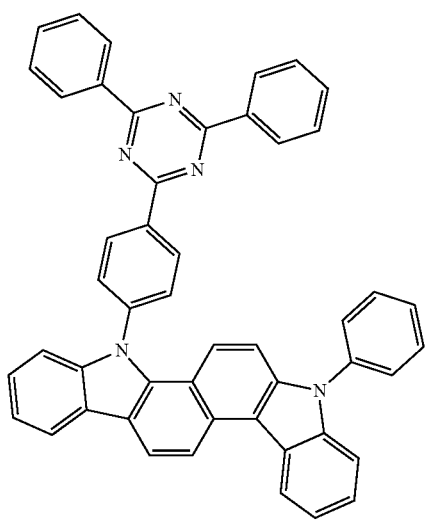
H-62
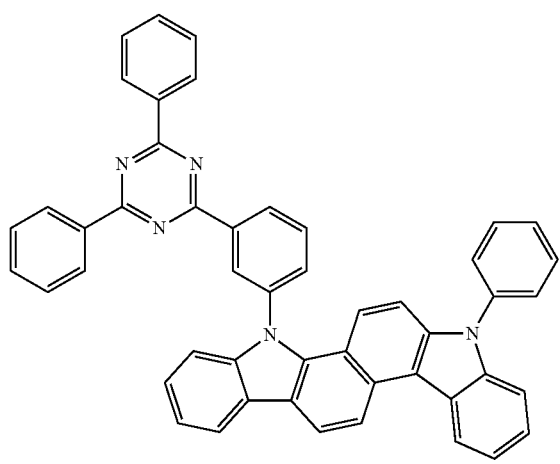
H-63
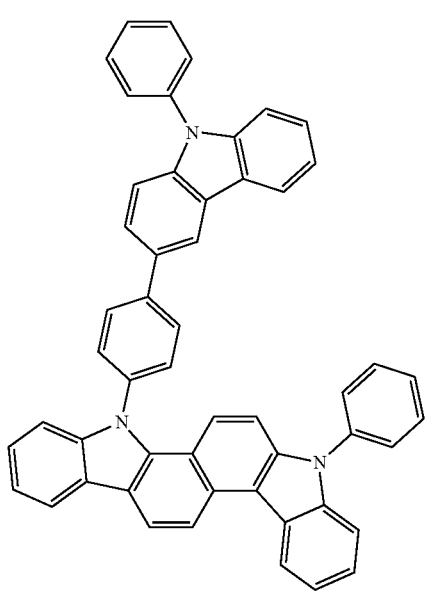
H-64
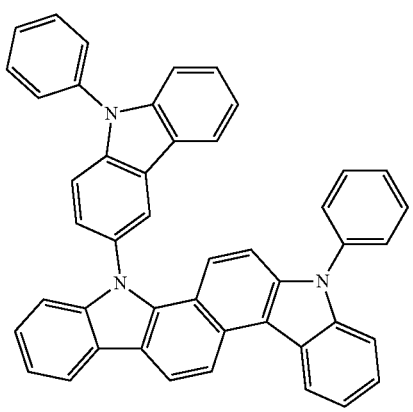
H-65
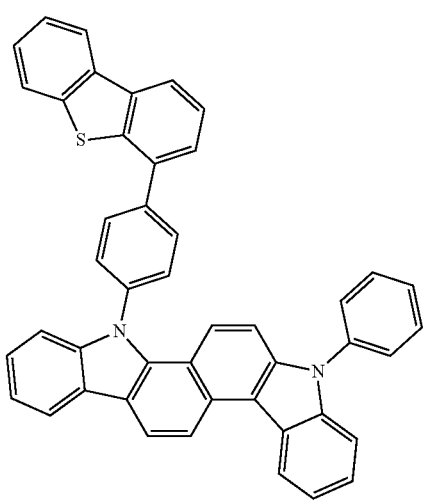
H-66
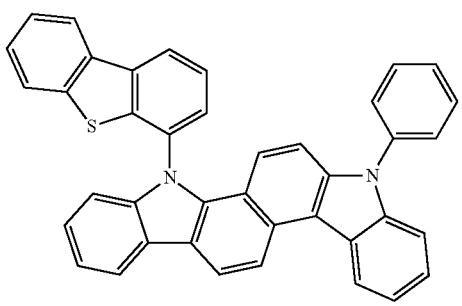

H-67
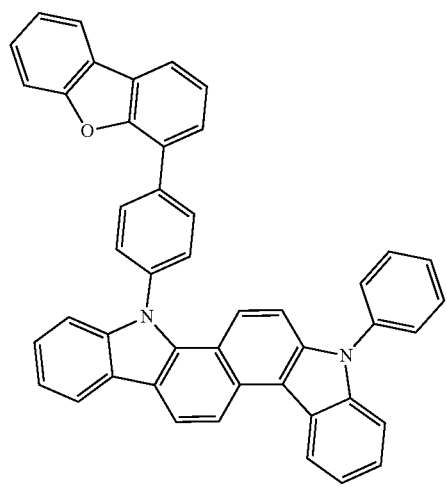
H-68
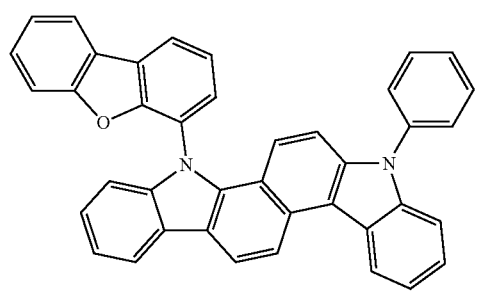
H-69
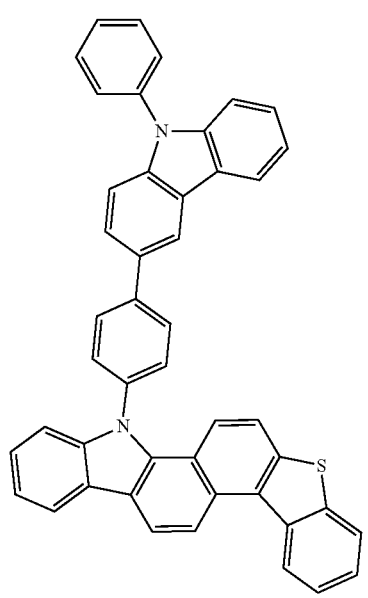
H-70
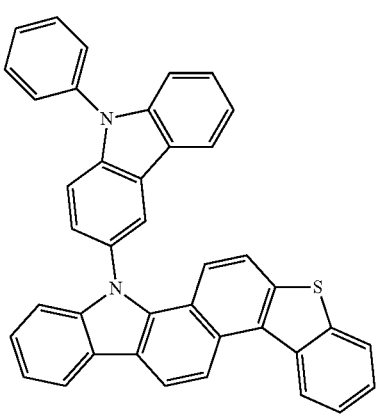
H-71
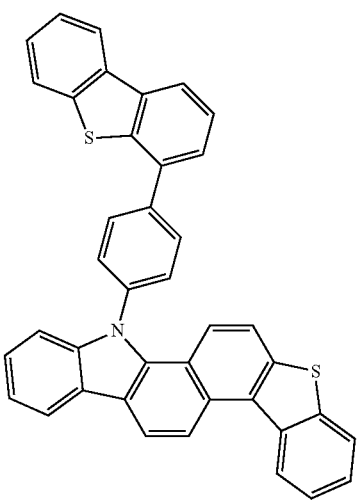
H-72
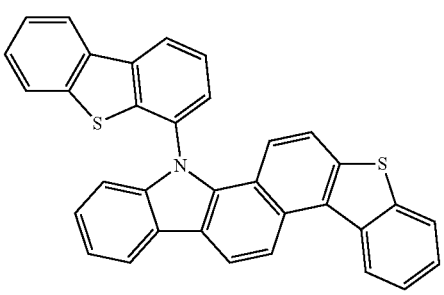

H-73
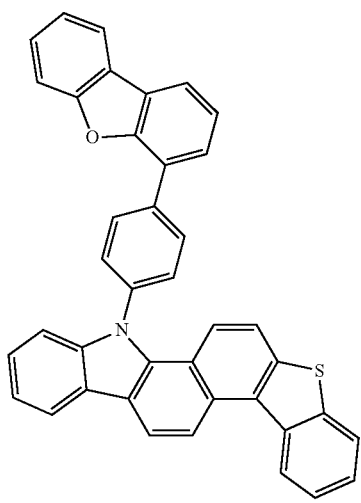
H-74
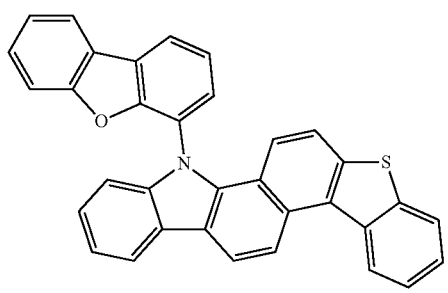
H-75
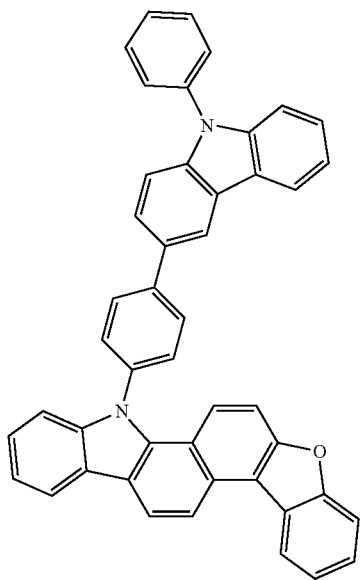
H-76
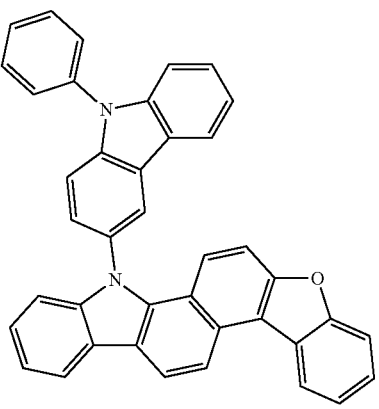
H-77
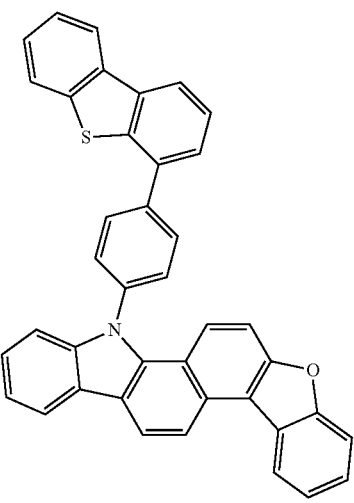
H-78
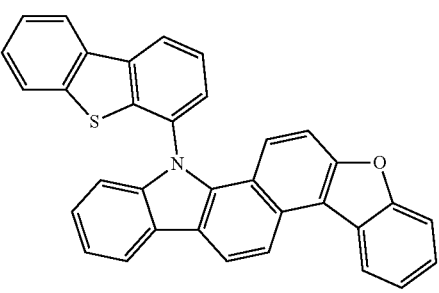

H-79
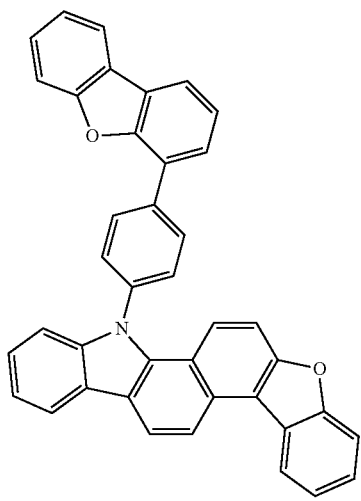
H-80
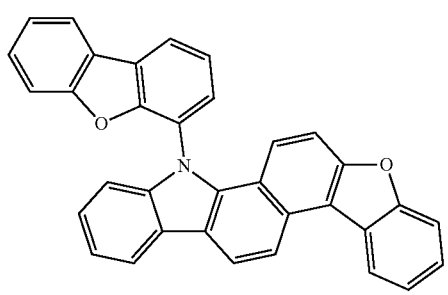
H-81
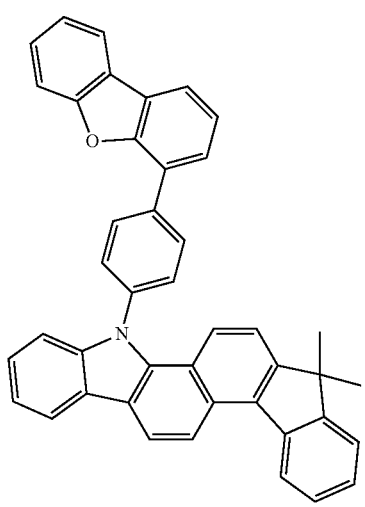
H-82
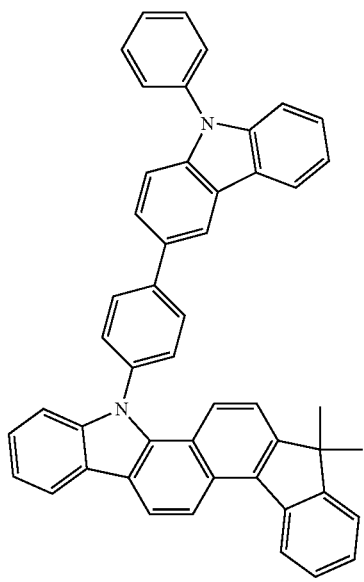
H-83
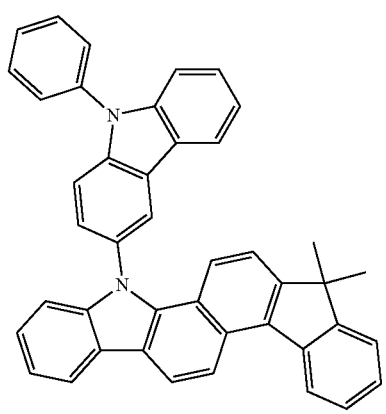
H-84
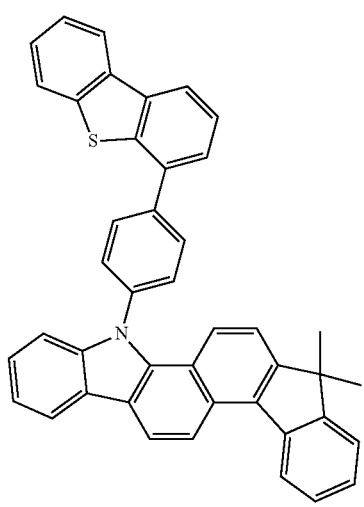

H-85
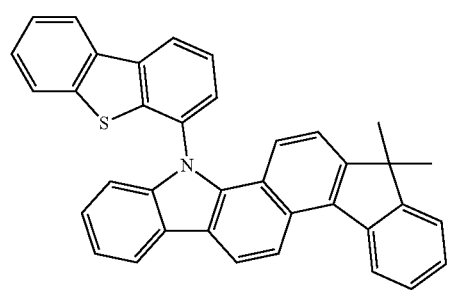
H-86
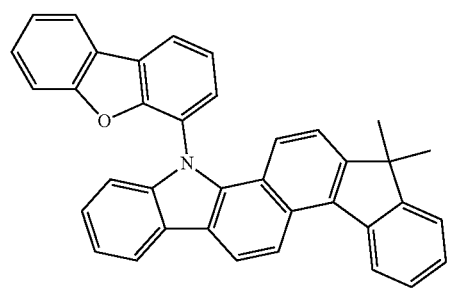
H-87
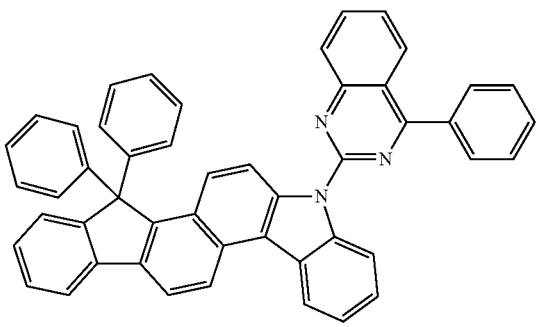
H-88
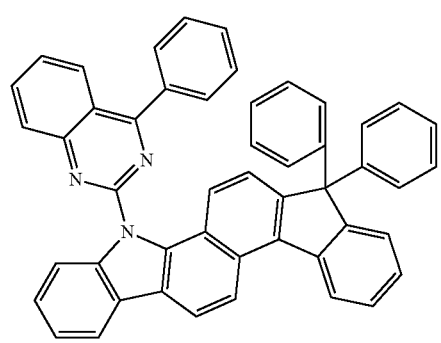
H-89
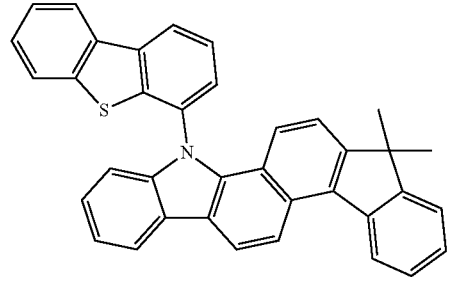
H-90
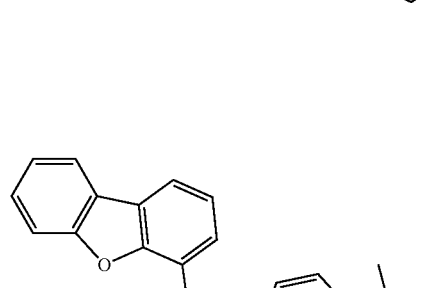
H-91
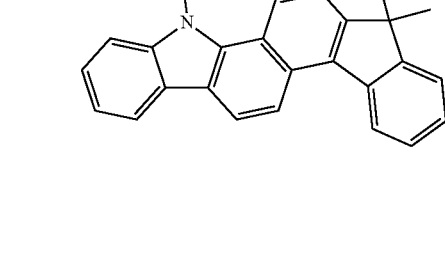
H-92
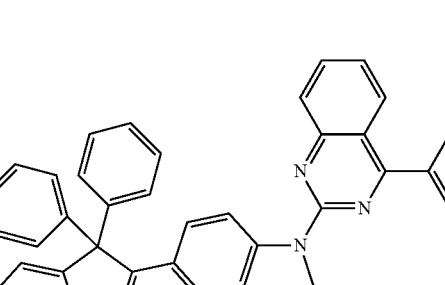

-continued
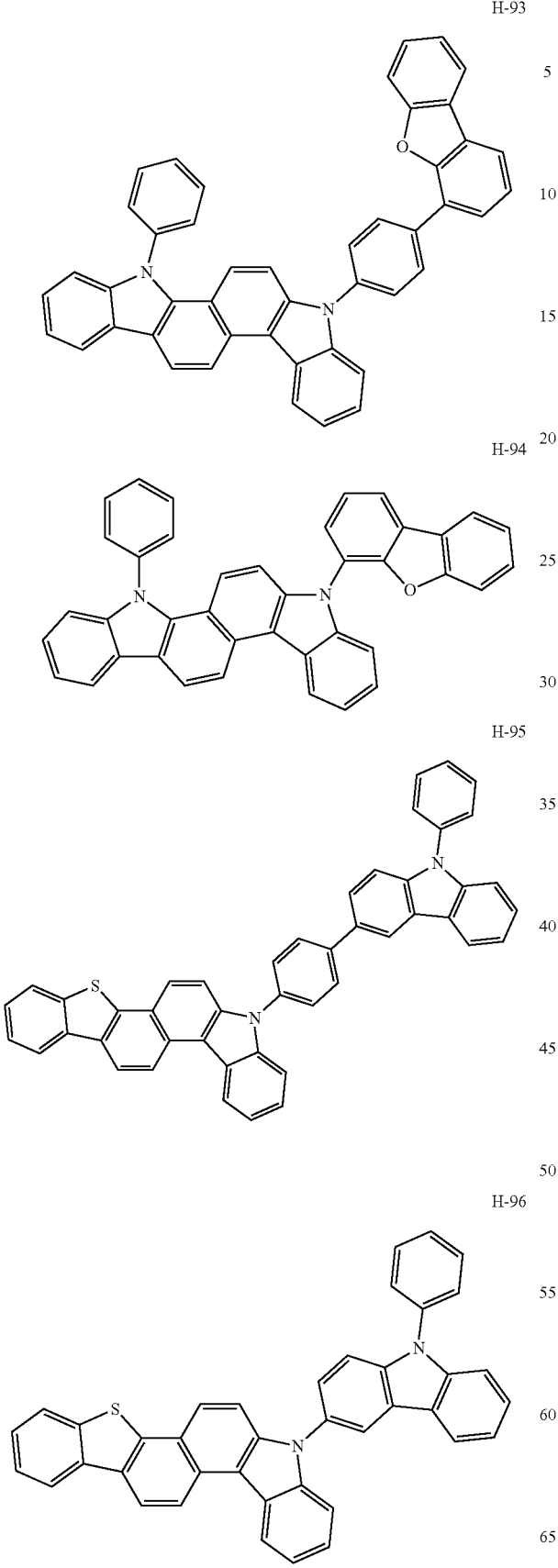
H-93
H-94
H-95
H-96
-continued
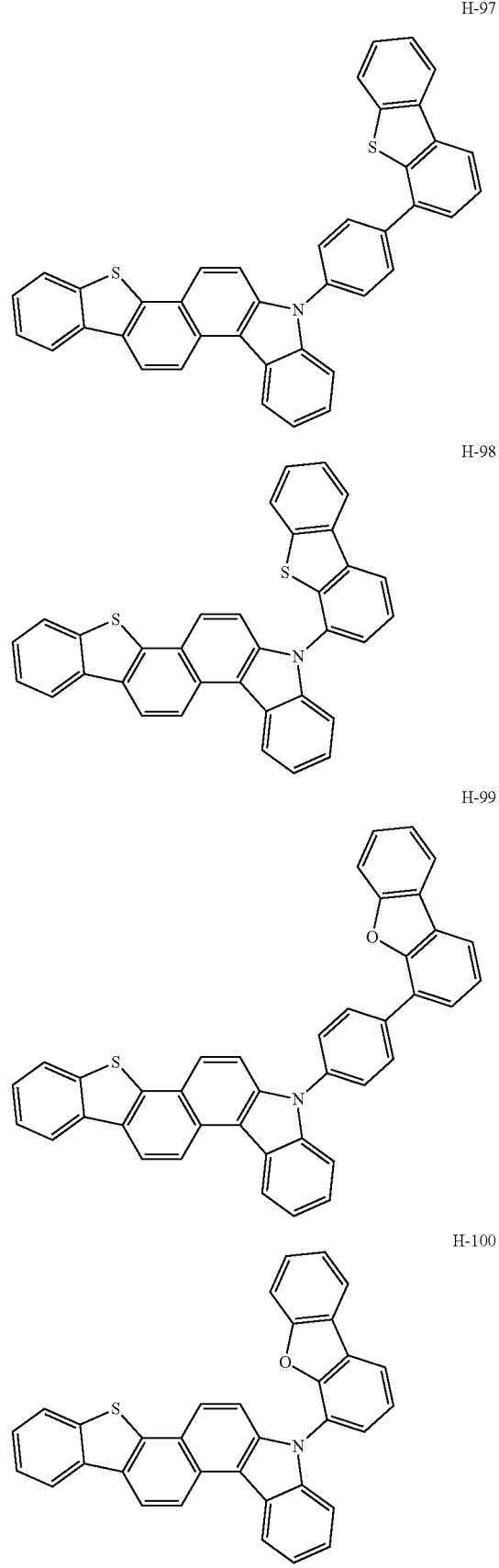
H-97
H-98
H-99
H-100

H-101
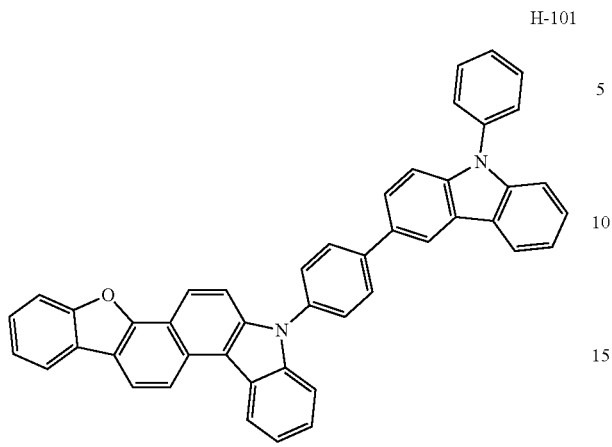
H-102
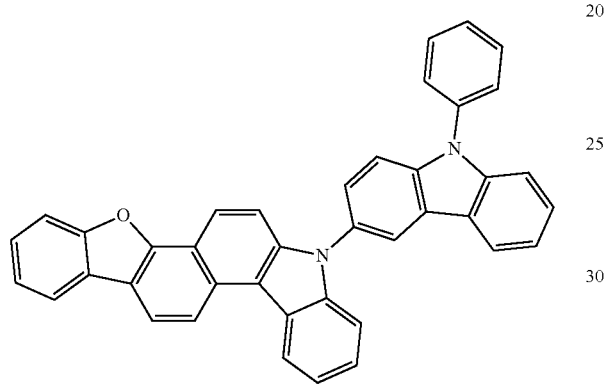
H-103
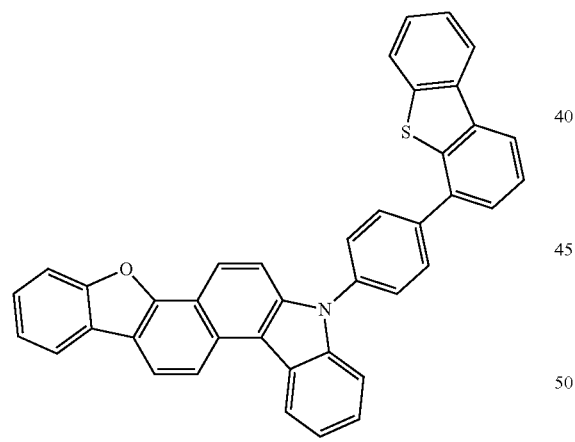
H-104
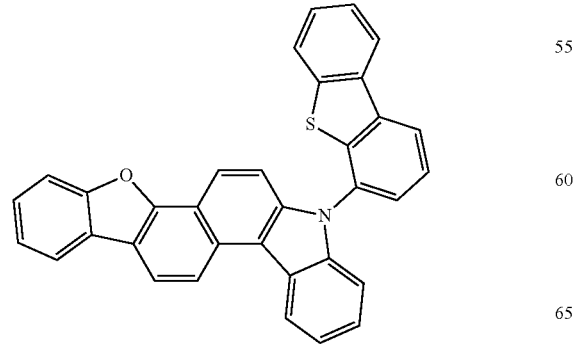
H-105
H-106
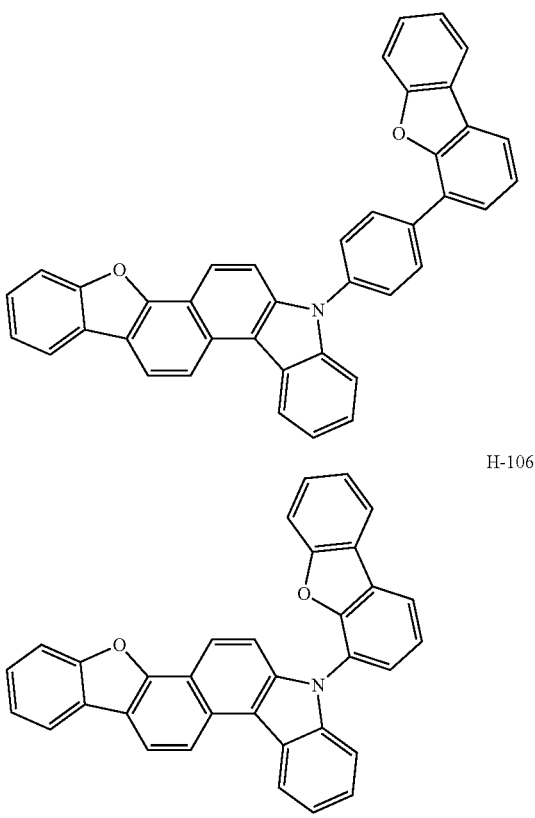
H-107
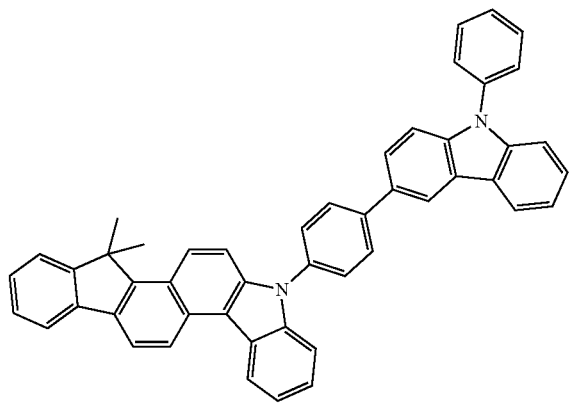
H-108
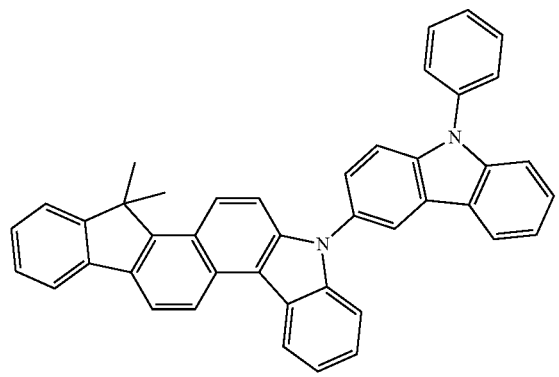

-continued
H-109
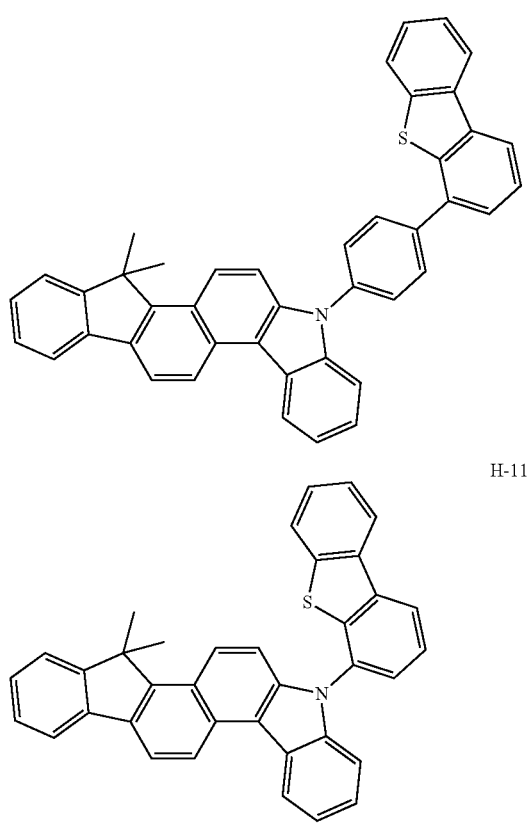
H-110
H-111
H-112
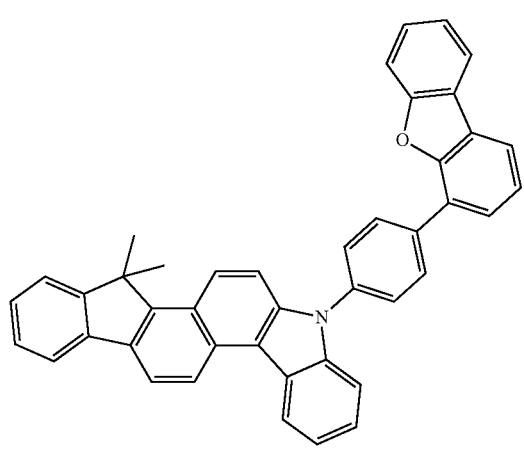
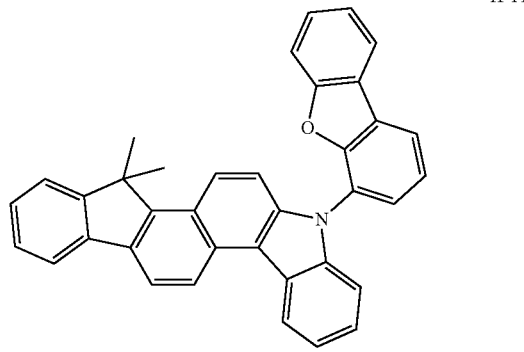
-continued
H-113
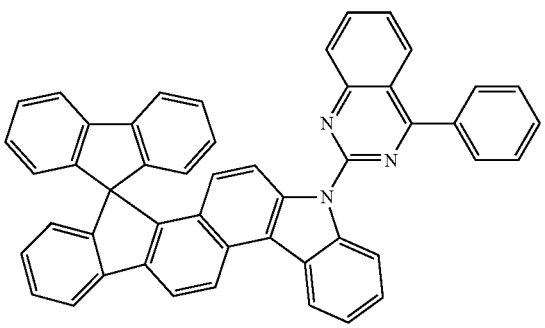
H-114
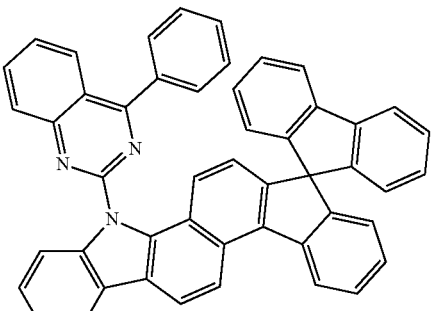
H-115
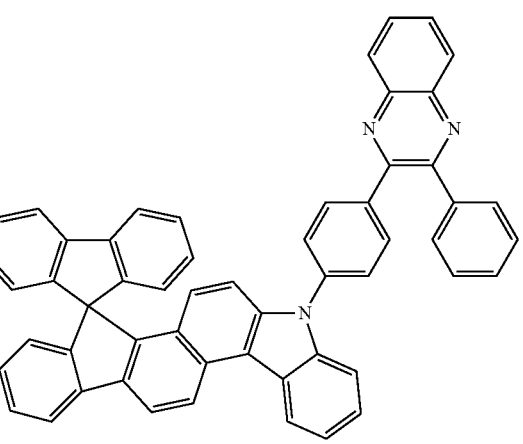
H-116
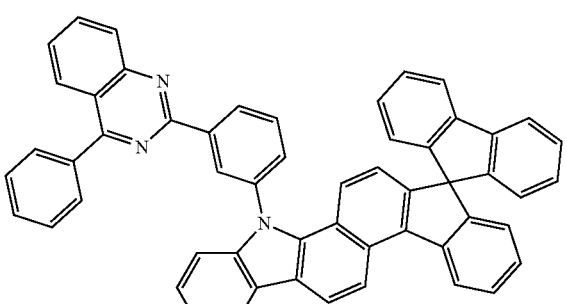
The organic electroluminescent compound of the present disclosure can be prepared by a synthetic method known to one skilled in the art. For example, it can be prepared according to any of the following reaction schemes 1 to 4.

[Reaction Scheme 1]
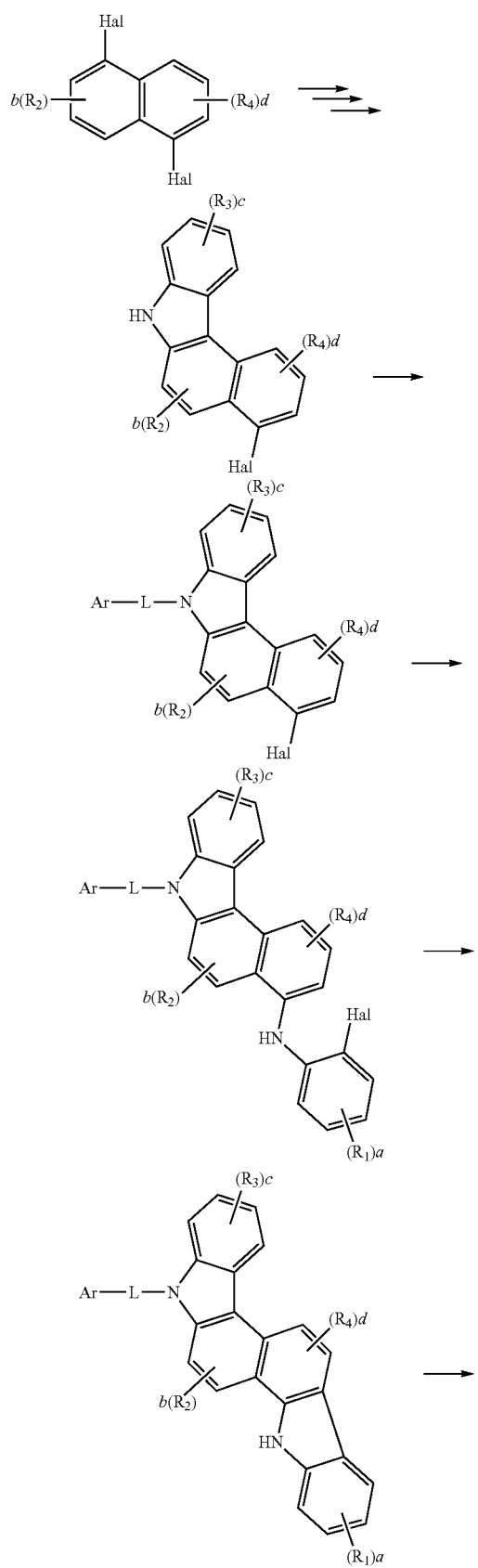
[Reaction Scheme 2]
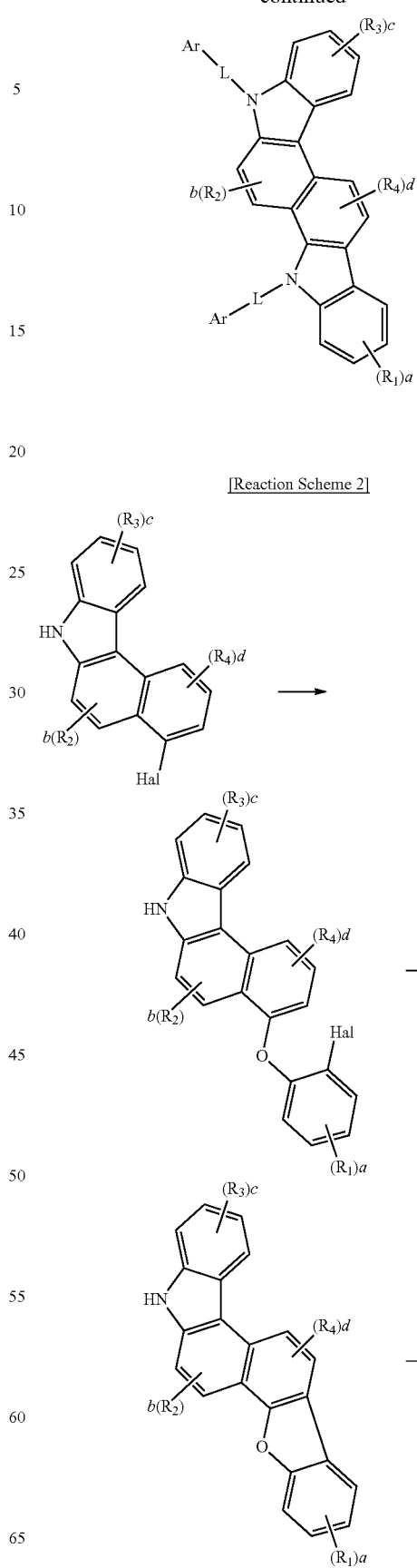

-continued
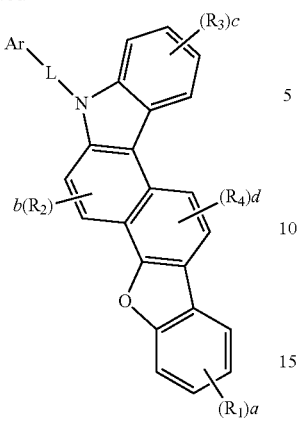
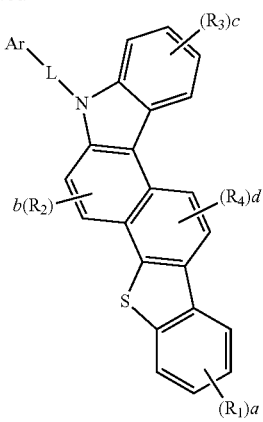
[Reaction Scheme 3]
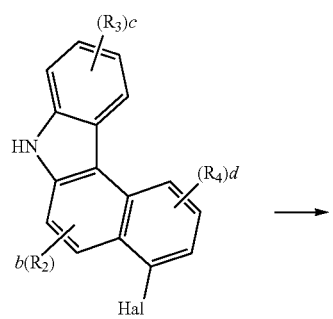
[Reaction Scheme 4]
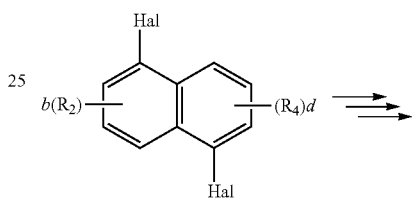
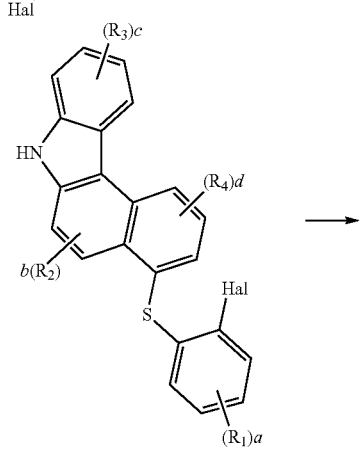
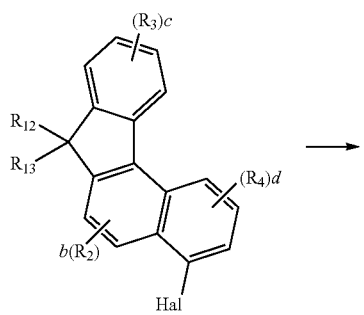
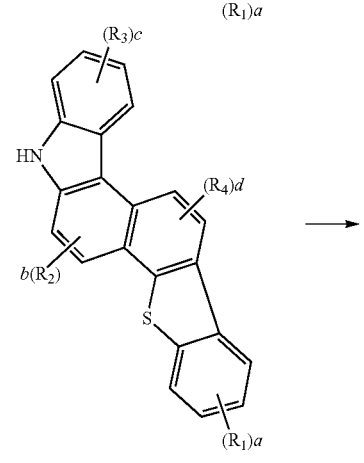
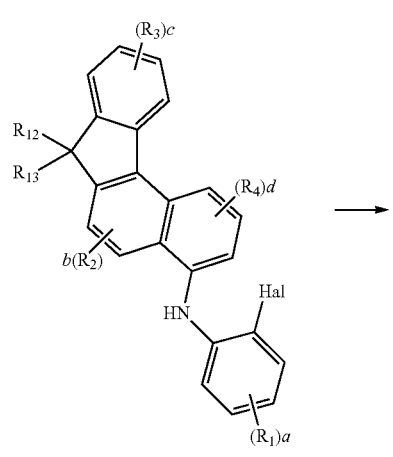

-continued

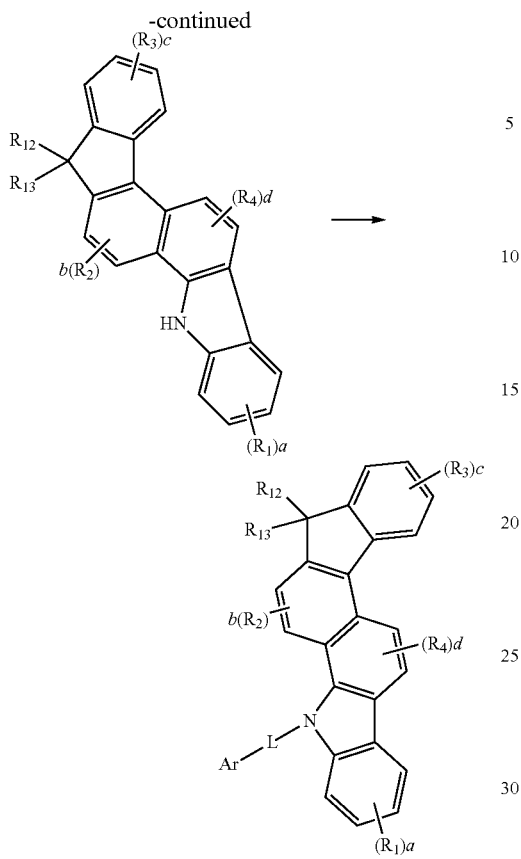

wherein $R_1$ to $R_4$, $R_{12}$, $R_{13}$, $L_1$, Ar, a, b, c, and d are as defined in formula 1 above, and Hal represents a halogen.

The present disclosure provides an organic electroluminescent material comprising the organic electroluminescent compound of formula 1, and an organic electroluminescent device comprising the material.

The material may consist of the organic electroluminescent compound of the present disclosure. Otherwise, the material may further comprise a conventional compound(s) which has been comprised for an organic electroluminescent material.

The organic electroluminescent device of the present disclosure may comprise a first electrode, a second electrode, and at least one organic layer disposed between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, an electron transport layer, an electron injection layer, an interlayer, a hole blocking layer, an electron buffer layer, and an electron blocking layer.

The organic electroluminescent compound of the present disclosure may be comprised in the light-emitting layer. When used in the light-emitting layer, the organic electroluminescent compound of the present disclosure may be comprised as a host material. Preferably, the light-emitting layer may further comprise at least one or more dopants, and, if necessary, a second host material other than the compound of formula 1 of the present disclosure. The second host material may be from any of the known phosphorescent hosts. The weight ratio between the organic electroluminescent compound of formula 1 of the present disclosure and the second host material is in the range of 1:99 to 99:1.

The material selected from the group consisting of the compounds of formulae 11 to 15 is preferably the second host material in view of luminous efficiency.

 (11)

 (12)

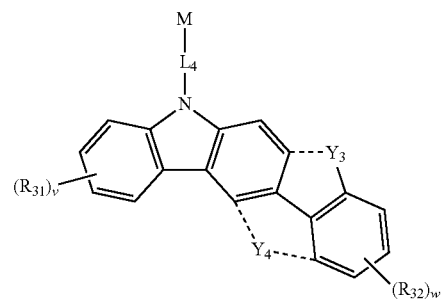 (13)

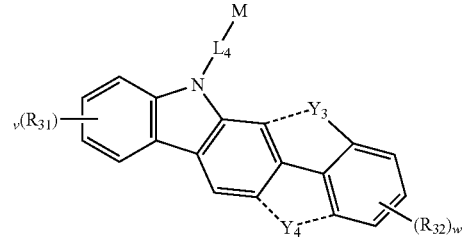 (14)

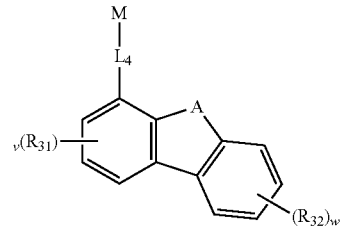 (15)

wherein Cz represents the following structure:

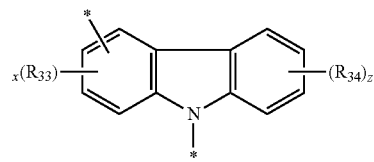

A represents —O— or —S—; $R_{31}$ to $R_{34}$, each independently, represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, or —SiR$_{35}$R$_{36}$R$_{37}$; $R_{35}$ to $R_{37}$, each independently, represent a substituted or unsubstituted (C1-C30)alkyl, or a substituted or unsubstituted (C6-C30)aryl; $L_4$ represents a single bond, a substituted or unsubstituted (C6-C30)arylene, or a substituted or unsubstituted 5- to 30-membered heteroarylene; M represents a substituted or unsubstituted (C6-C30)aryl, or a substituted or unsubstituted 5- to 30-membered heteroaryl; $Y_3$ and $Y_4$, each independently, represent —O—, —S—, —N($R_{41}$)—, or —C($R_{42}$)($R_{43}$)—, and $Y_3$ and $Y_4$ are not present simultaneously; $R_{41}$ to $R_{43}$, each independently, represent a substituted or unsubstituted (C1-C30)alkyl, a substituted or unsubstituted (C6-C30)aryl, or a substituted or unsubstituted 5- to 30-membered heteroaryl; $R_{42}$ and $R_{43}$ may be the same or different; t and u, each independently, represent an integer of 1 to 3; v, w, x and z, each independently, represent an integer of 0 to 4; and where t, u, v, w, x, or y is an integer of 2 or more, each of (Cz-$L_4$), (Cz), $R_{31}$, $R_{32}$, $R_{33}$, or $R_{34}$ may be the same or different.

Specifically, the second host material includes the following, but is not limited thereto.

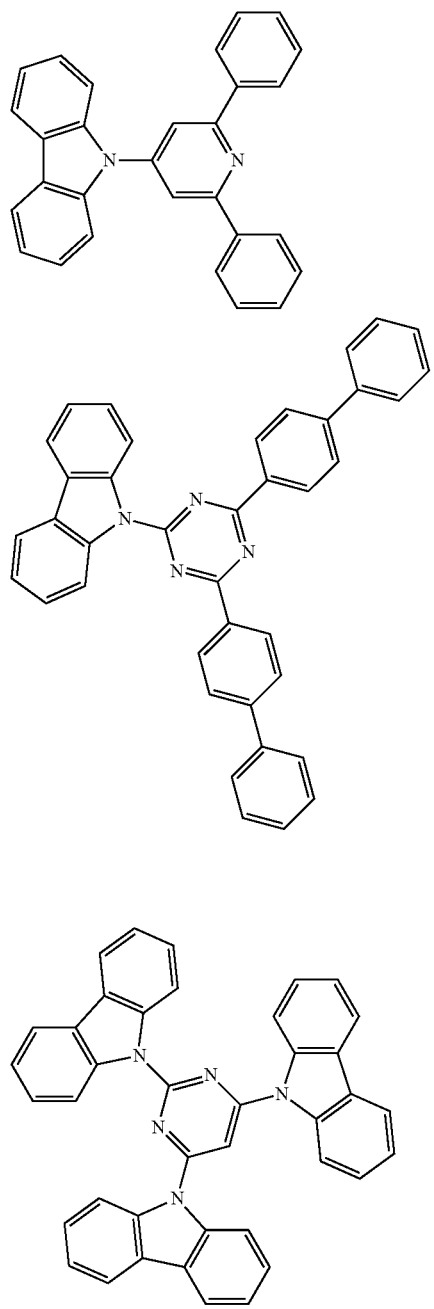

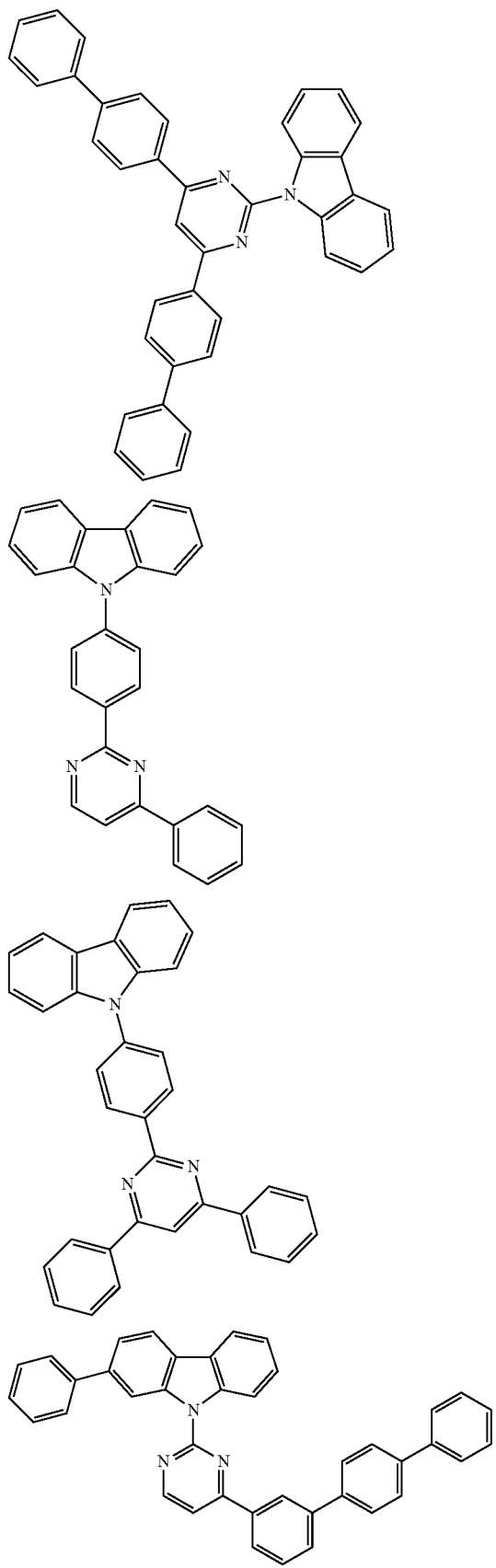

47
-continued
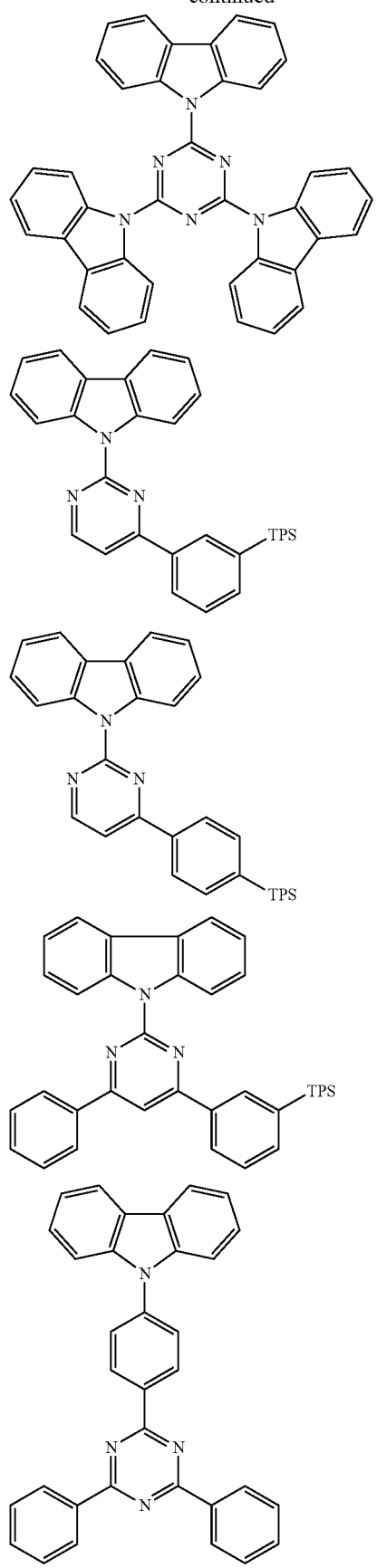
48
-continued
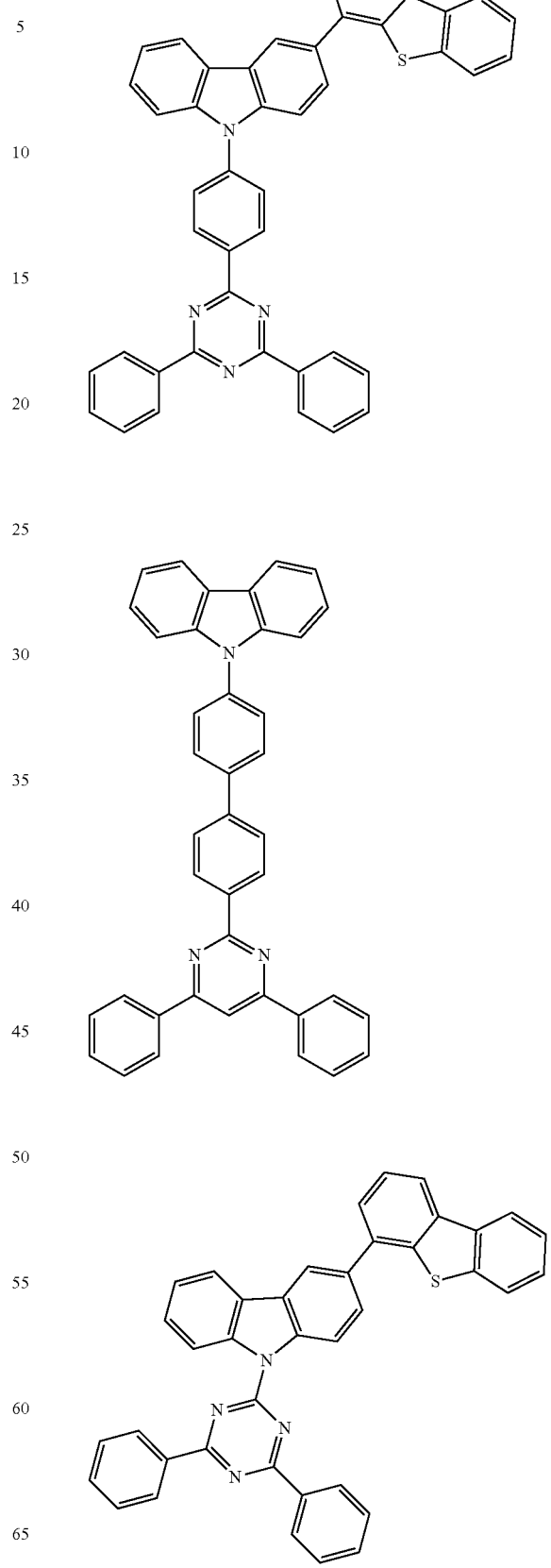

49
-continued
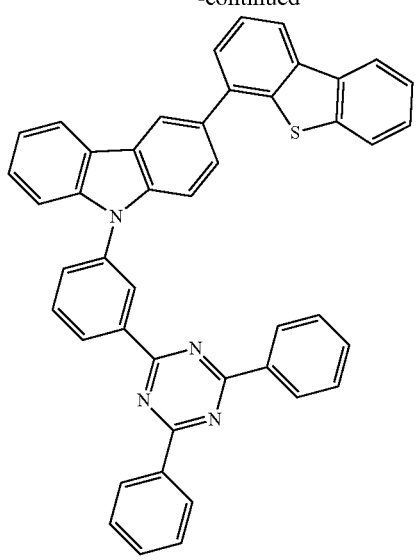
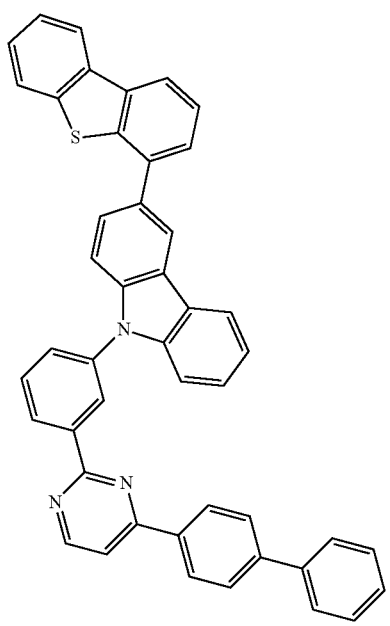
50
-continued
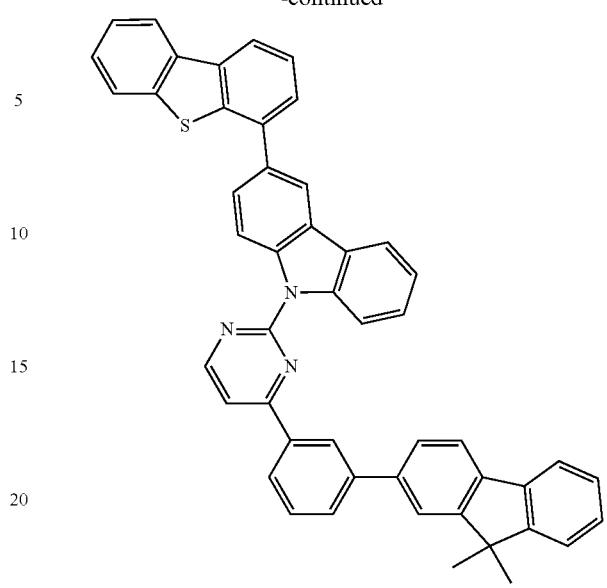
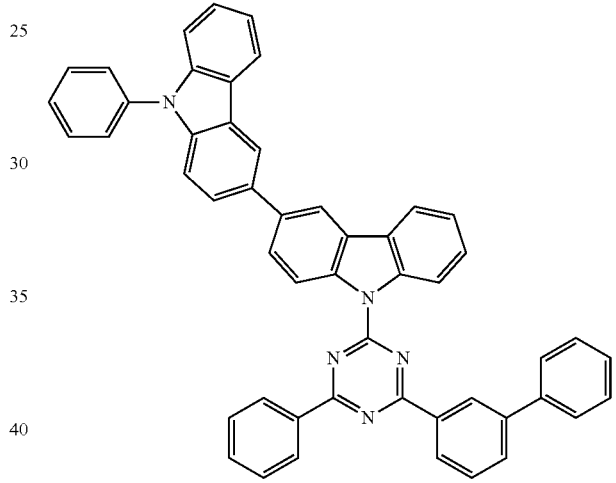
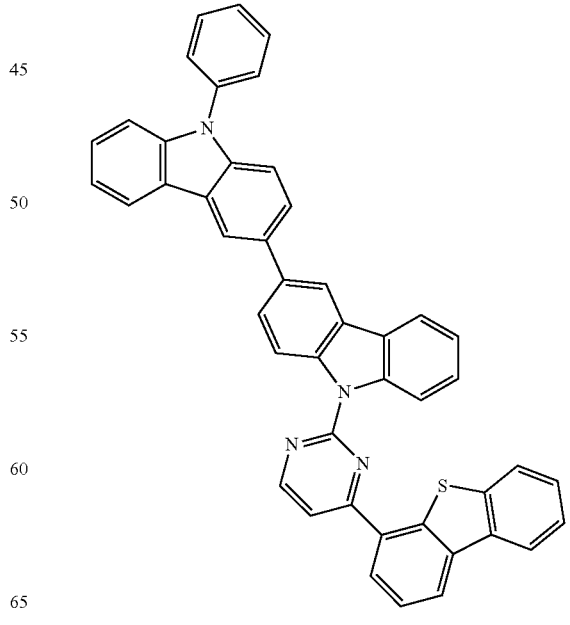

51
-continued
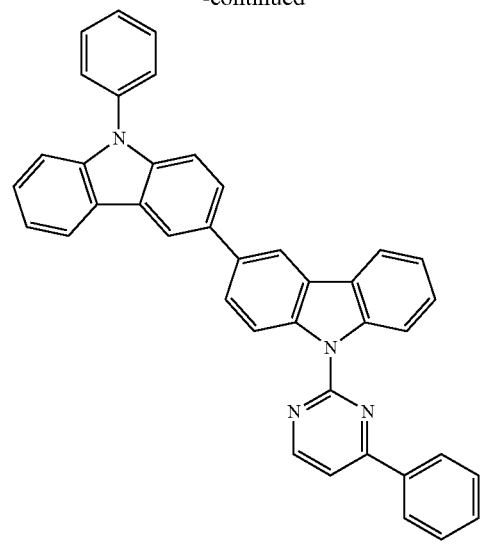
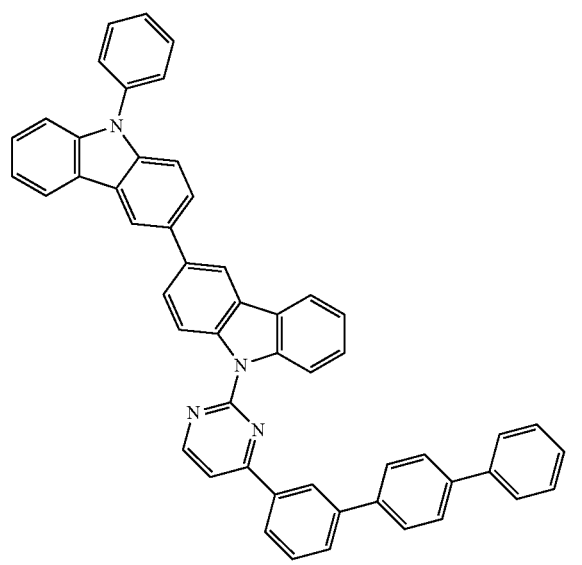
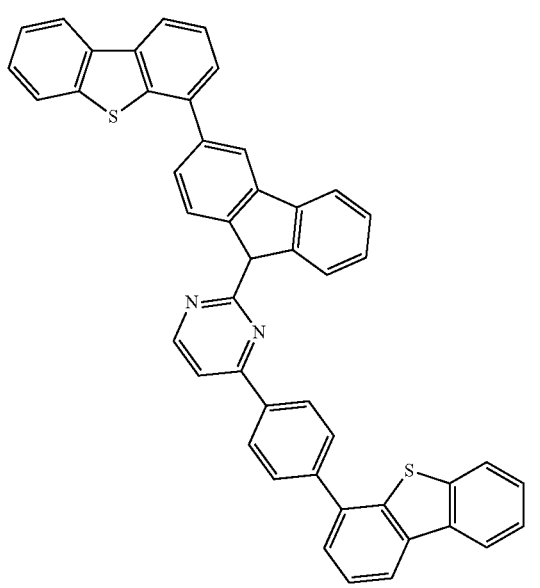
52
-continued
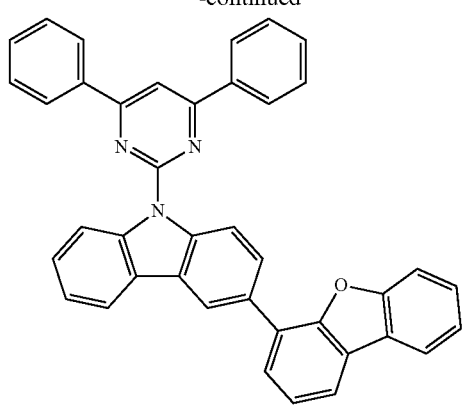
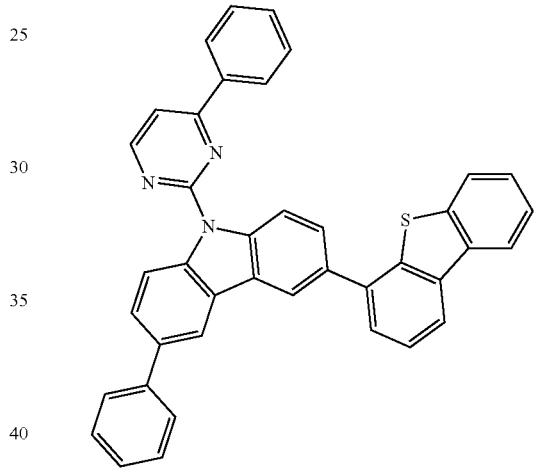
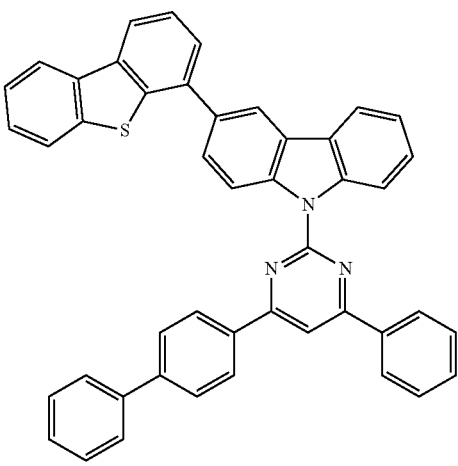

53
-continued
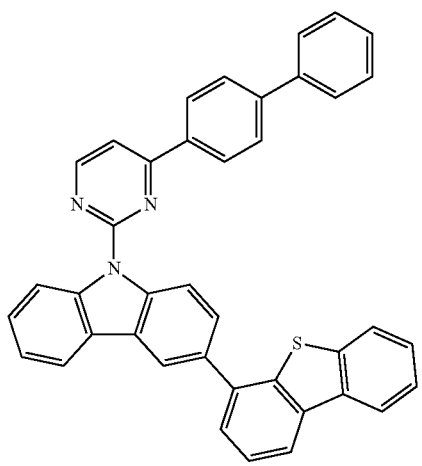
54
-continued
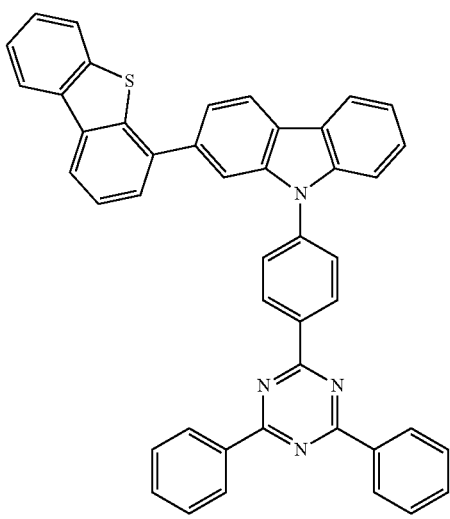
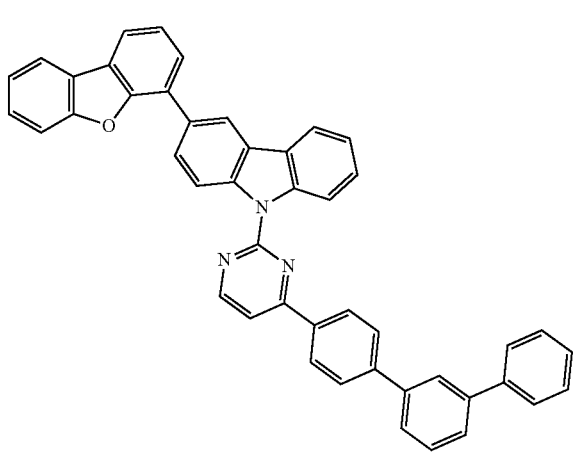
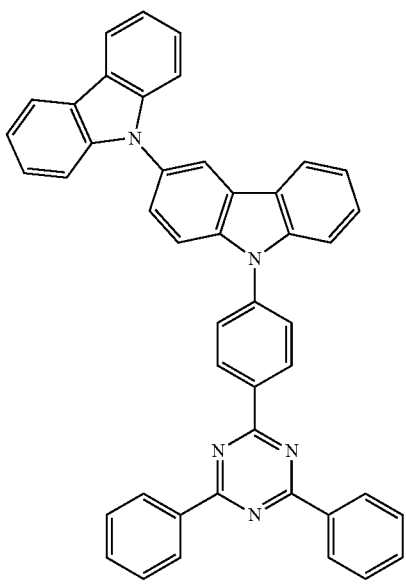

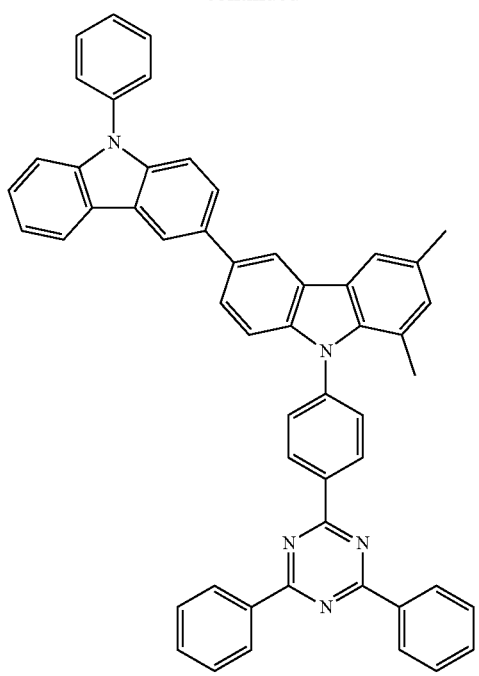
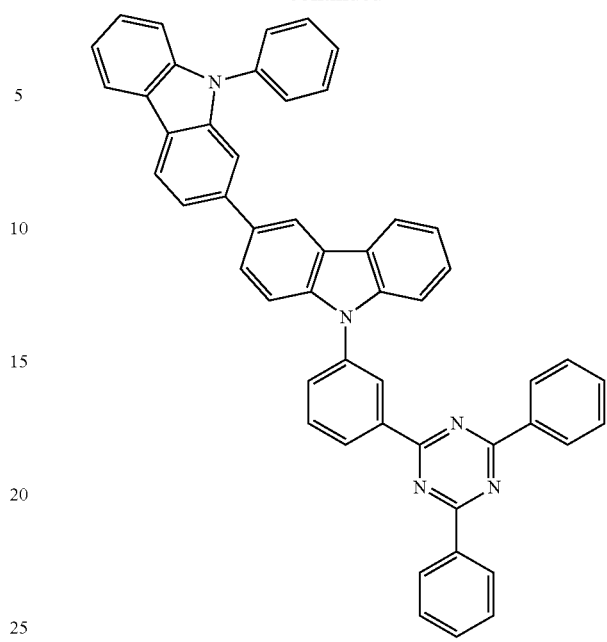
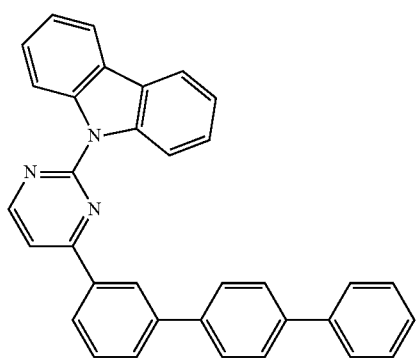
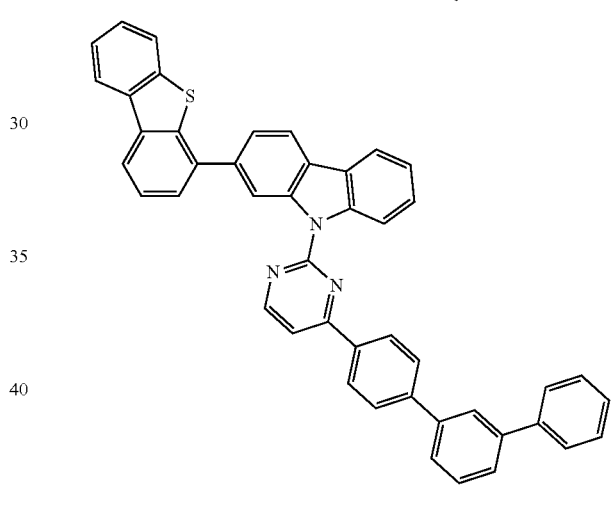
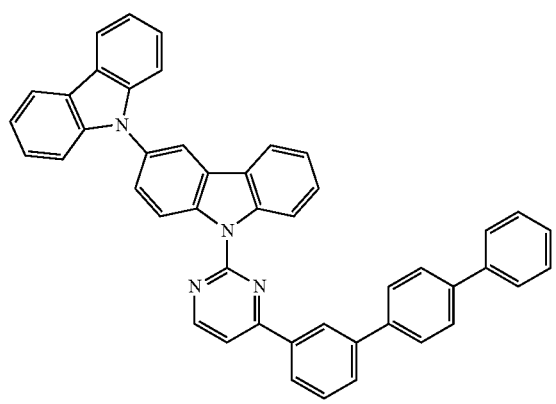
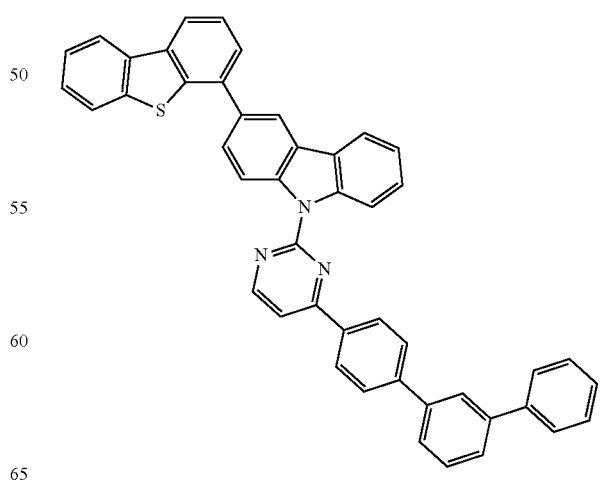

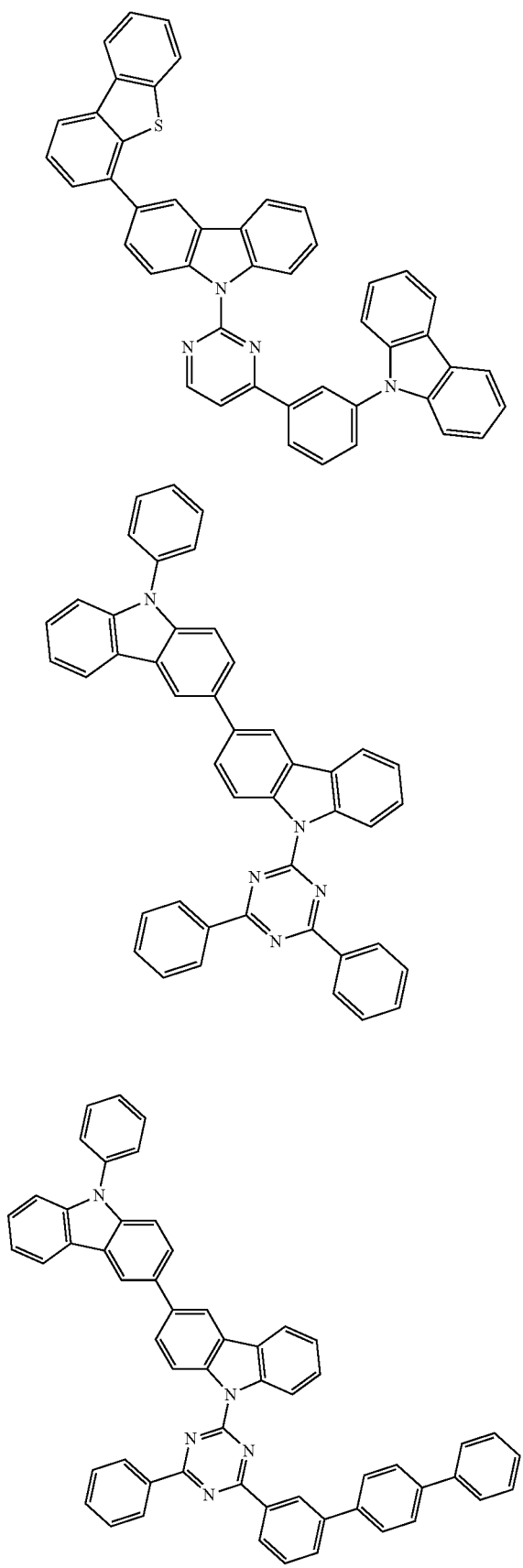
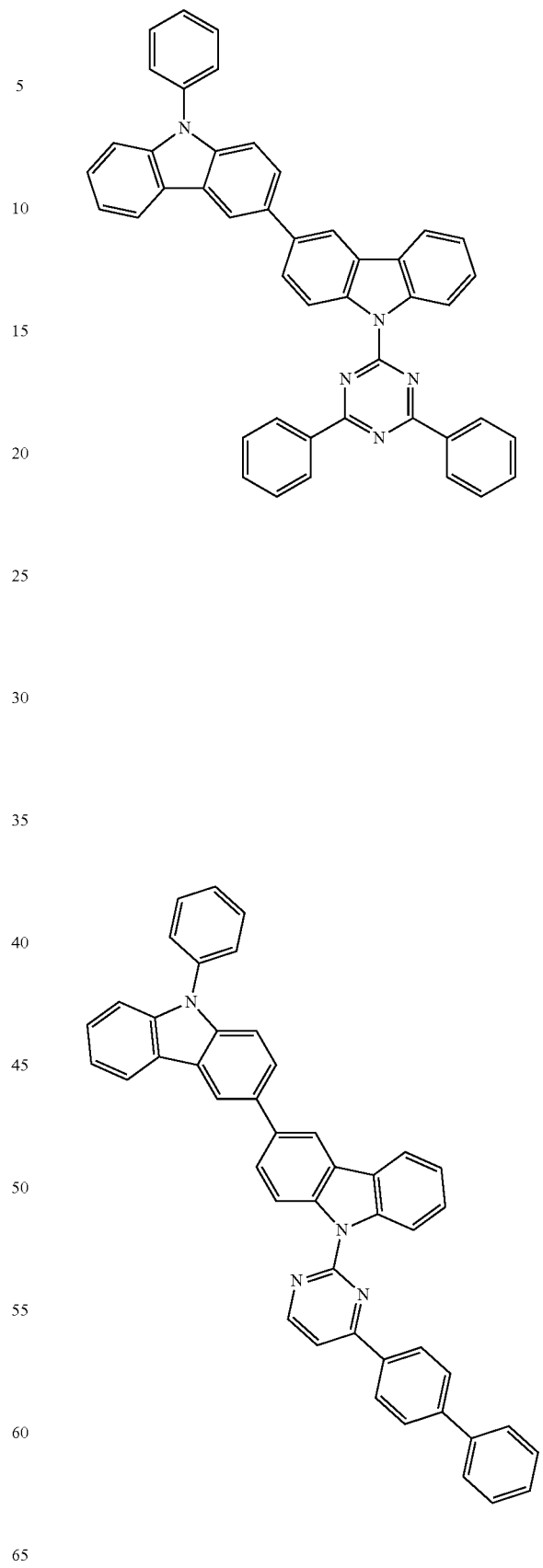

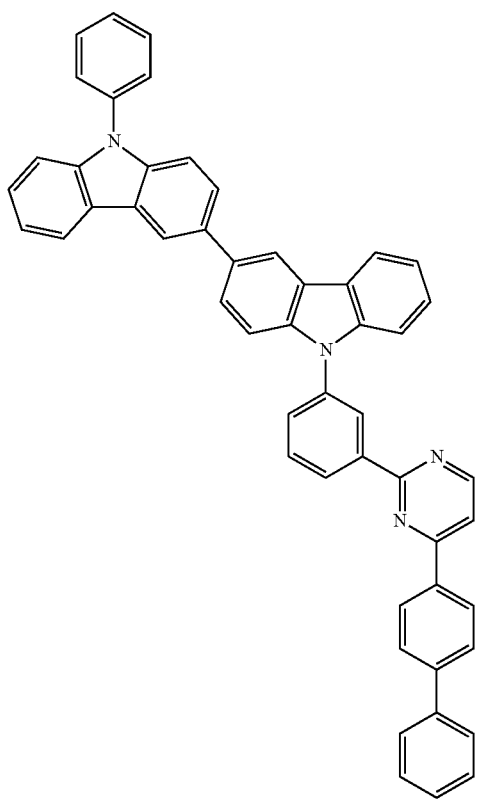
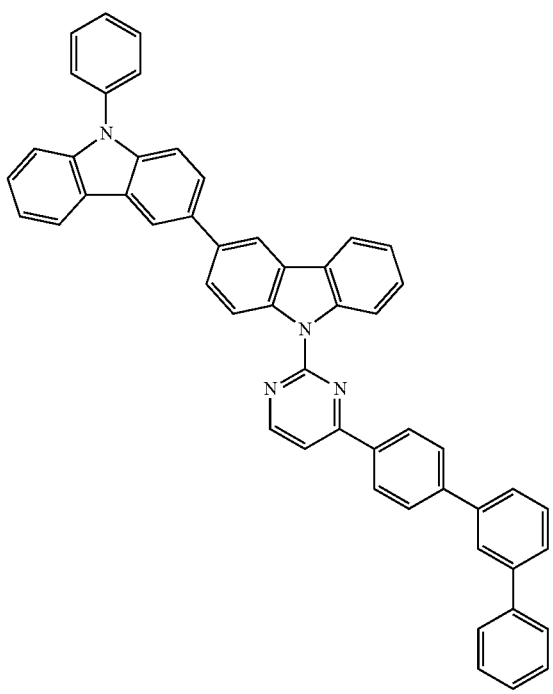
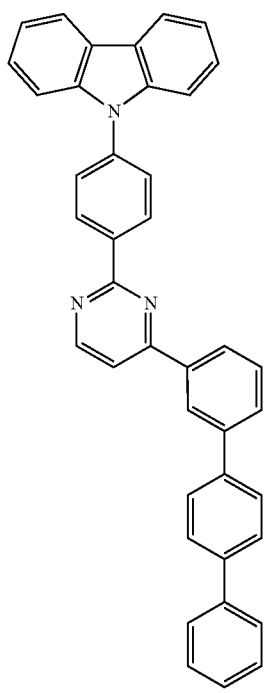

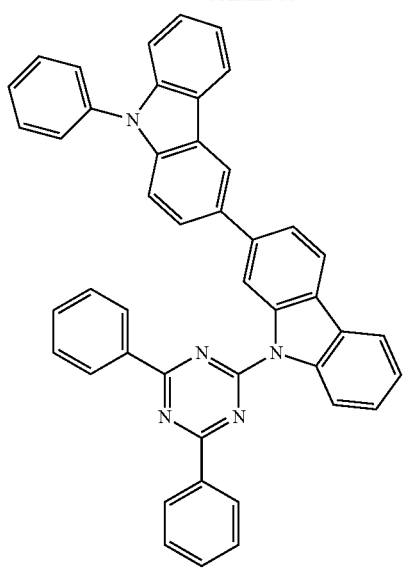
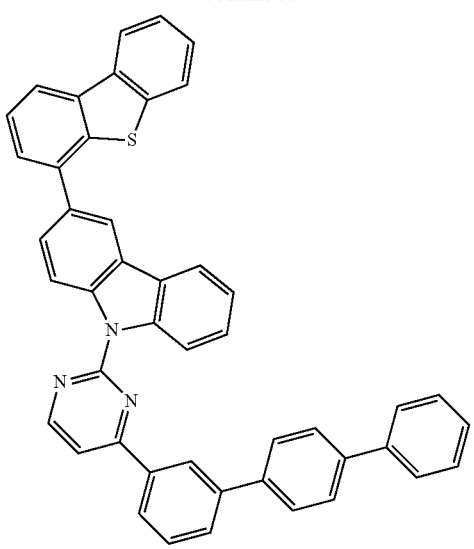
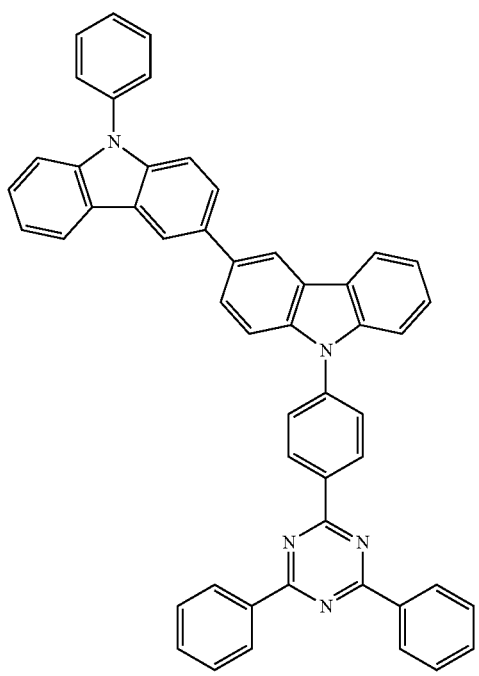
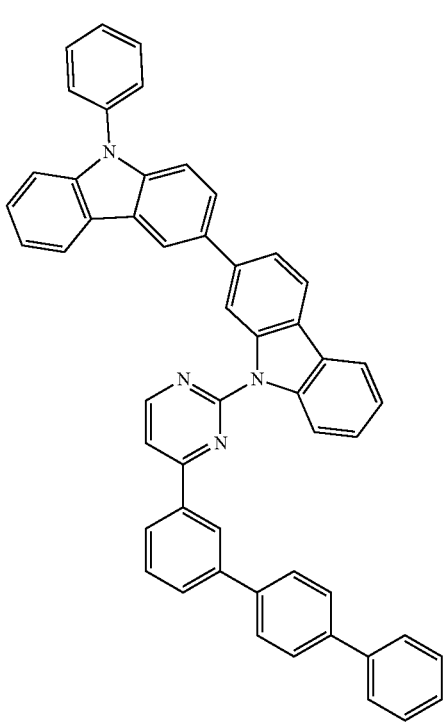

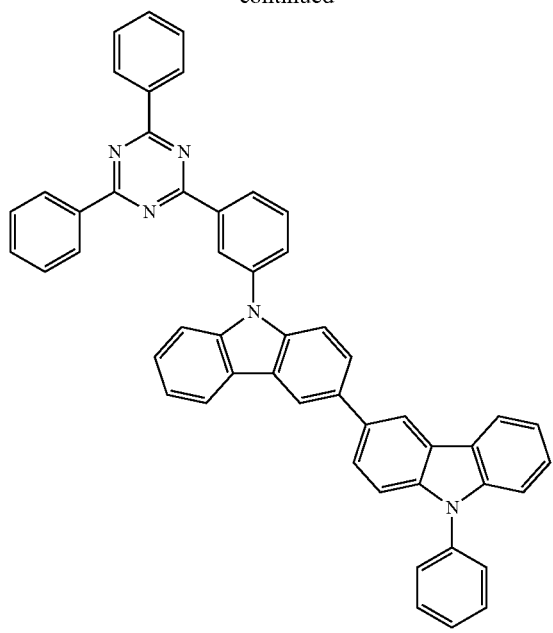
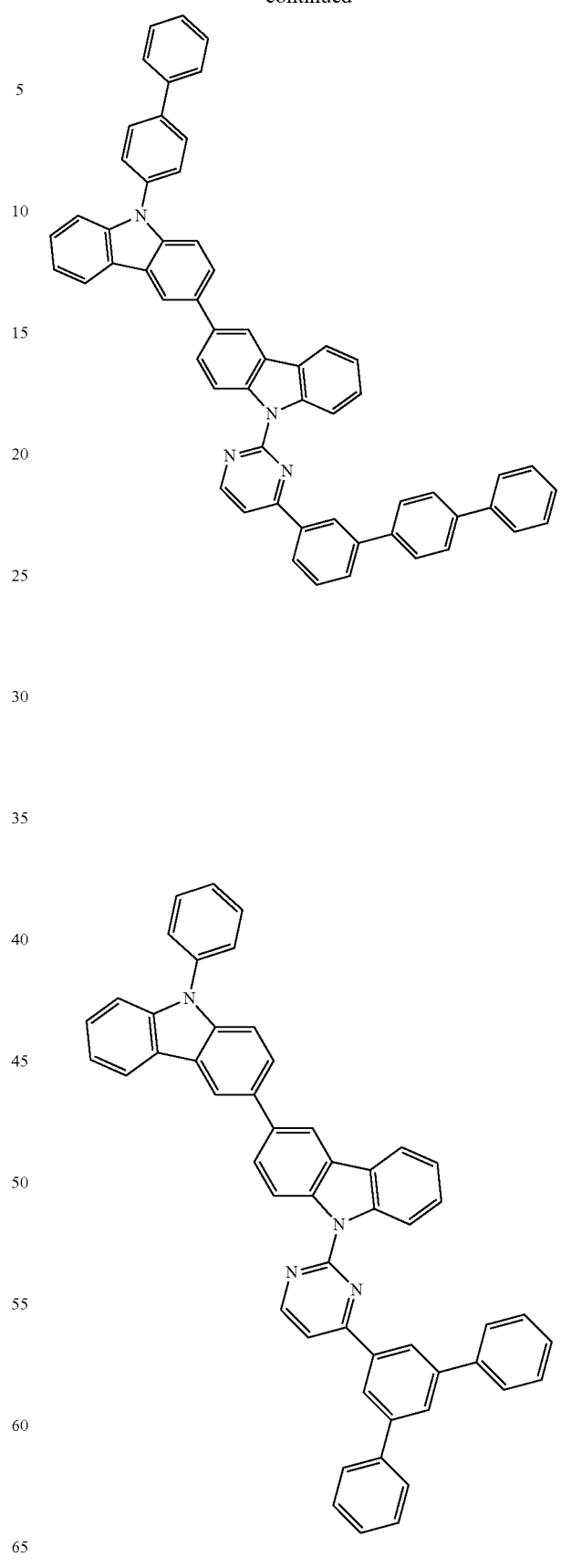

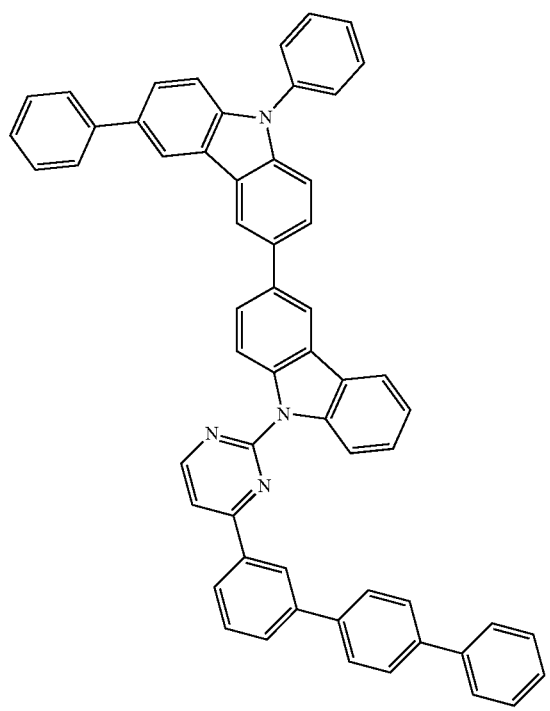
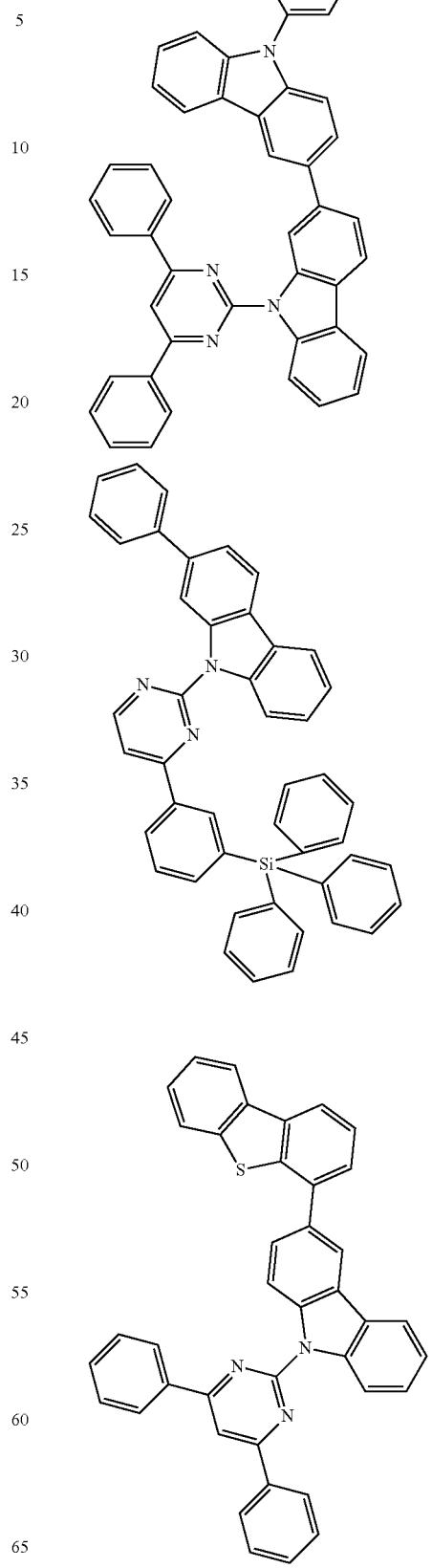

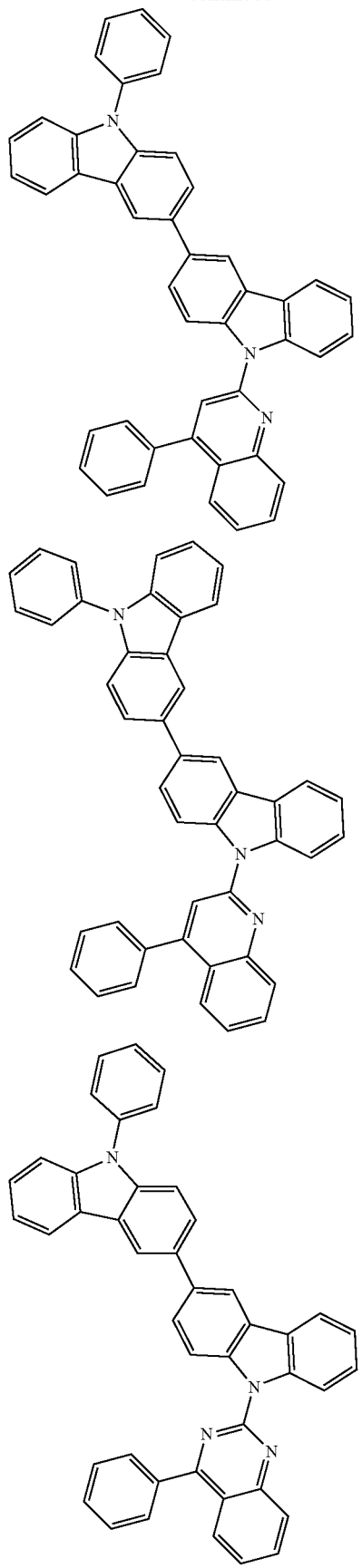
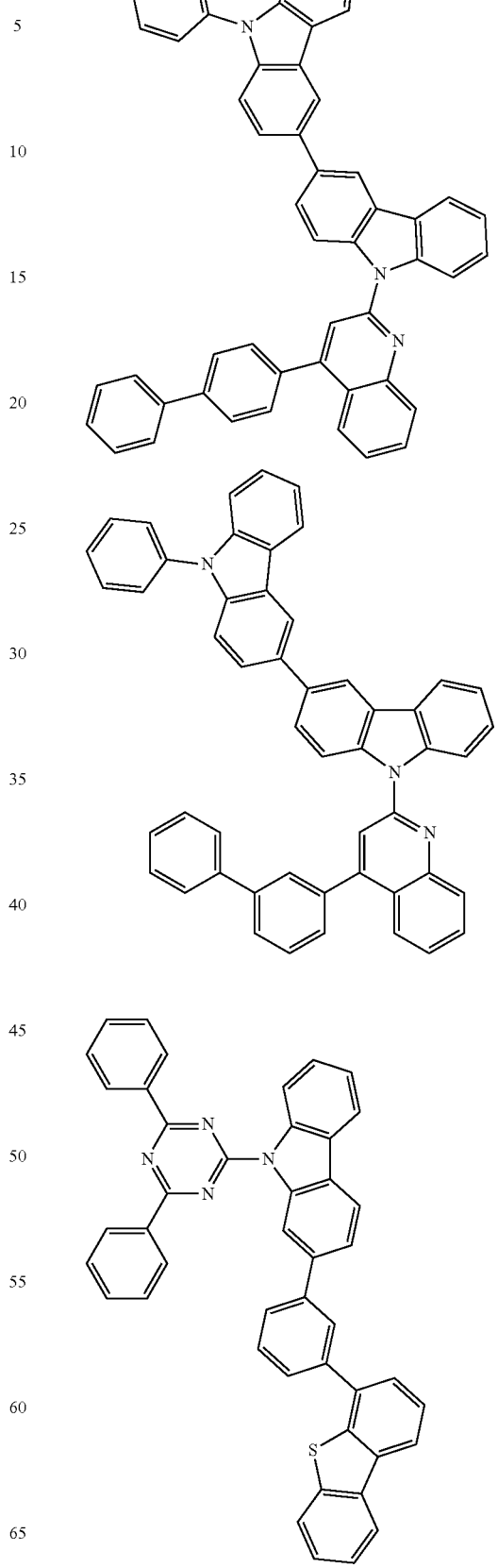

69
-continued
70
-continued
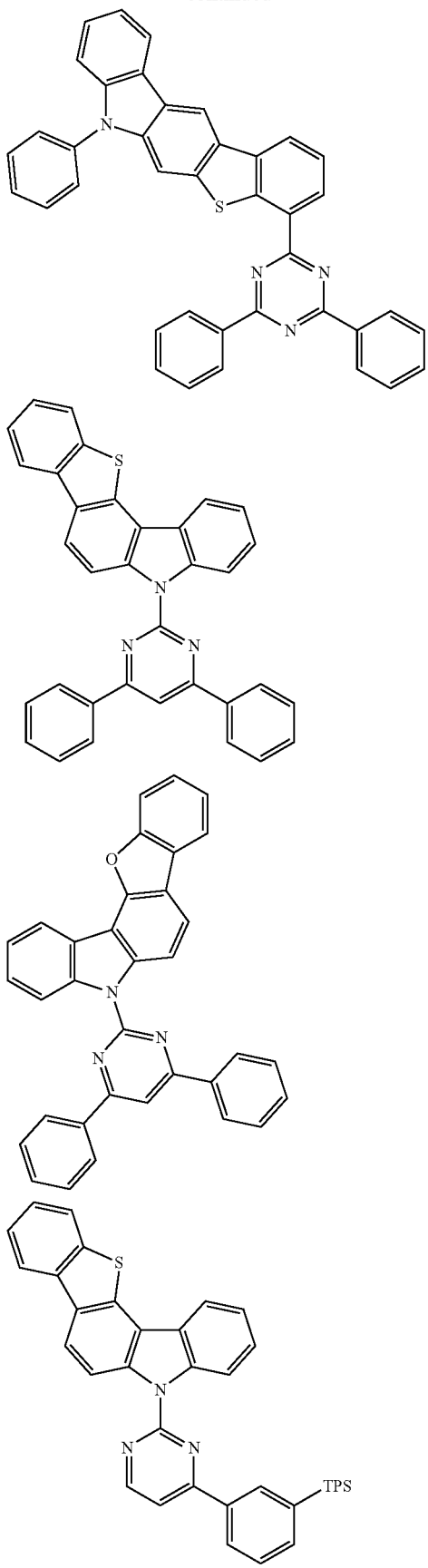
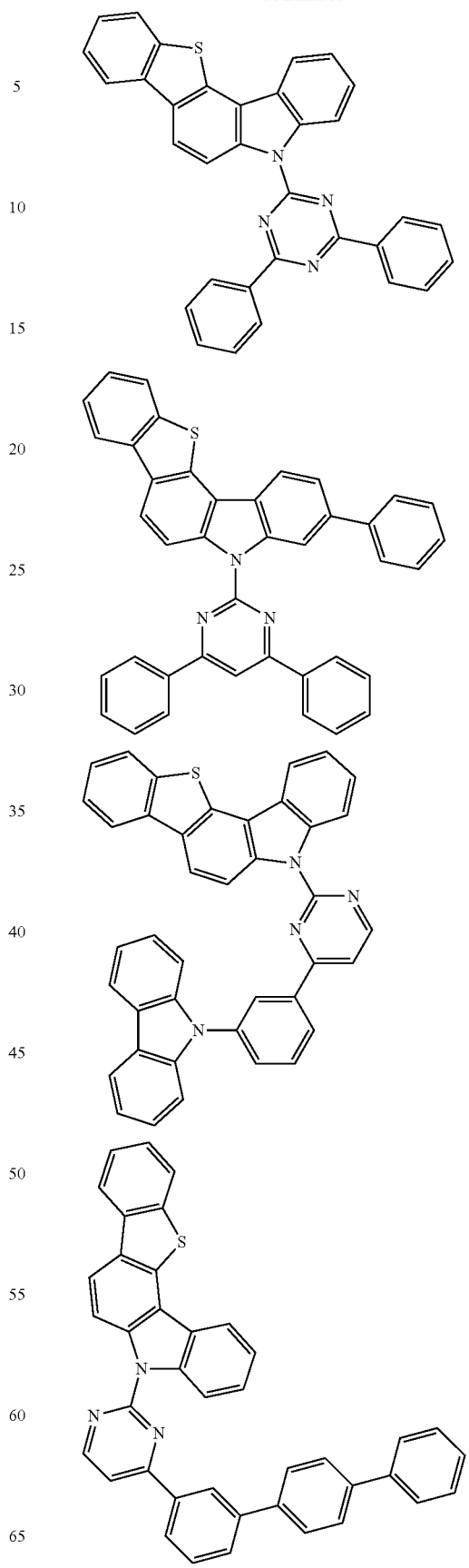

71
-continued
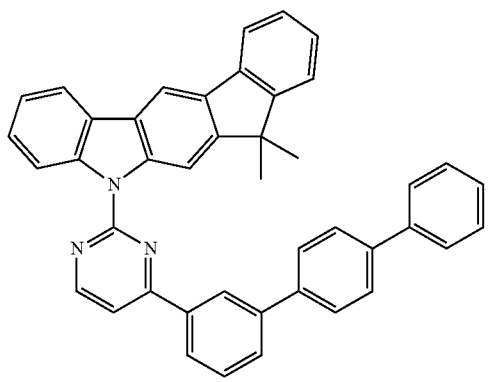
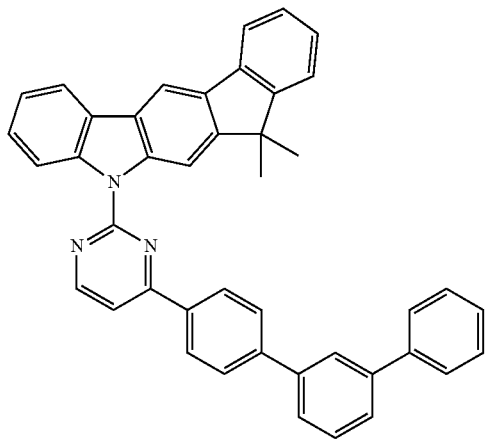
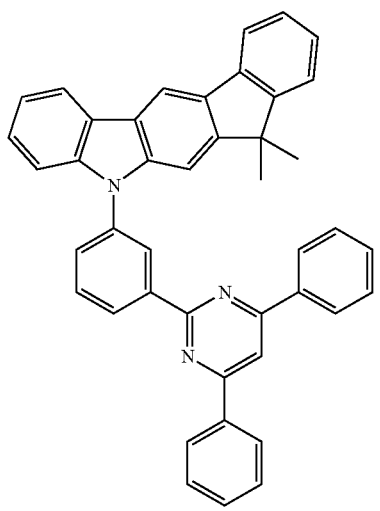
72
-continued
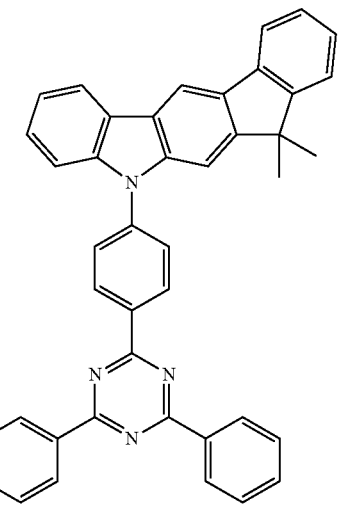
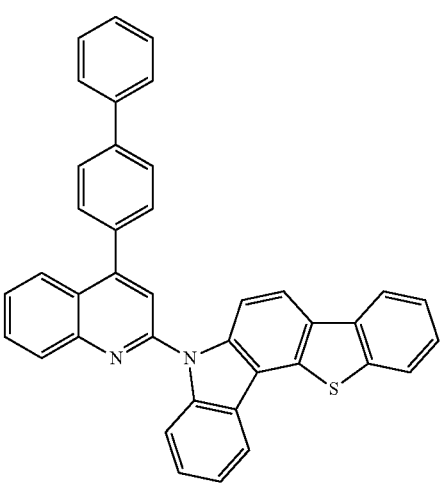
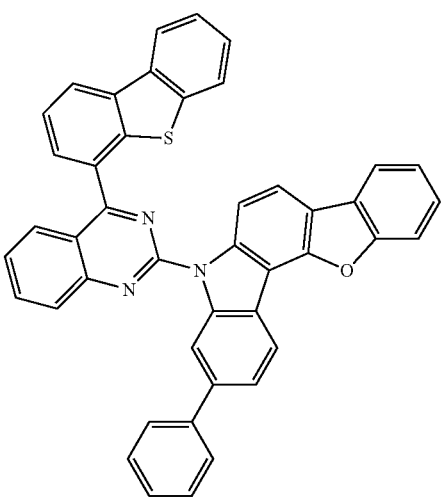

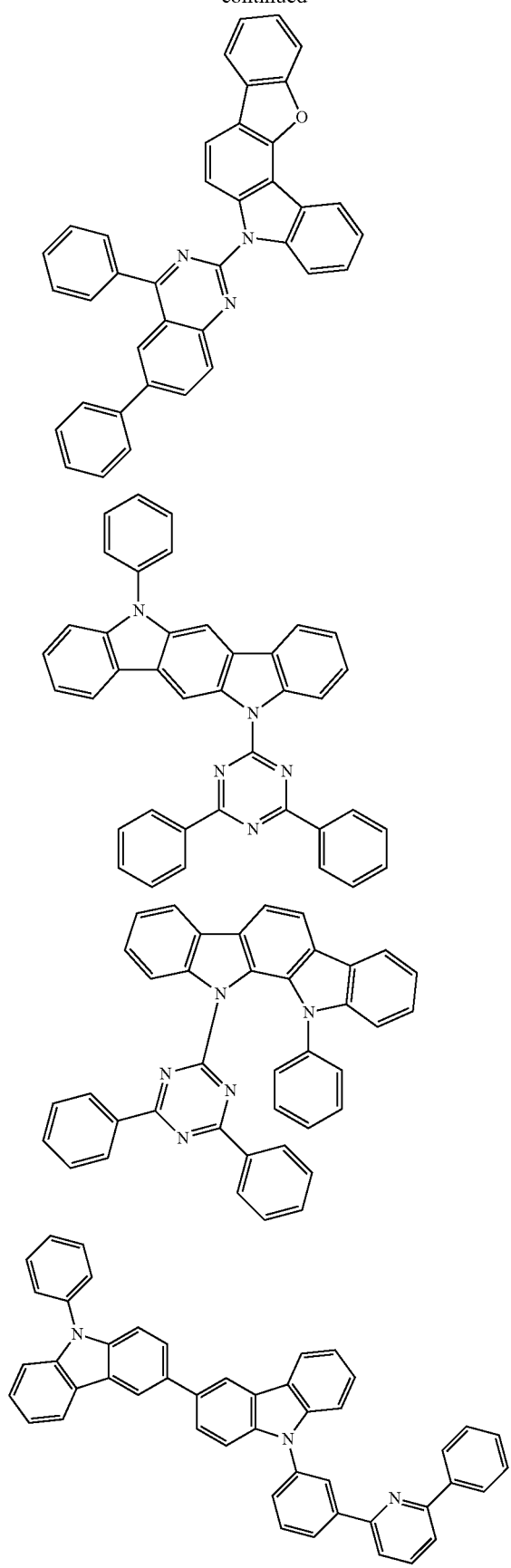
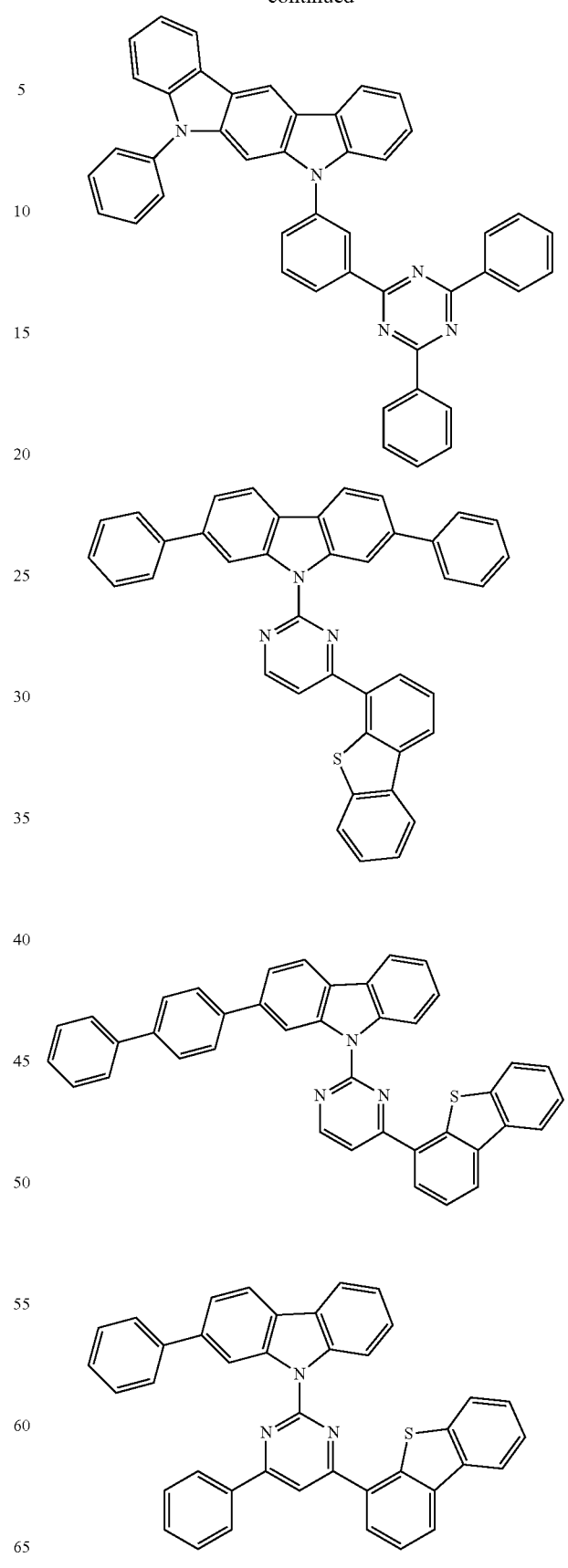

75
-continued
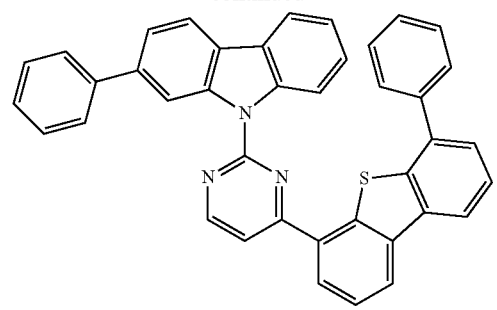
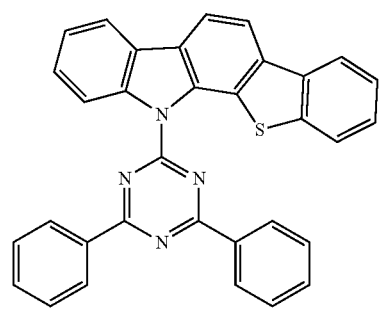
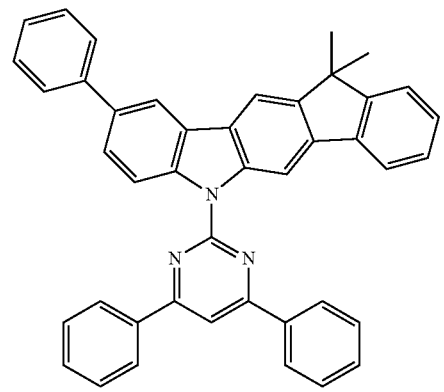
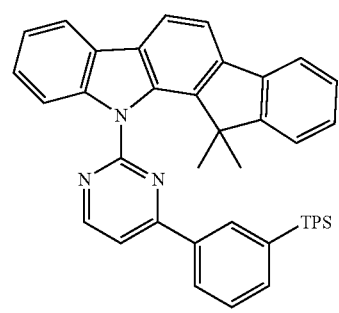
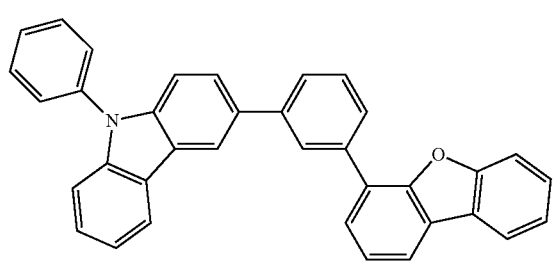
76
-continued
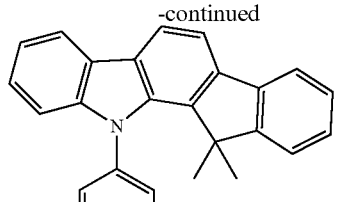
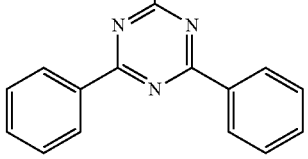
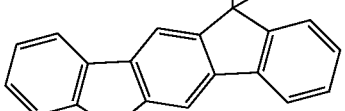
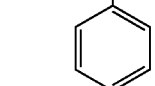
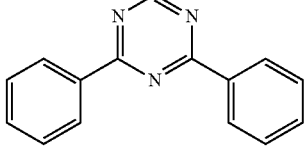
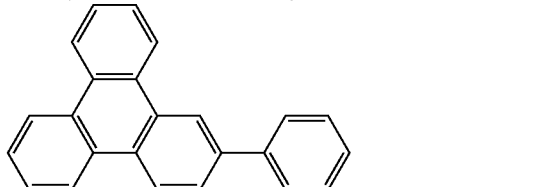
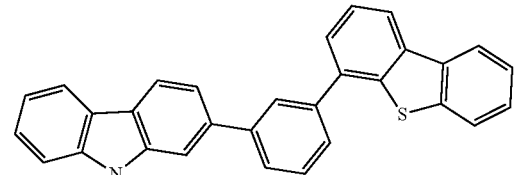
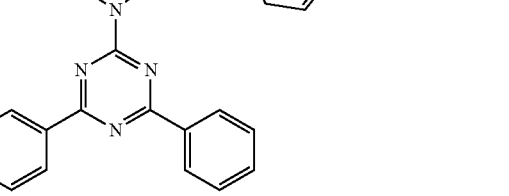
(wherein, TPS represents triphenylsilyl group.)
The dopant is preferably at least one phosphorescent dopant. The phosphorescent dopant material for the organic electroluminescent device of the present disclosure is not limited, but may be preferably selected from metallated complex compounds of iridium (Ir), osmium (Os), copper (Cu) or platinum (Pt), more preferably selected from ortho-metallated complex compounds of iridium (Ir), osmium (Os), copper (Cu) or platinum (Pt), and even more preferably ortho-metallated iridium complex compounds.

Preferably, the phosphorescent dopant may be selected from the group consisting of compounds represented by the following formulae 101 to 103.

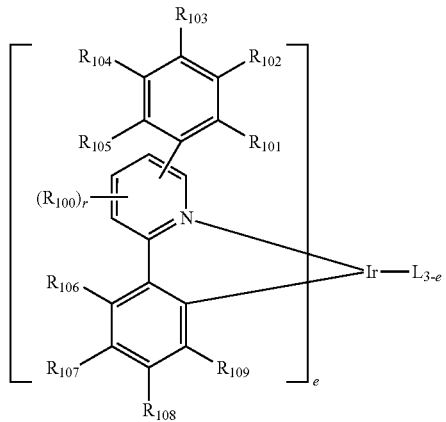

(101)

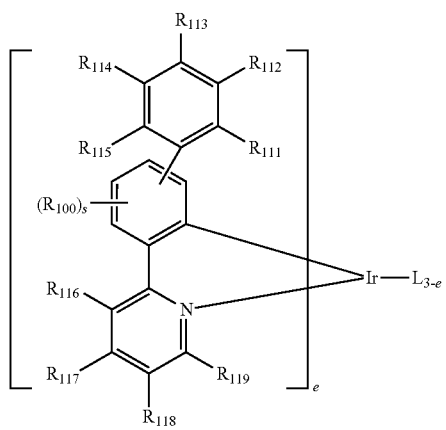

(102)

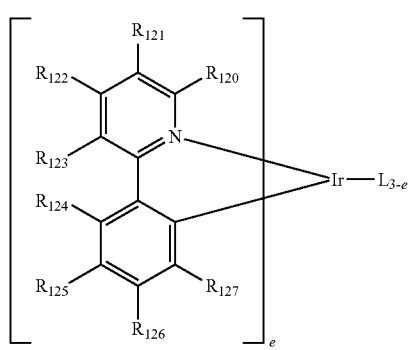

(103)

wherein L is selected from the following structures:

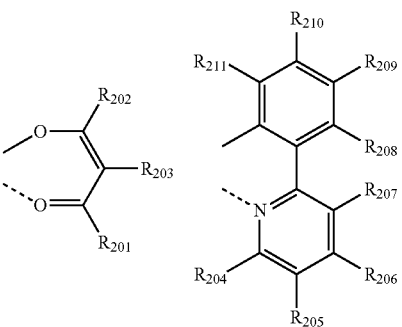

$R_{100}$ represents hydrogen, a substituted or unsubstituted (C1-C30)alkyl, or a substituted or unsubstituted (C3-C30)cycloalkyl; $R_{101}$ to $R_{109}$ and $R_{111}$ to $R_{123}$, each independently, represent hydrogen, deuterium, a halogen, a (C1-C30)alkyl unsubstituted or substituted with a halogen, a substituted or unsubstituted (C3-C30)cycloalkyl, a substituted or unsubstituted (C6-C30)aryl, a cyano, or a substituted or unsubstituted (C1-C30)alkoxy; $R_{106}$ to $R_{109}$ may be linked to an adjacent substituent(s) to form a substituted or unsubstituted fused ring, for example, fluorene unsubstituted or substituted with alkyl, dibenzothiophene unsubstituted or substituted with alkyl, or dibenzofuran unsubstituted or substituted with alkyl; $R_{120}$ to $R_{123}$ may be linked to an adjacent substituent(s) to form a substituted or unsubstituted fused ring, for example, quinoline unsubstituted or substituted with alkyl or aryl; $R_{124}$ to $R_{127}$, each independently, represent hydrogen, deuterium, a halogen, a substituted or unsubstituted (C1-C30)alkyl, or a substituted or unsubstituted (C6-C30)aryl; $R_{124}$ to $R_{127}$ may be linked to an adjacent substituent(s) to form a substituted or unsubstituted fused ring, for example, fluorene unsubstituted or substituted with alkyl, dibenzothiophene unsubstituted or substituted with alkyl, or dibenzofuran unsubstituted or substituted with alkyl; $R_{201}$ to $R_{211}$, each independently, represent hydrogen, deuterium, a halogen, a (C1-C30)alkyl unsubstituted or substituted with a halogen, a substituted or unsubstituted (C3-C30)cycloalkyl, or a substituted or unsubstituted (C6-C30)aryl; $R_{208}$ to $R_{211}$ may be linked to an adjacent substituent(s) to form a substituted or unsubstituted fused ring, for example, fluorene unsubstituted or substituted with alkyl, dibenzothiophene unsubstituted or substituted with alkyl or dibenzofuran unsubstituted or substituted with alkyl; r and s, each independently, represent an integer of 1 to 3; where r or s is an integer of 2 or more, each of $R_{100}$ may be the same or different; and e represents an integer of 1 to 3.

Specifically, the phosphorous dopant material includes the following, but is not limited thereto.

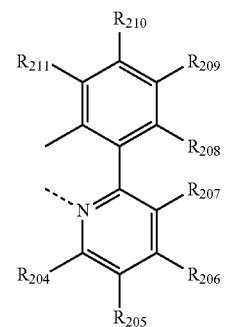

D-1

-continued
D-2
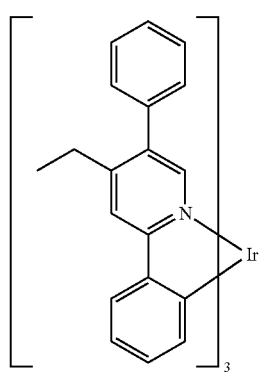
D-3
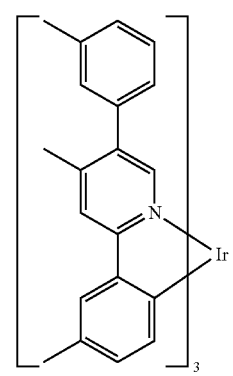
D-4
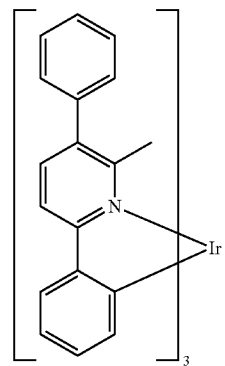
D-5
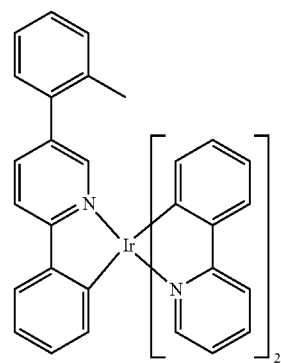
D-6
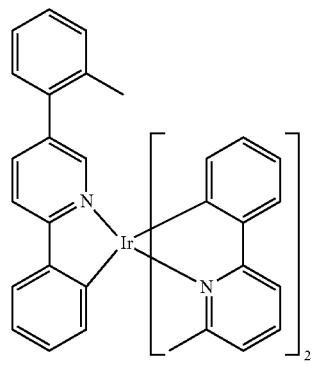
D-7
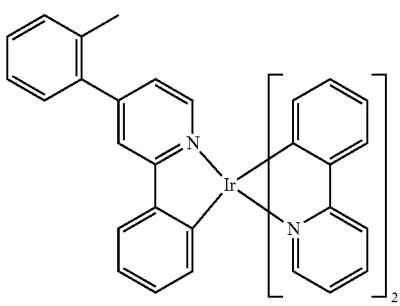
D-8
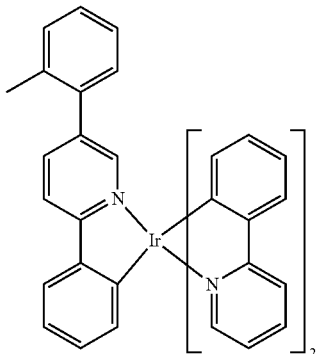
D-9
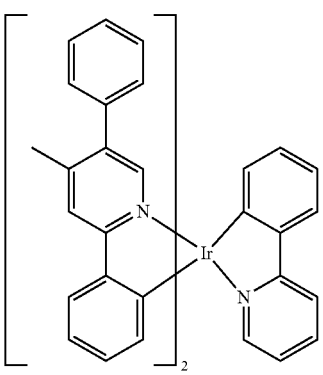

-continued
D-10
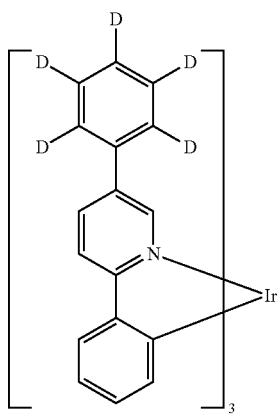
D-11
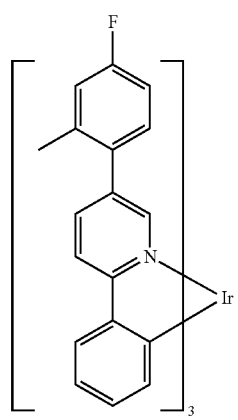
D-12
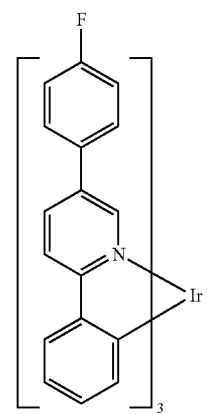
D-13
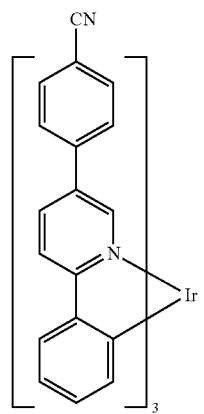
-continued
D-14
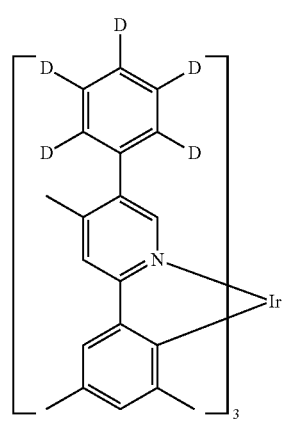
D-15
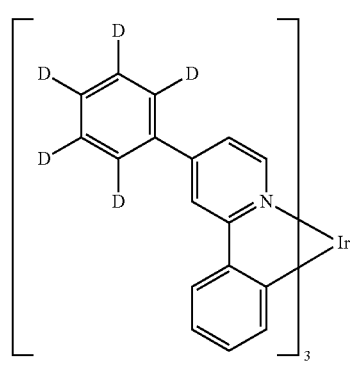
D-16
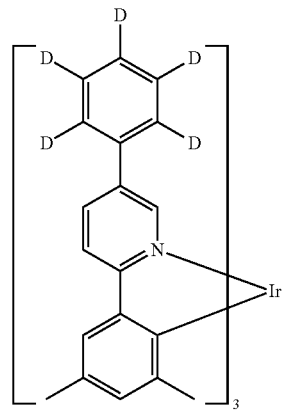
D-17
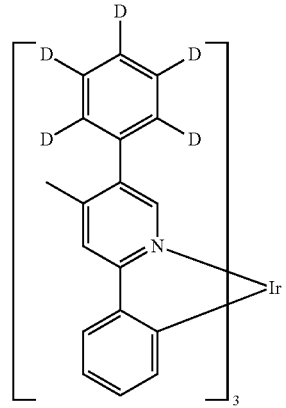

D-18
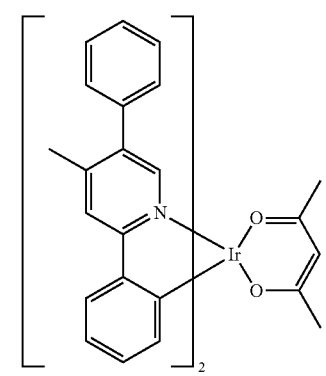
D-19
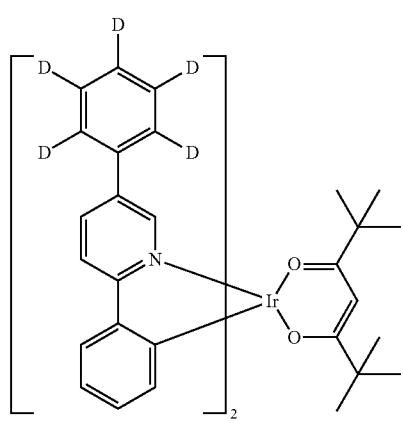
D-20
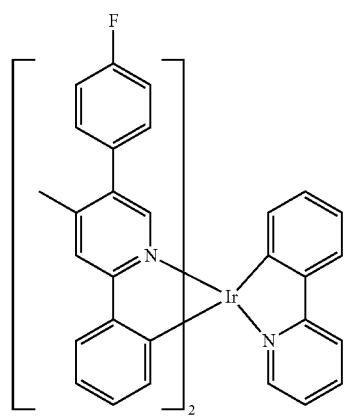
D-21
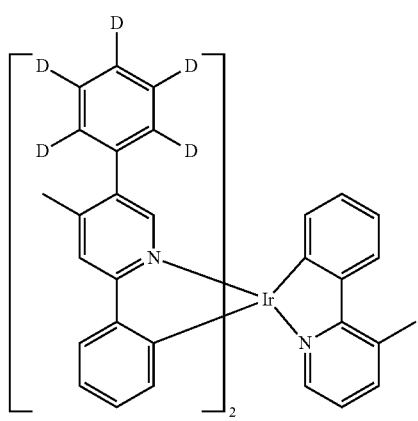
D-22
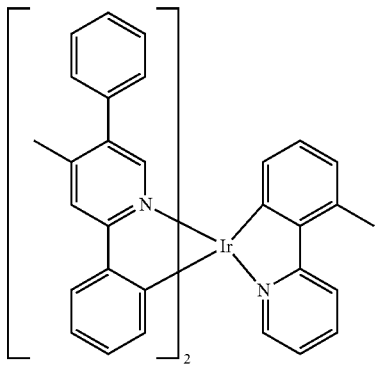
D-23
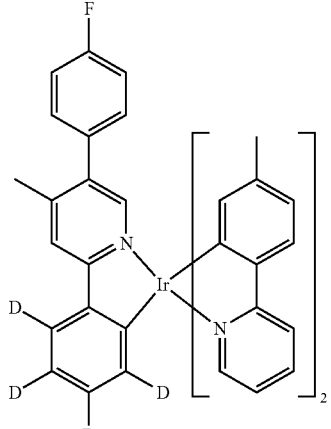
D-24
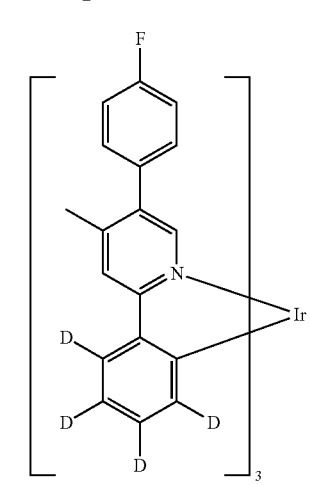
D-25
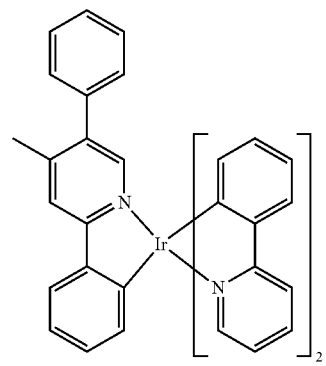

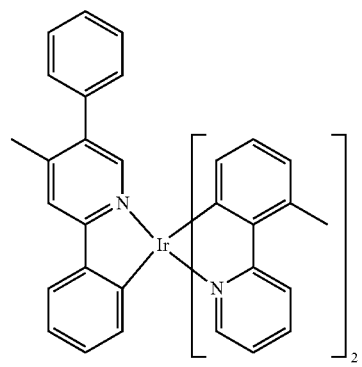
D-26
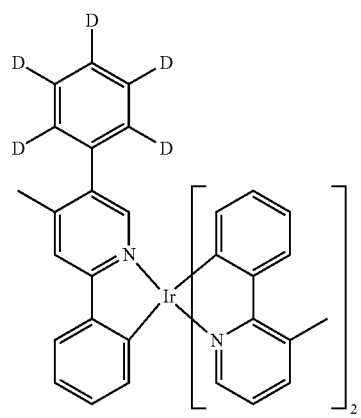
D-27
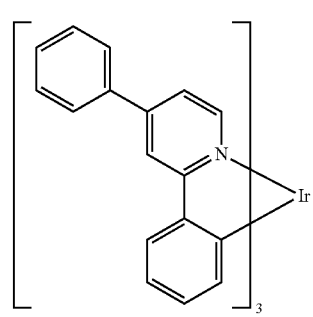
D-28
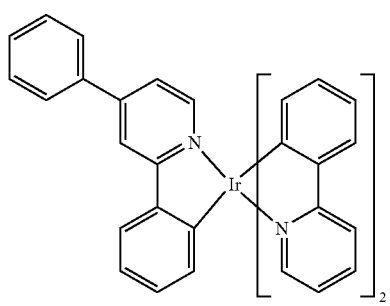
D-29
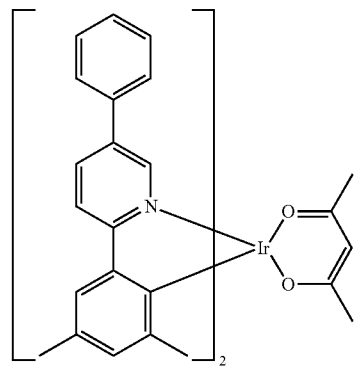
D-30
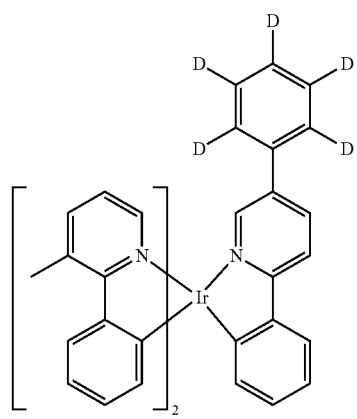
D-31
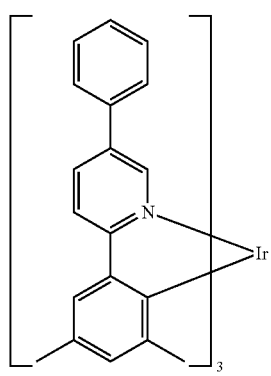
D-32
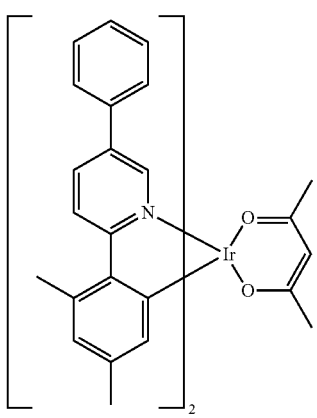
D-33

-continued
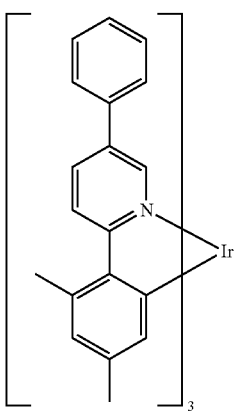 D-34
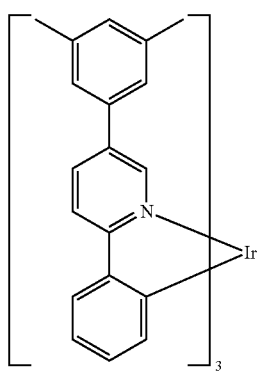 D-35
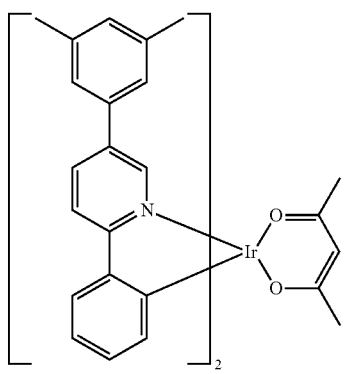 D-36
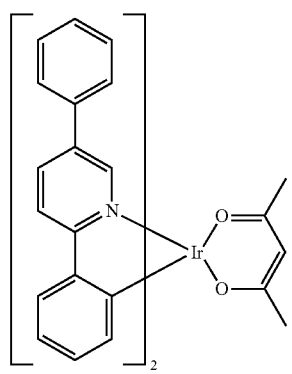 D-37
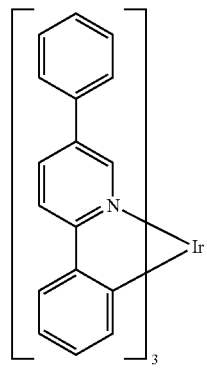 D-38
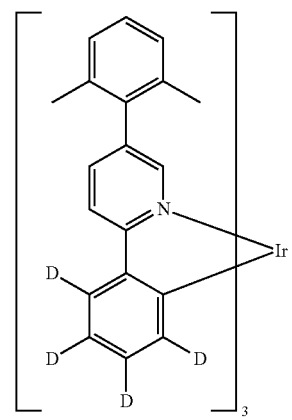 D-39
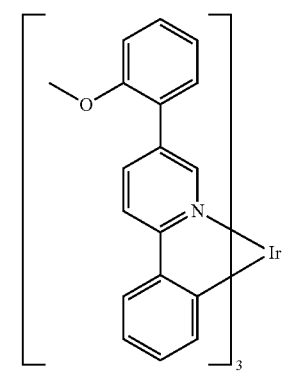 D-40
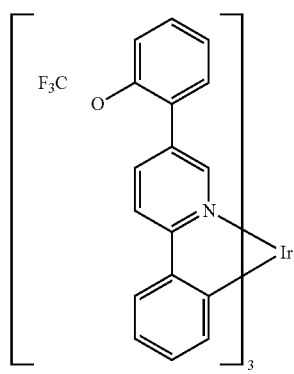 D-41

-continued
D-42
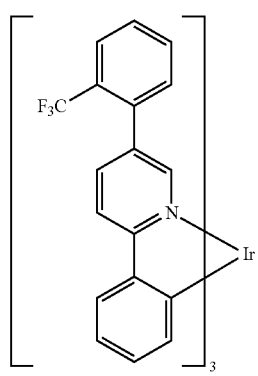
D-43
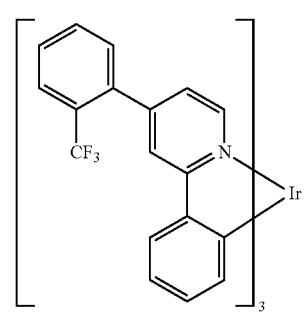
D-44
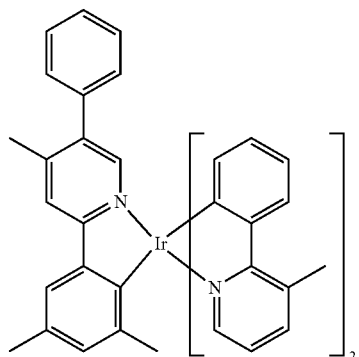
D-45
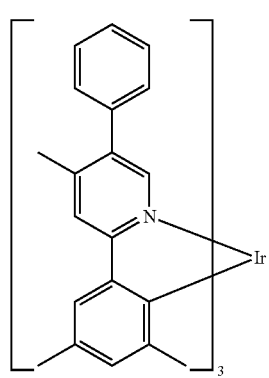
-continued
D-46
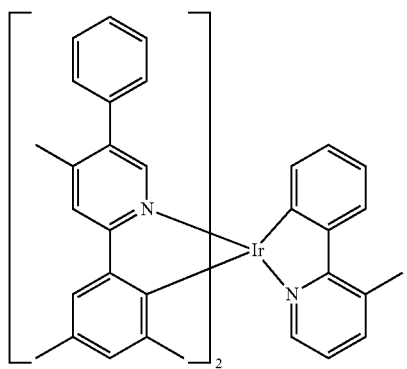
D-47
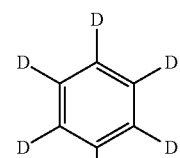
D-48
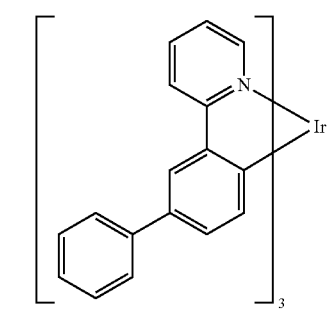
D-49
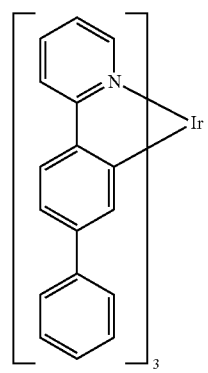

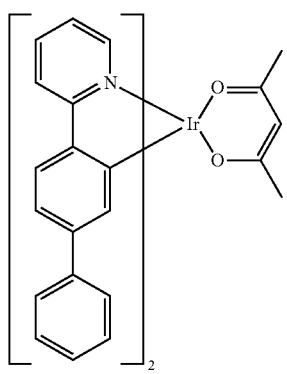
D-50
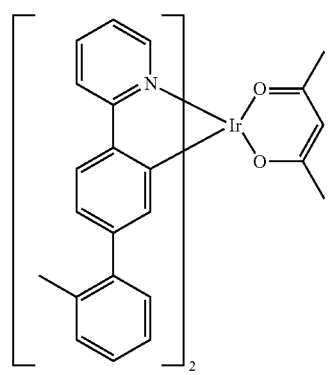
D-51
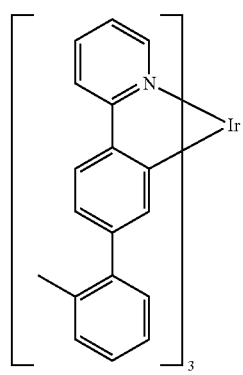
D-52
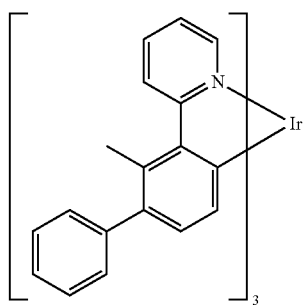
D-53
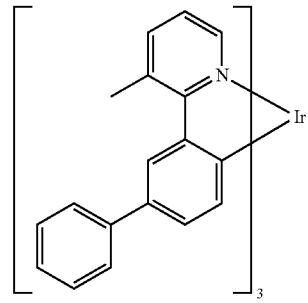
D-54
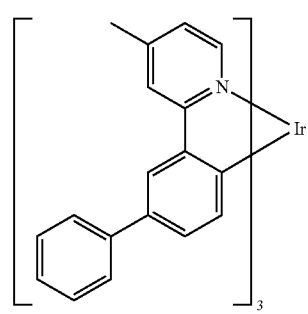
D-55
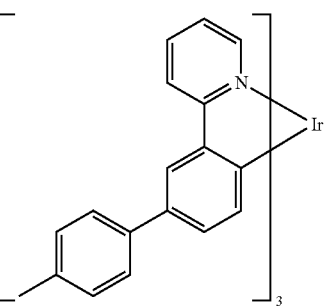
D-56
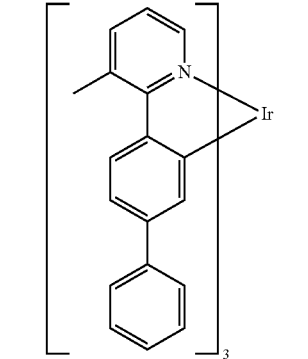
D-57
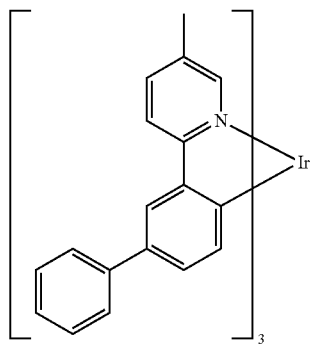
D-58

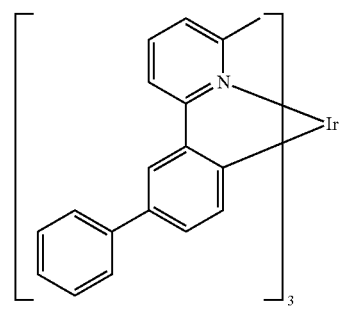
D-59
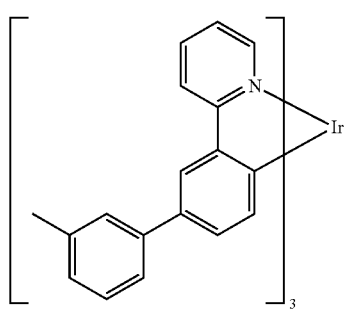
D-60
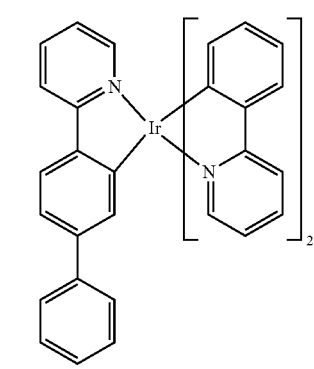
D-61
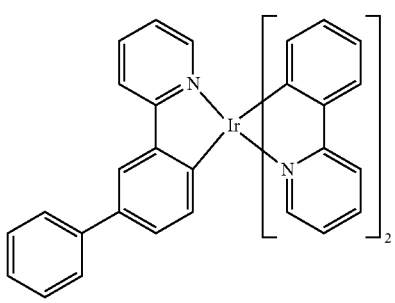
D-62
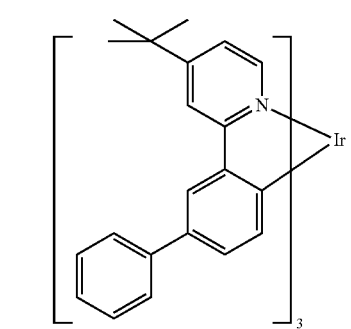
D-63
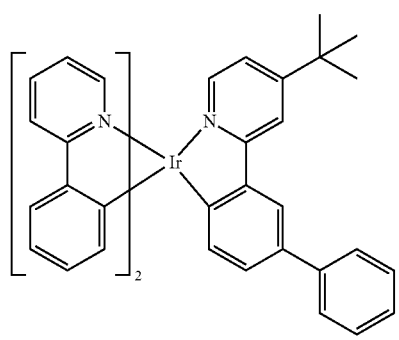
D-64
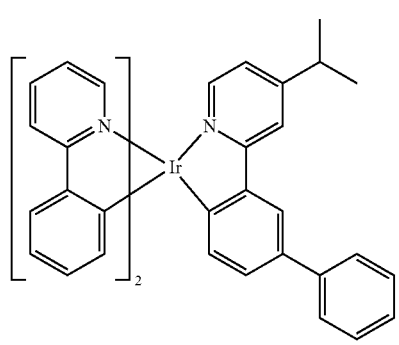
D-65
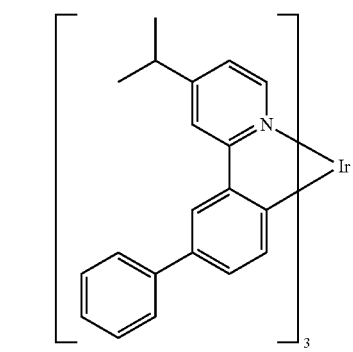
D-66
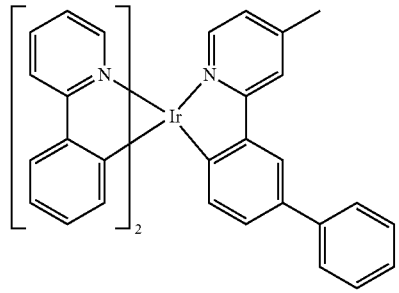
D-67

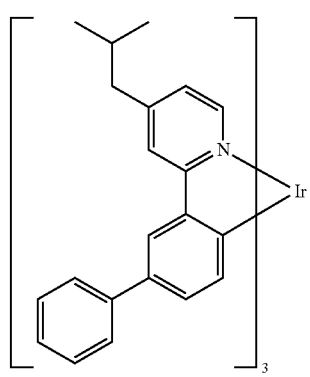
D-68
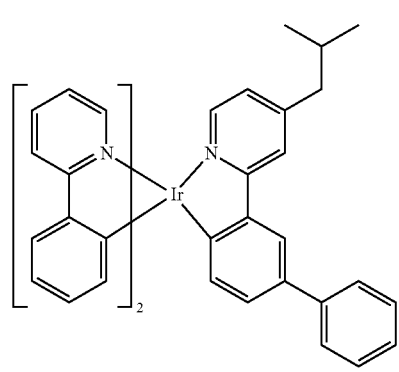
D-69
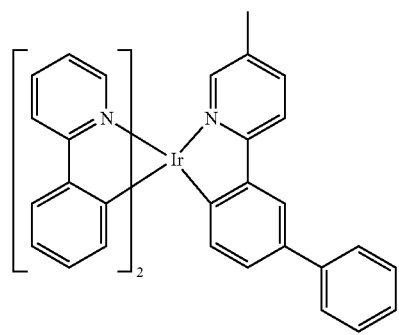
D-70
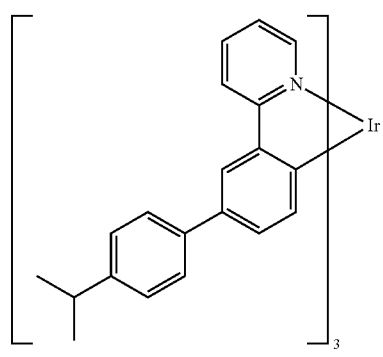
D-71
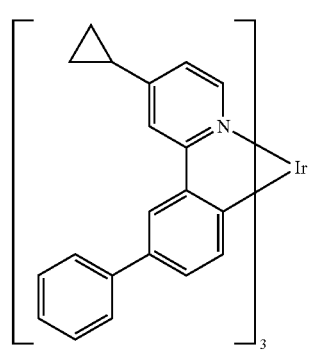
D-72
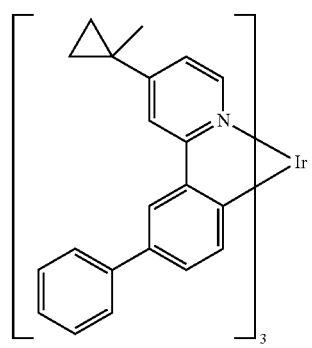
D-73
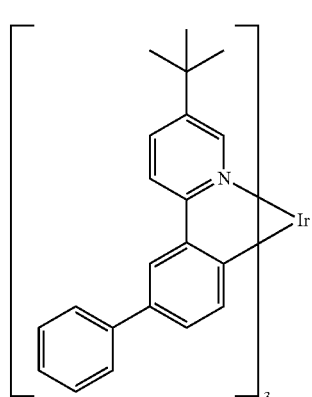
D-74
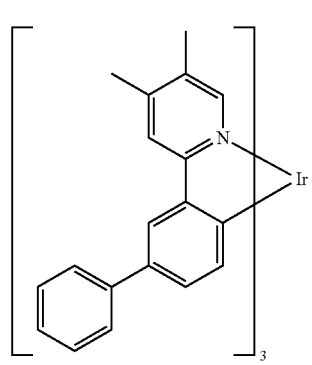
D-75

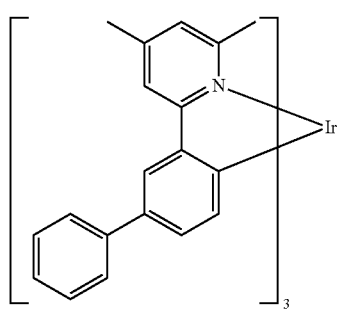
D-76
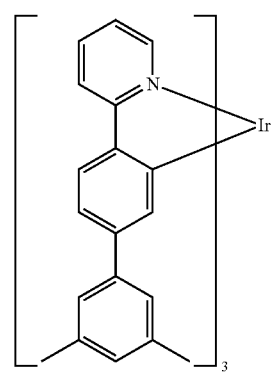
D-77
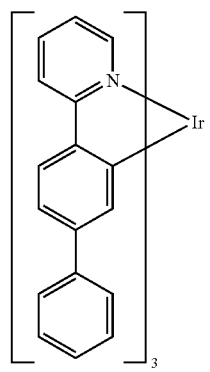
D-78
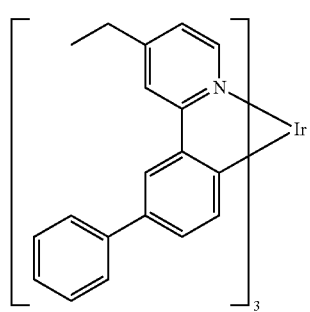
D-79
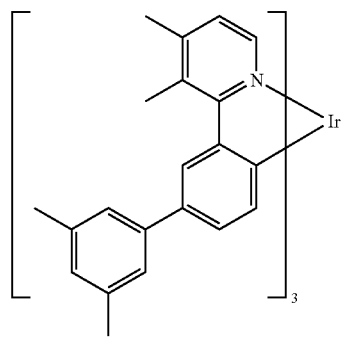
D-80
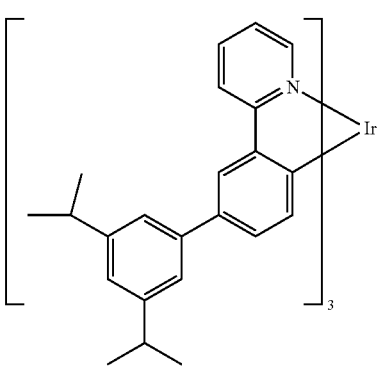
D-81
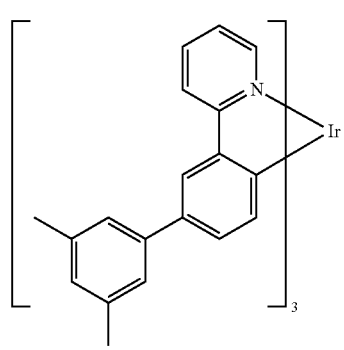
D-82
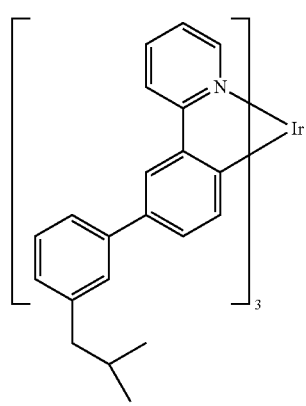
D-83

D-84
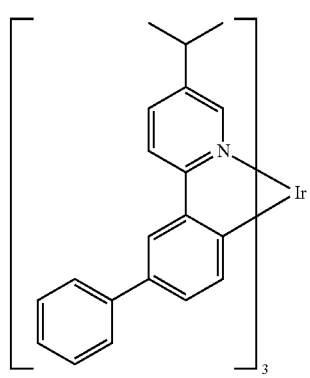
D-88
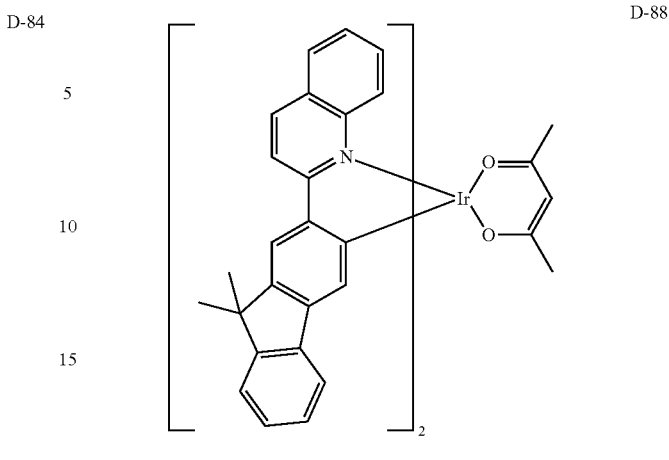
D-85
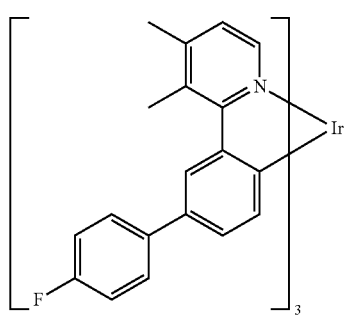
D-89
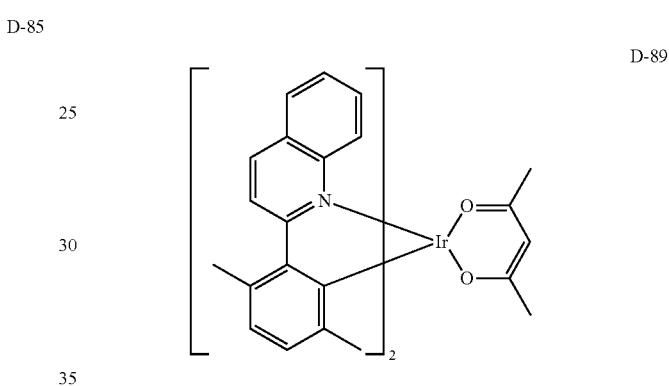
D-86
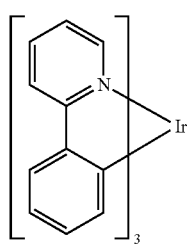
D-90
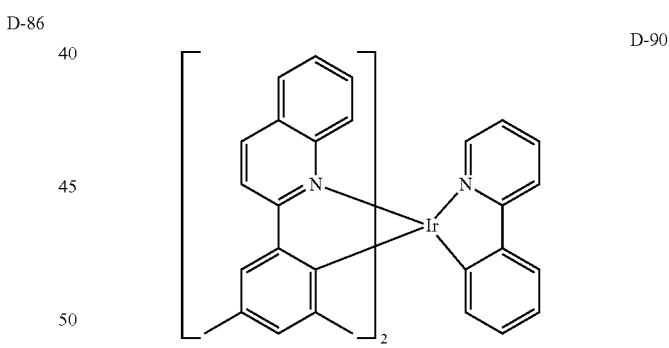
D-87
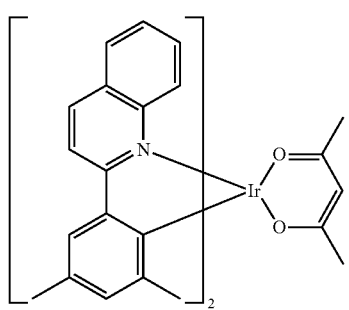
D-91
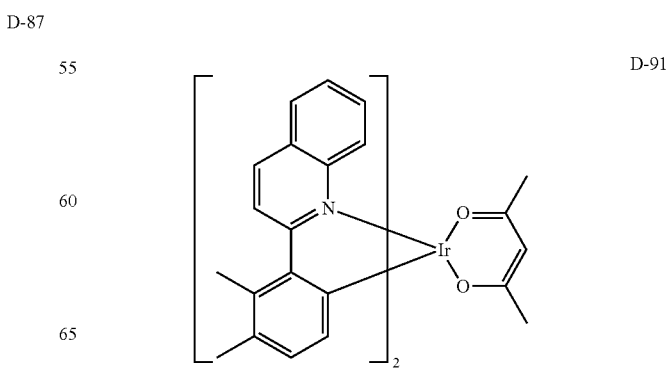

-continued
D-92
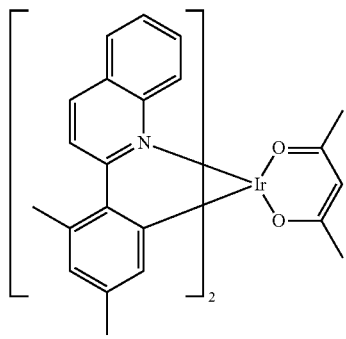
D-93
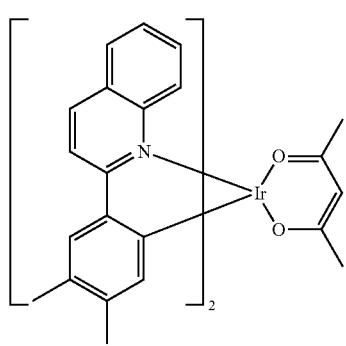
D-94
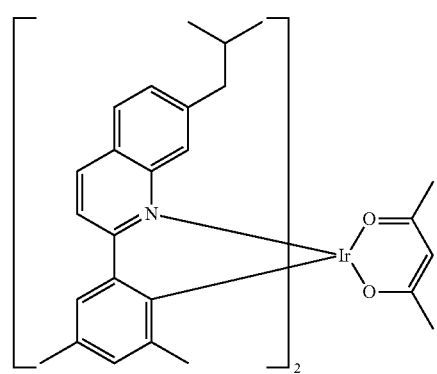
D-95
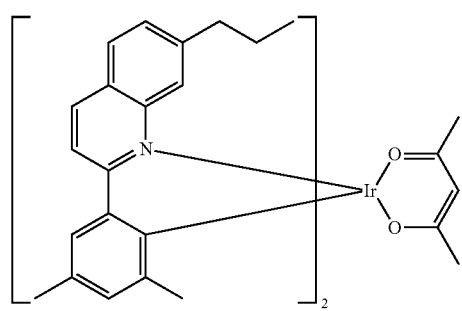
-continued
D-96
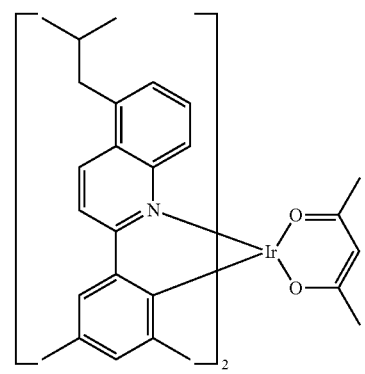
D-97
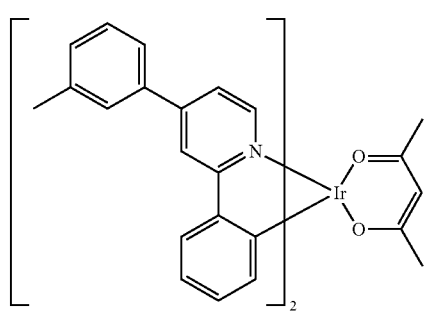
D-98
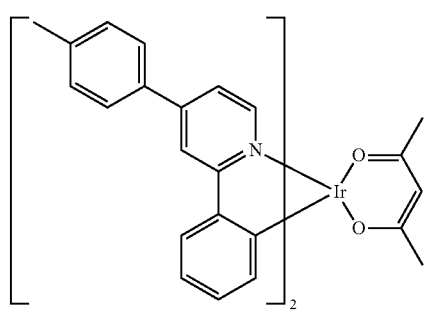
D-99
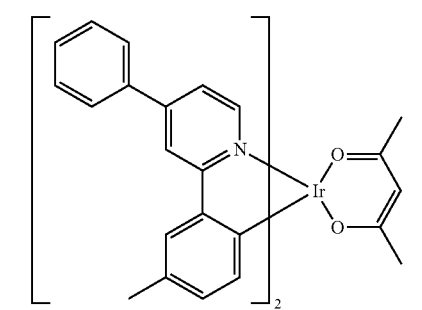
D-100
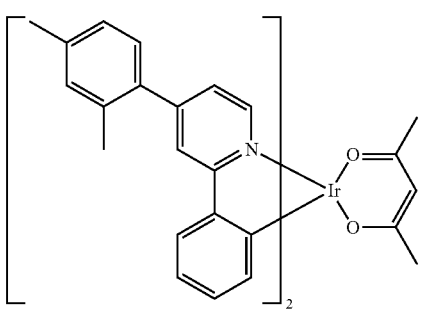

D-101
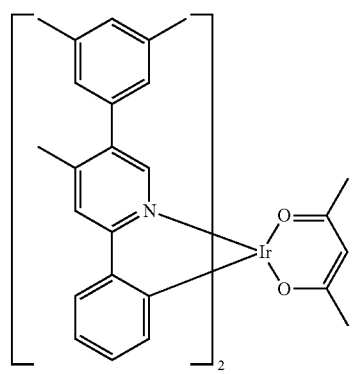
D-102
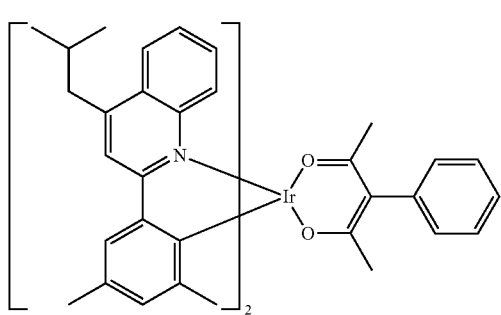
D-103
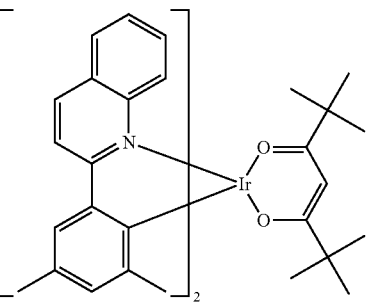
D-104
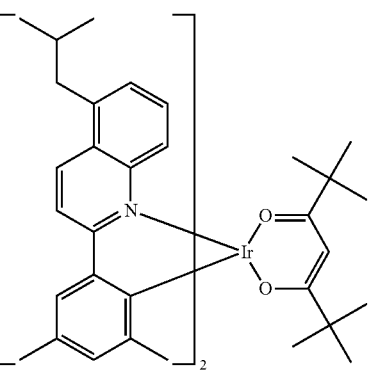
D-105
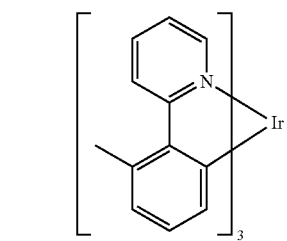
D-106
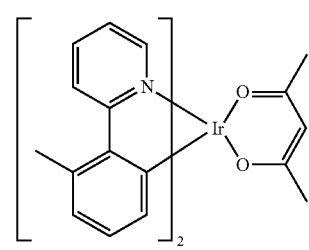
D-107
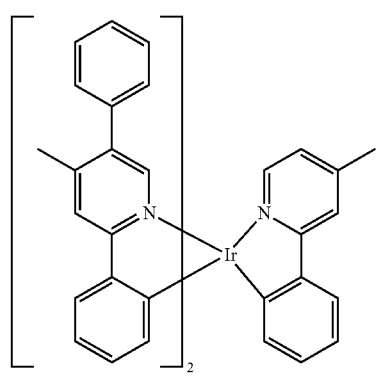
D-108
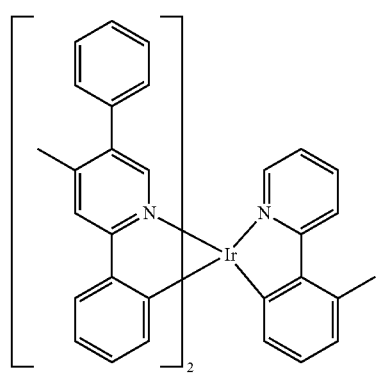
D-109
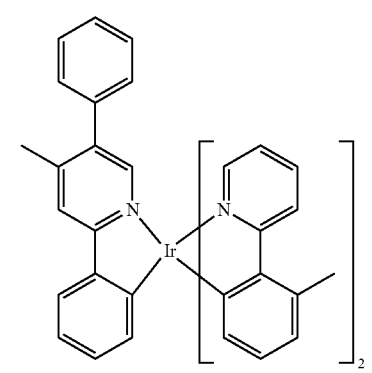
D-110
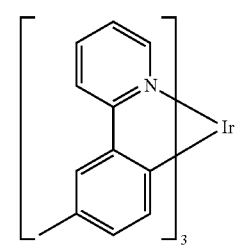

D-111
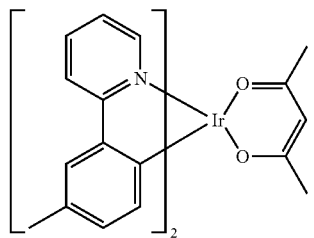
D-112
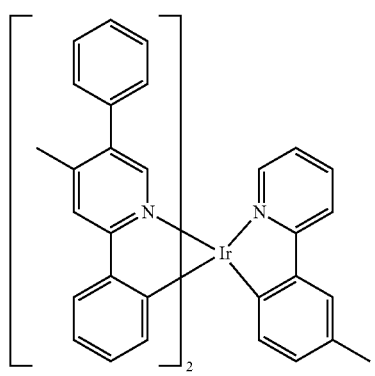
D-113
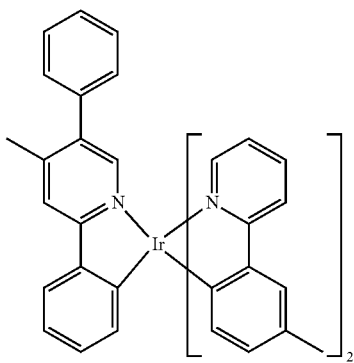
D-114
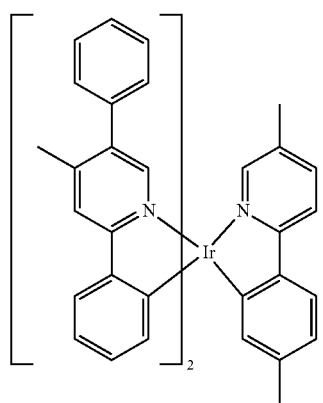
D-115
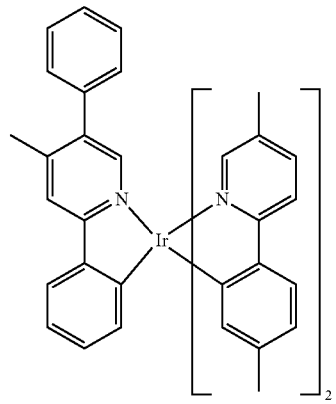
D-116
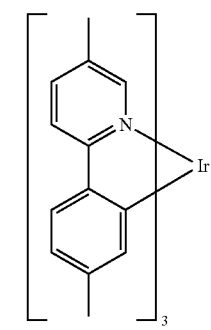
D-117
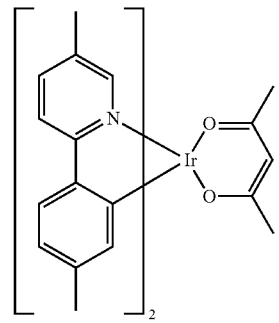
D-118
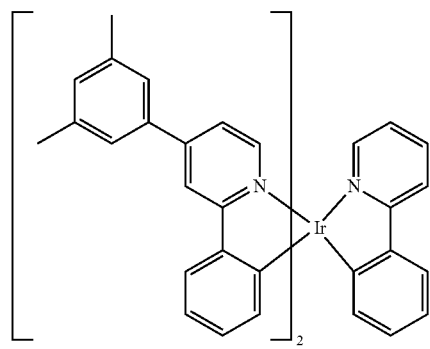

-continued
D-119
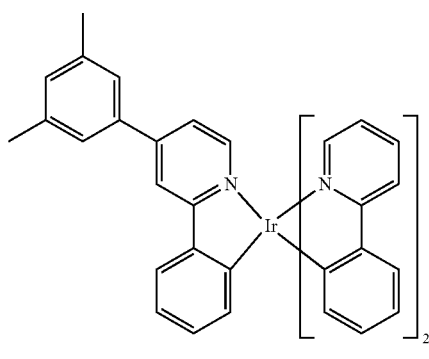
D-120
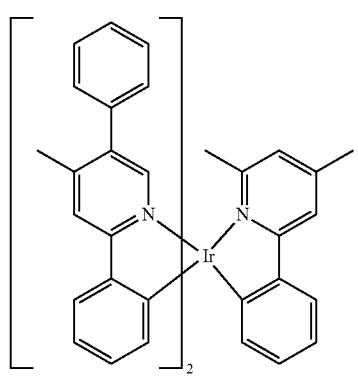
D-121
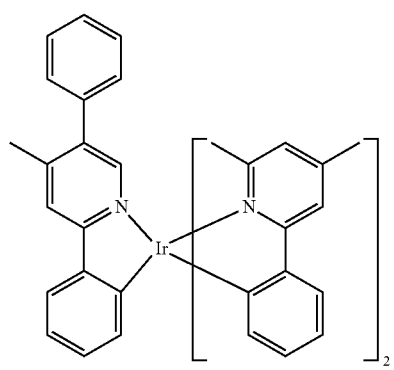
D-122
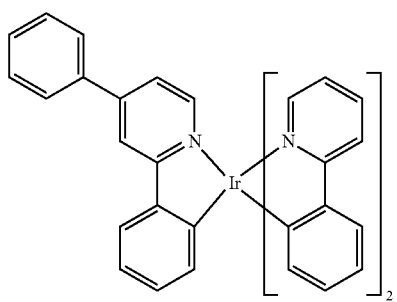
-continued
D-123
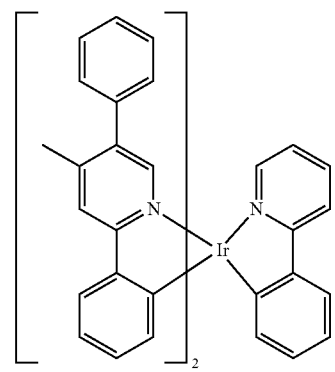
D-124
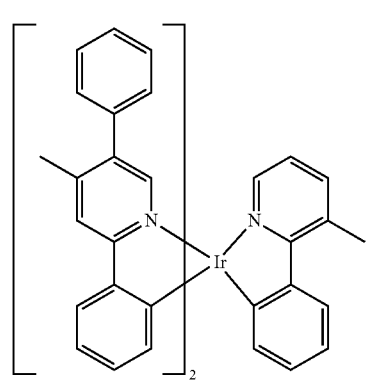
D-125
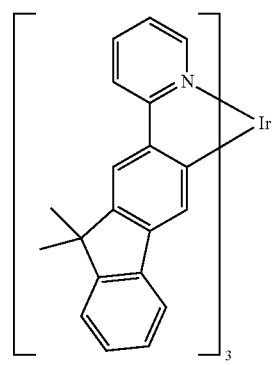
D-126
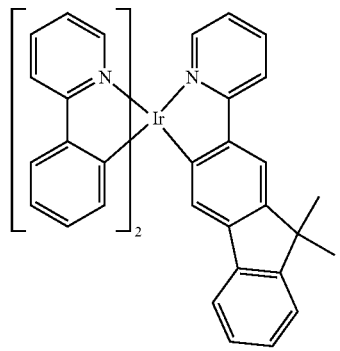

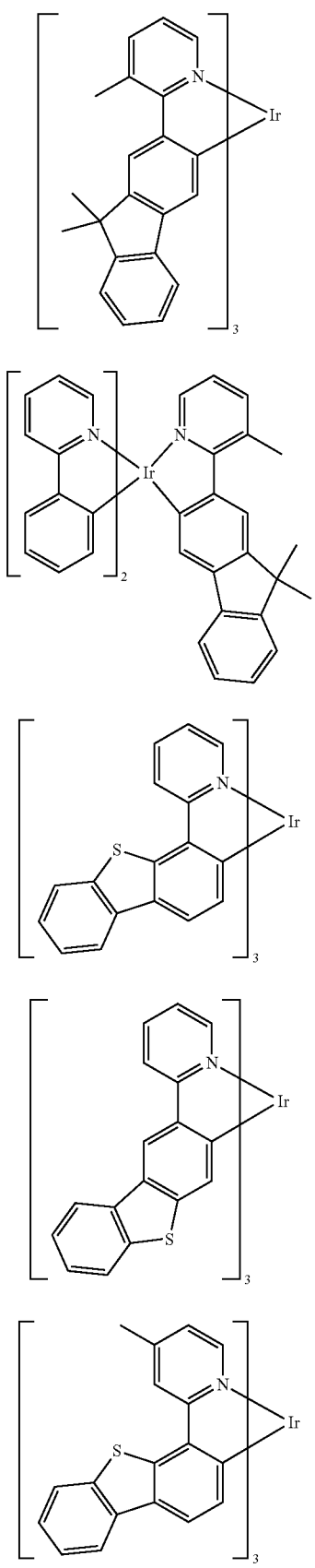

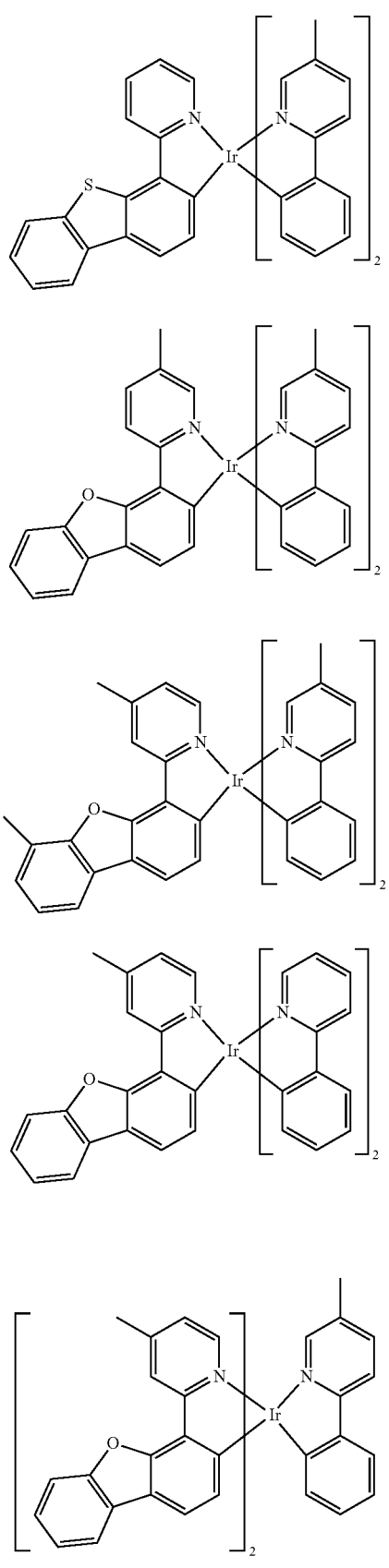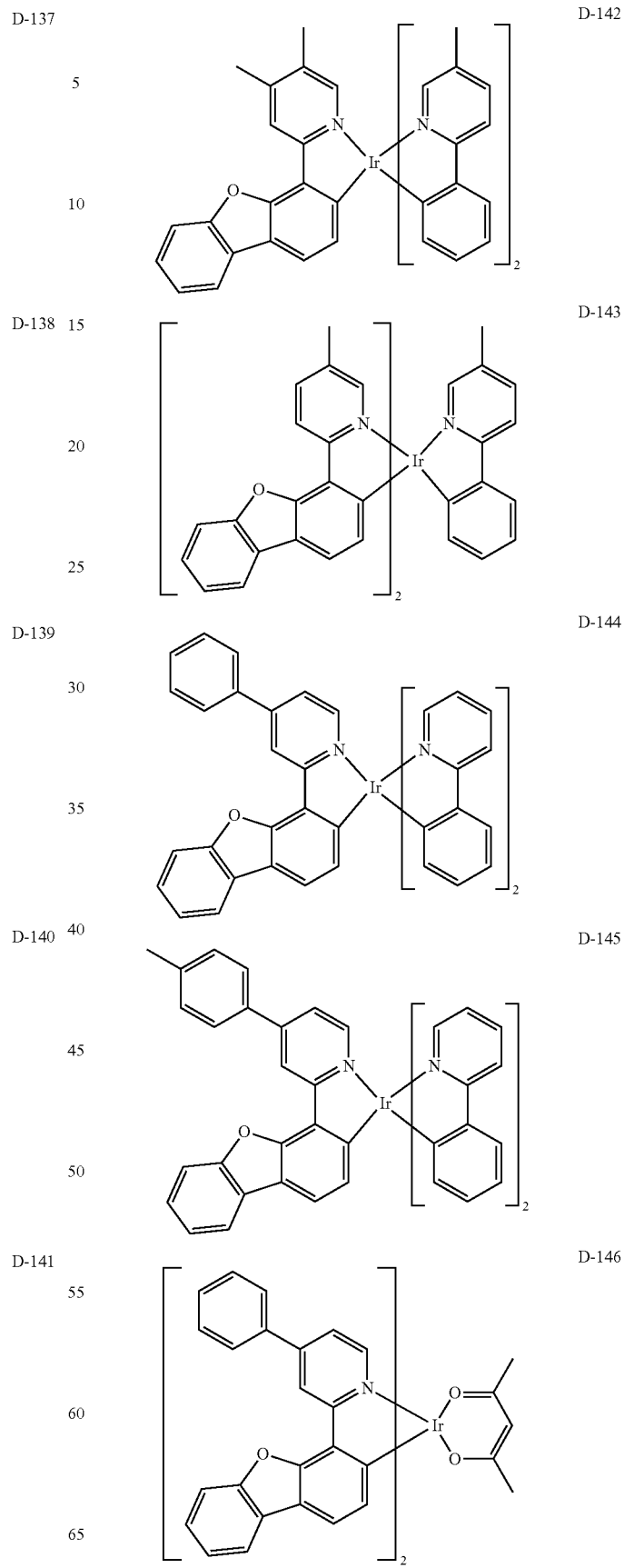

D-147
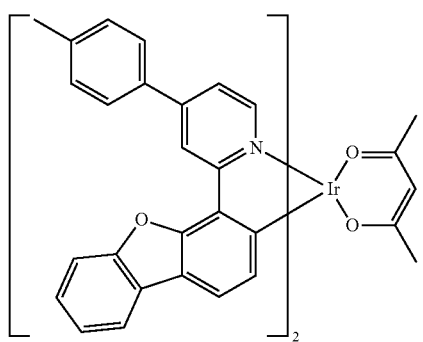
D-148
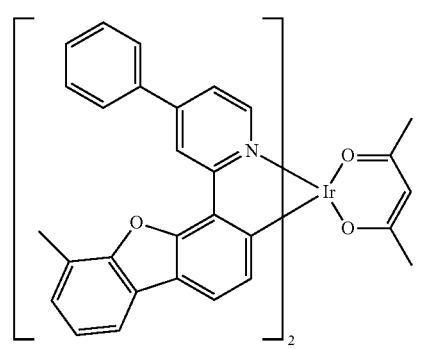
D-149
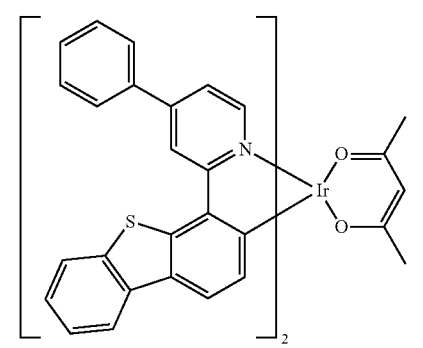
D-150
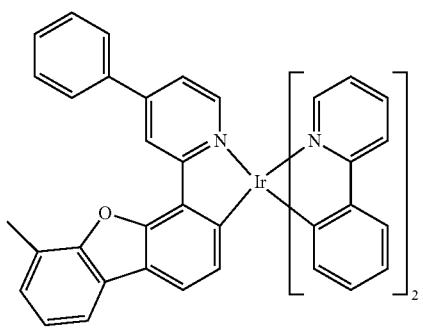
D-151
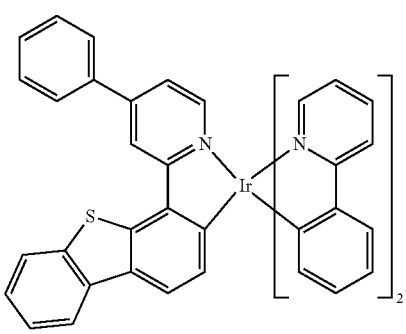
D-152
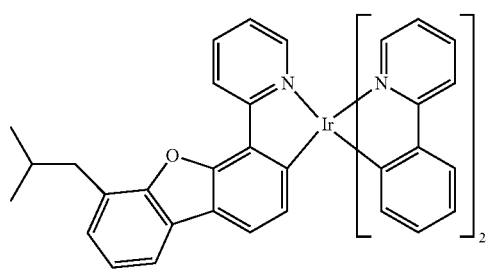
D-153
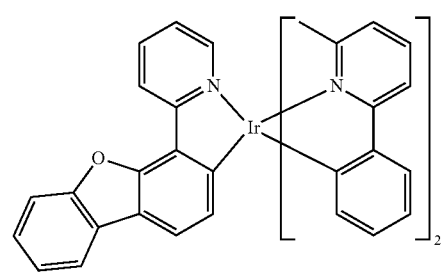
D-154
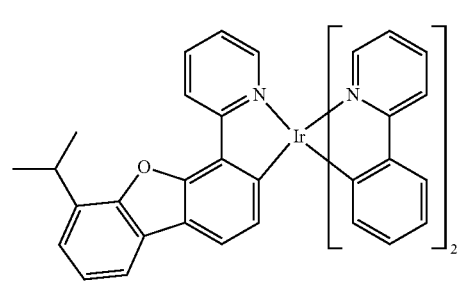
D-155
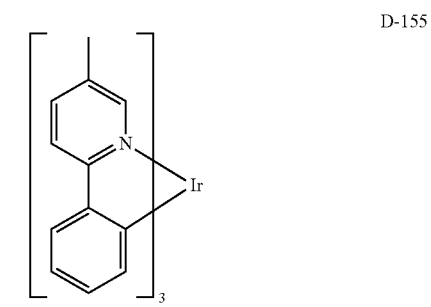

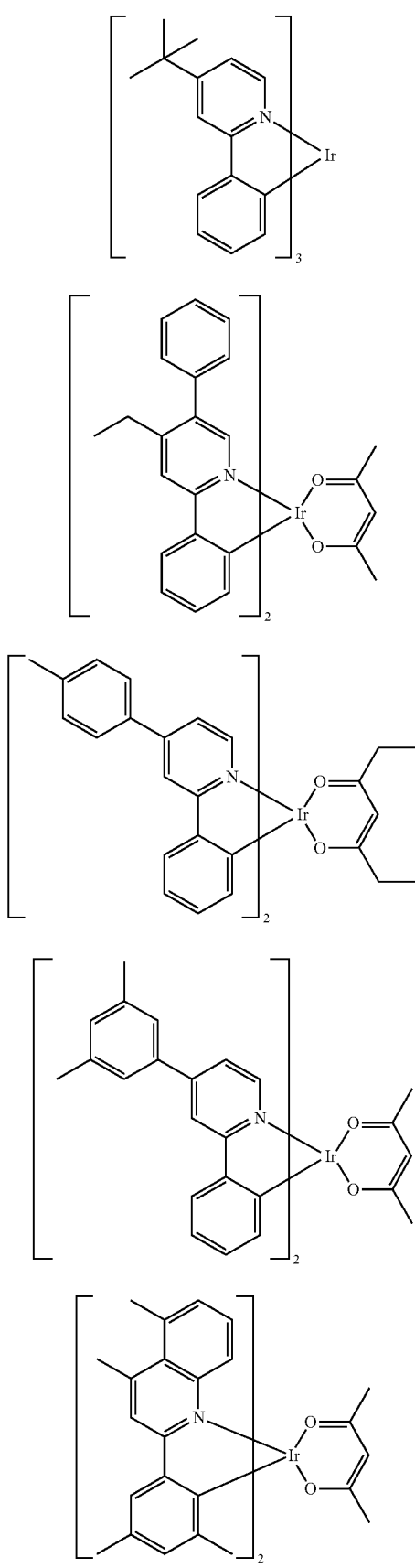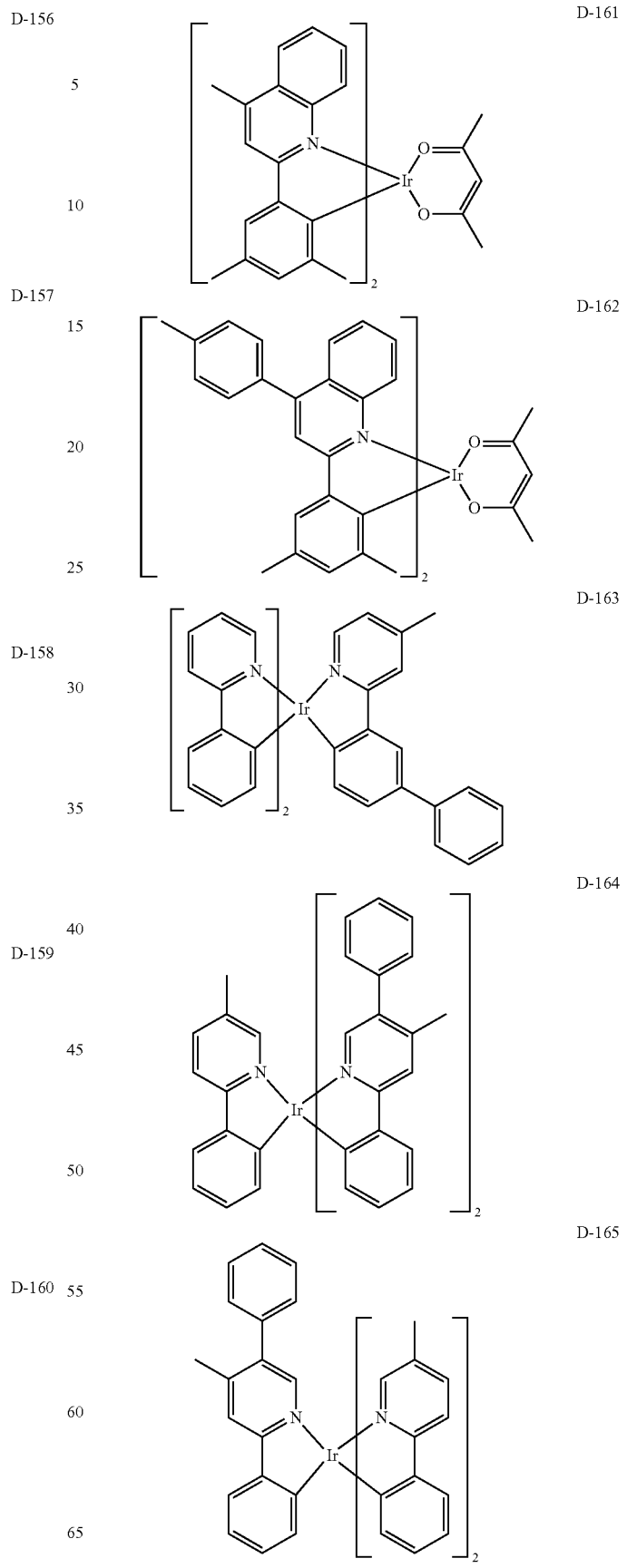

D-166
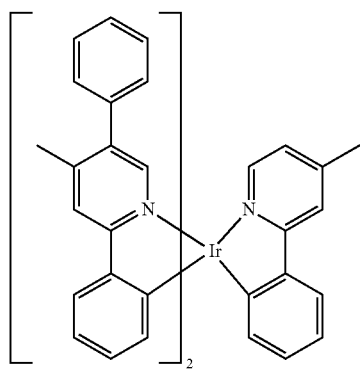
D-167
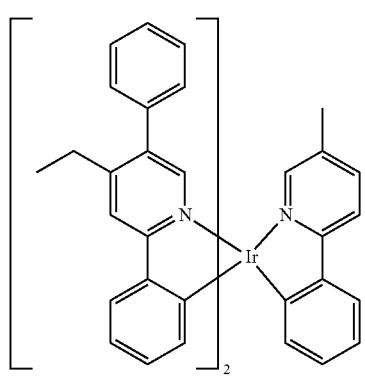
D-168
D-169
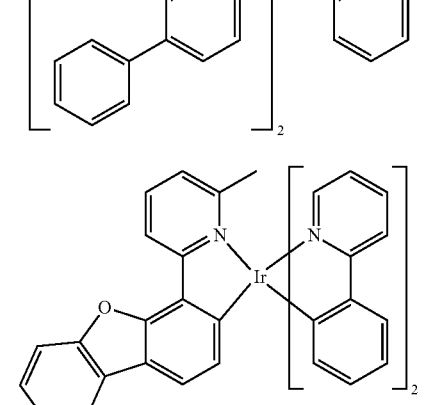
D-170
D-171
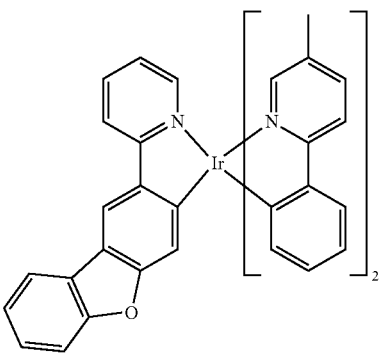
D-172
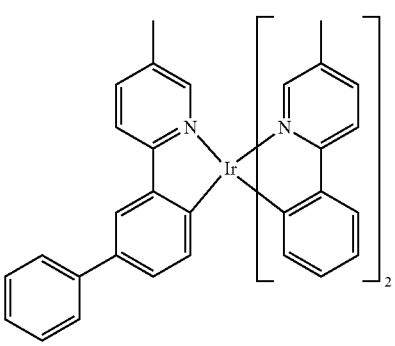
D-173
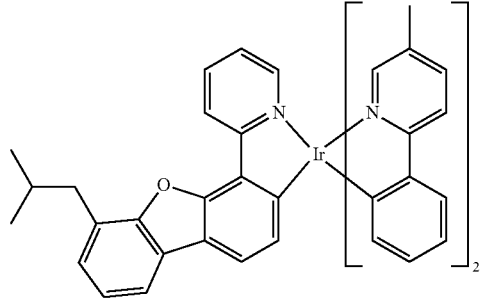
D-174
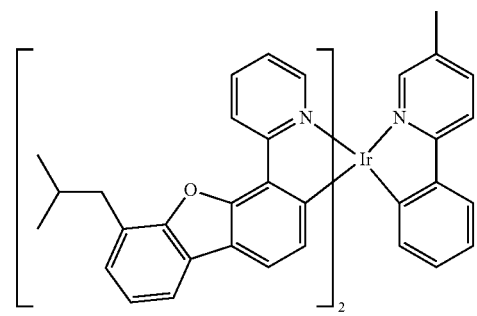

D-175
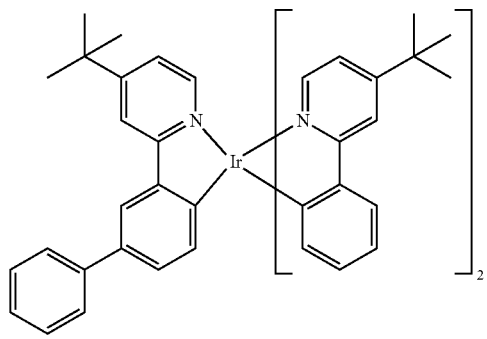
D-176
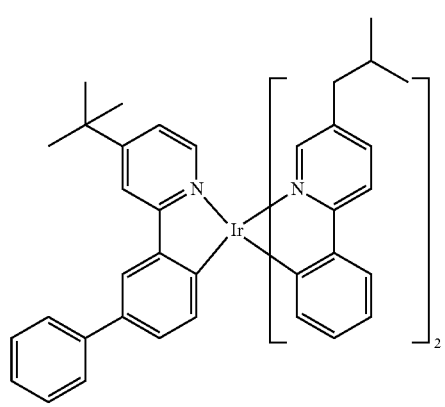
D-177
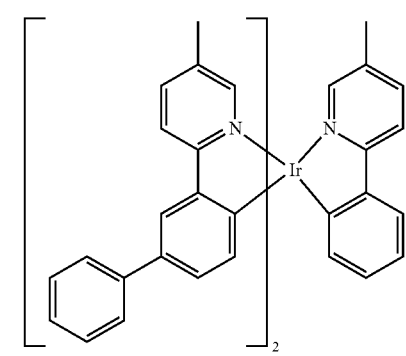
D-178
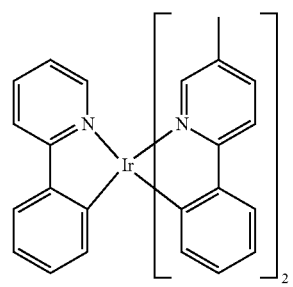
D-179
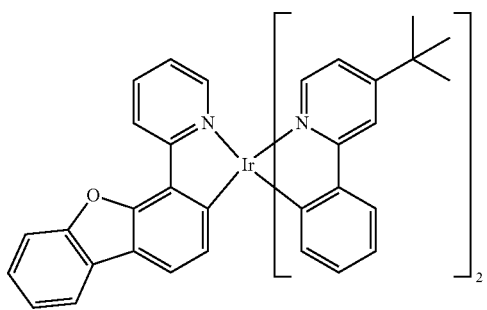
D-180
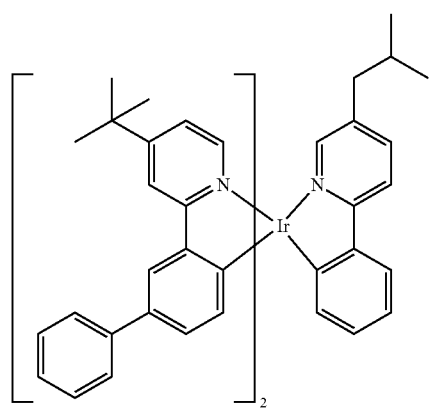
D-181
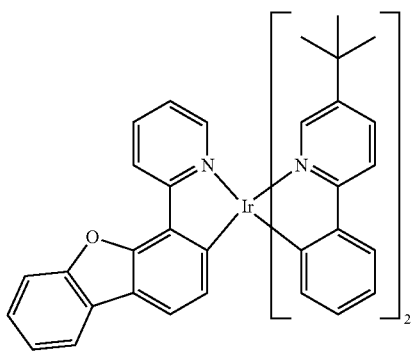
D-182
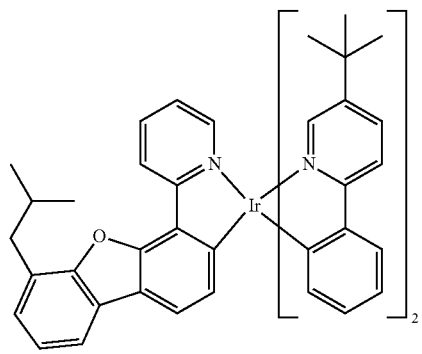

-continued
D-183
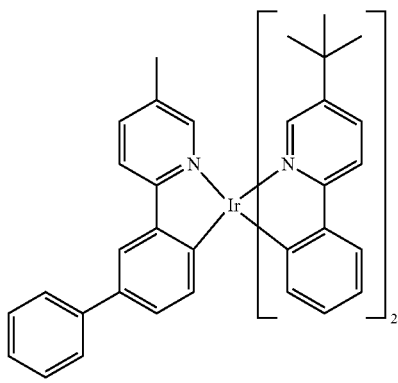
D-184
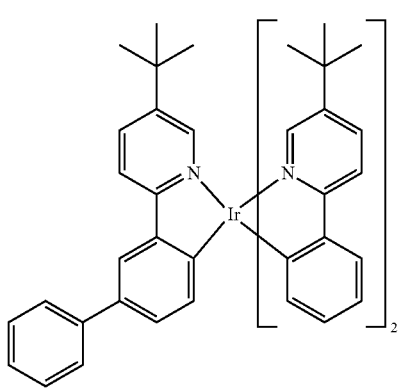
D-185
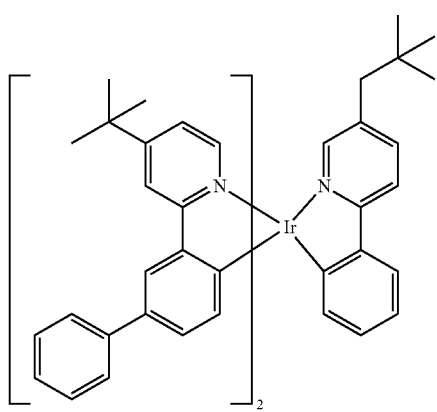
D-186
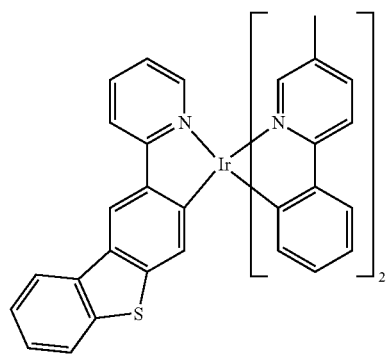
D-187
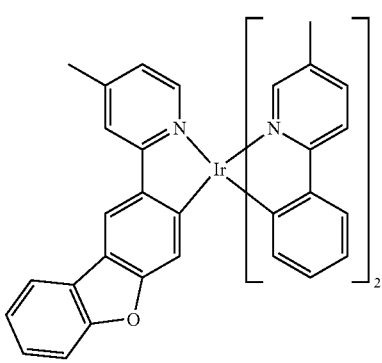
D-188
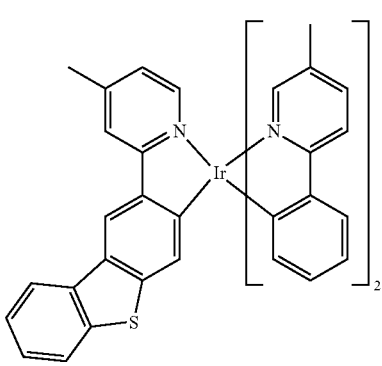
D-189
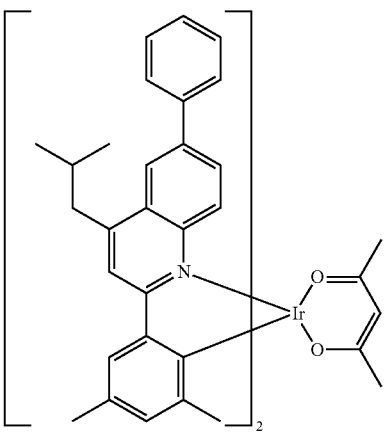
D-190
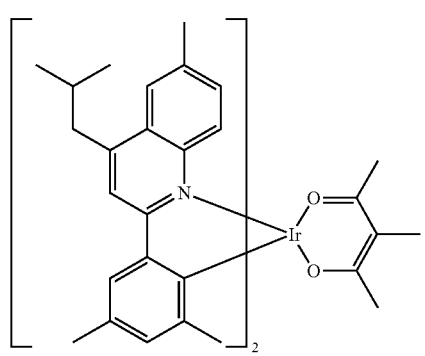

-continued

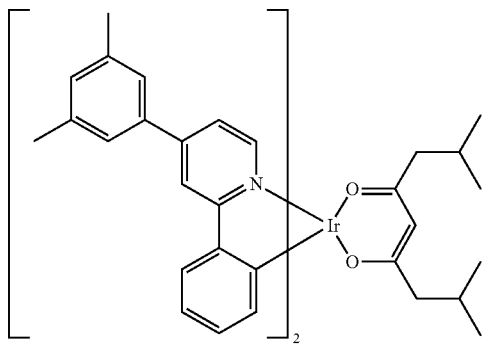
D-191

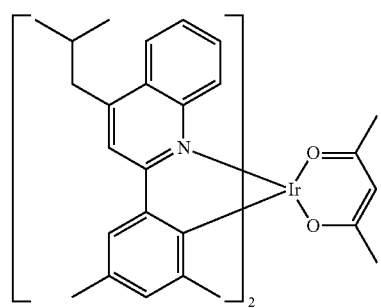
D-192

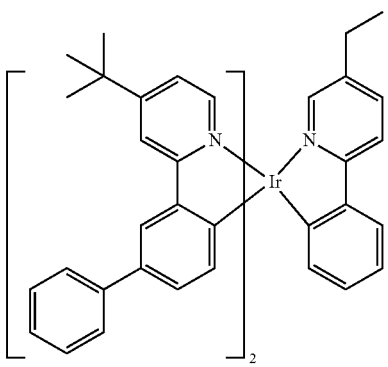
D-193

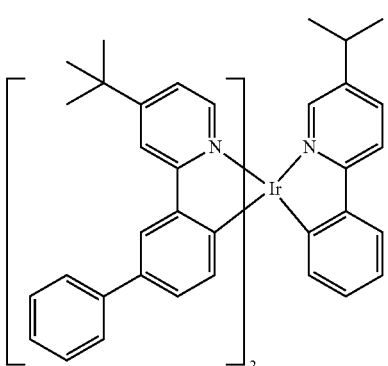
D-194

-continued

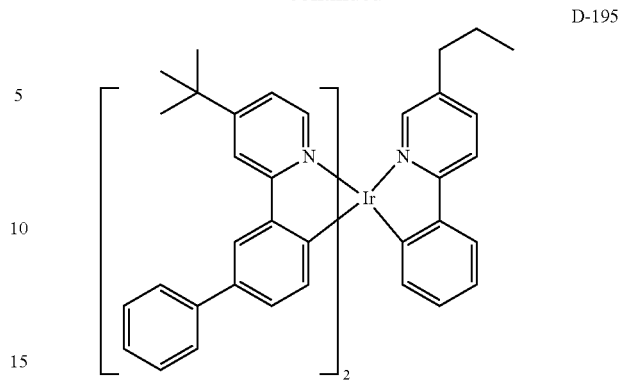
D-195

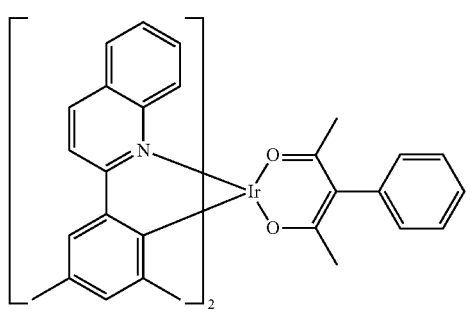
D-196

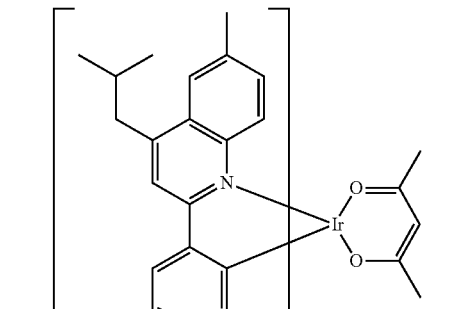
D-197

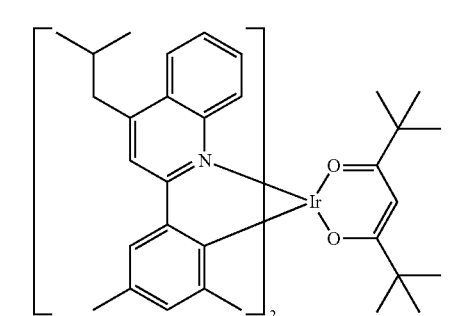
D-198

According to an additional aspect of the present disclosure, a mixture or composition for preparing an organic electroluminescent device is provided. The mixture or composition comprises the compound of the present disclosure. The mixture or composition may be used for preparing a light-emitting layer of the organic electroluminescent device. The mixture or composition may be used for preparing a phosphorescent or fluorescent light-emitting layer. When comprised in the mixture or composition, the compound of the present disclosure may be comprised as a host material. When the compound of the present disclosure is comprised as a host material, the mixture or composition may further comprise a second host material. The weight ratio between the compound of the present disclosure and the second host material is in the range of 1:99 to 99:1.

The organic electroluminescent device of the present disclosure may comprise a first electrode, a second electrode, and at least one organic layer disposed between the first and second electrodes, wherein the organic layer may comprise the material for an organic electroluminescent device of the present disclosure.

The organic electroluminescent device of the present disclosure may further comprise, in addition to the organic electroluminescent compound of formula 1, at least one compound selected from the group consisting of arylamine-based compounds and styrylarylamine-based compounds.

In the organic electroluminescent device of the present disclosure, the organic layer may further comprise, in addition to the compound of formula 1, at least one metal selected from the group consisting of metals of Group 1, metals of Group 2, transition metals of the $4^{th}$ period, transition metals of the $5^{th}$ period, lanthanides and organic metals of the d-transition elements of the Periodic Table, or at least one complex compound comprising the metal. The organic layer may further comprise a light-emitting layer and a charge generating layer.

In addition, the organic electroluminescent device of the present disclosure may emit white light by further comprising at least one light-emitting layer, which comprises a blue electroluminescent compound, a red electroluminescent compound or a green electroluminescent compound known in the art, besides the compound of the present disclosure. If necessary, the organic electroluminescent device of the present disclosure may further comprise a yellow- or orange-light-emitting layer.

In the organic electroluminescent device of the present disclosure, preferably, at least one layer (hereinafter, "a surface layer") may be placed on an inner surface(s) of one or both electrode(s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X(1 \leq X \leq 2)$, $AlO_X(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the organic electroluminescent compound of the present disclosure, the preparation method of the compound, and the luminescent properties of the device will be explained in detail with reference to the following examples.

Example 1: Preparation of Compound H-12

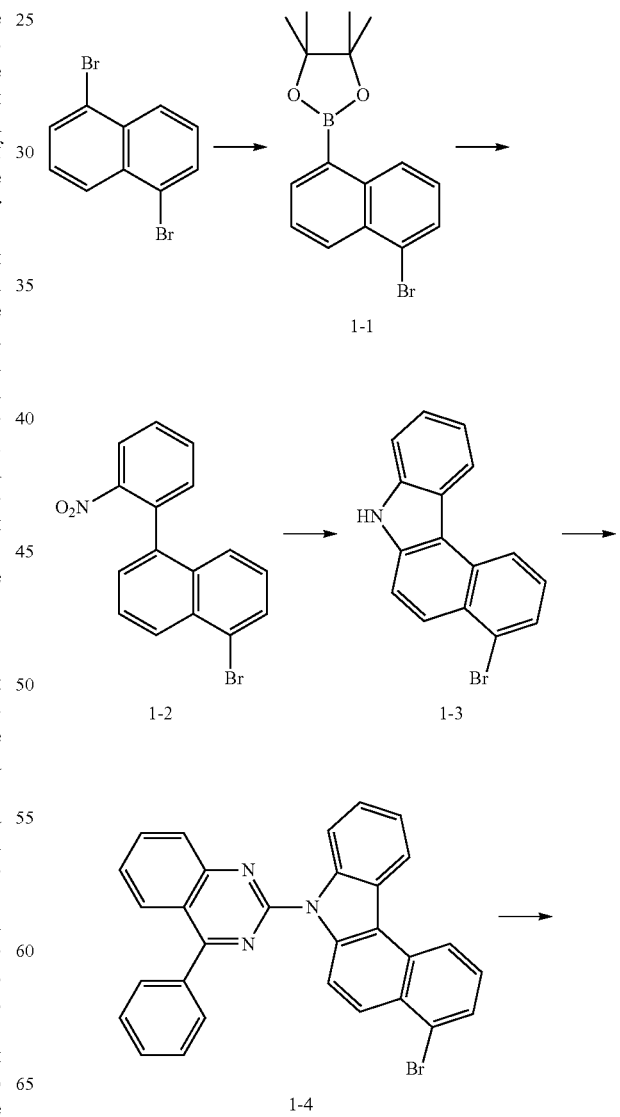

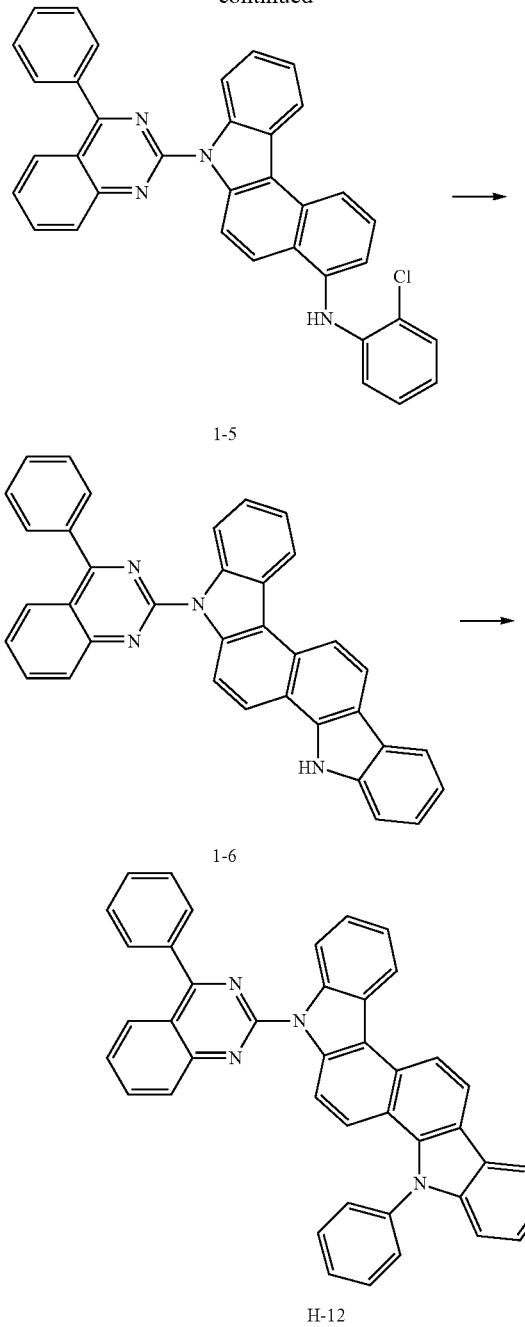

Preparation of Compound 1-1

After dissolving 1,5-dibromonaphthalene (65 g, 209.8 mmol), 4,4,4',4',5,5,5',5'-octamethyl-2,2'-bi(1,3,2-dioxaborolane) (53 g, 209.5 mmol), potassium acetate (KOAc) (65 g, 618 mmol), and tetrakis(triphenylphosphine)palladium [Pd(PPh$_3$)$_4$] (15 g, 20.9 mmol) in tetrahydrofuran (THF) (500 mL), the mixture was under reflux at 120° C. for 5 hours. After completion of the reaction, the mixture was extracted with ethyl acetate. The obtained organic layer was dried with magnesium sulfate to remove the remaining moisture, and subjected to column chromatography to obtain compound 1-1 (57 g, yield: 81%).

Preparation of Compound 1-2

After dissolving compound 1-1 (56 g, 167.8 mmol), 1-bromo-2-nitrobenzene (34 g, 167.8 mmol), Pd(PPh$_3$)$_4$ (10 g, 8.3 mmol), and 2M Na$_2$CO$_3$ (250 mL) in toluene (500 mL) and ethanol (250 mL), the mixture was under reflux at 120° C. for 5 hours. After completion of the reaction, the mixture was extracted with ethyl acetate. The obtained organic layer was dried with magnesium sulfate to remove the remaining moisture, and subjected to column chromatography to obtain compound 1-2 (50 g, yield: 88%).

Preparation of Compound 1-3

After dissolving compound 1-2 (17.7 g, 54 mmol) and triphenylphosphine (28.5 g, 108 mmol) in dichlorobenzene (DCB) (300 mL), the mixture was stirred under reflux for 24 hours. After completion of the reaction, the mixture was cooled to room temperature and distilled under vacuum. Methanol (MeOH) was added to the distilled resultant. The obtained solid was filtered under reduced pressure, and subjected to column chromatography to obtain compound 1-3 (10 g, yield: 75%).

Preparation of Compound 1-4

After introducing compound 1-3 (2.7 g, 11.0 mmol), 2-chloro-4-phenylquinazoline (3.1 g, 13.2 mmol), and sodium hydride (0.53 g, 22.0 mmol) into a 250 mL reaction flask, the mixture was stirred at room temperature for 5 hours. After completion of the reaction, MeOH and H$_2$O were added thereto. The obtained solid was subjected to column chromatography to obtain compound 1-4 (4 g, yield: 77%).

Preparation of Compound 1-5

After dissolving compound 1-4 (8 g, 17.1 mmol), 2-chloroaniline (2.6 g, 20.5 mmol), and palladium acetate [Pd(OAc)] (0.2 g, 0.86 mmol), sodium tert-butoxide (NaOtBu) (5 g, 51.3 mmol), and P(t-Bu)$_3$ (5.1 g, 20.5 mmol) in toluene (100 mL), the mixture was stirred under reflux for 24 hours. After completion of the reaction, the mixture was cooled to room temperature and distilled under vacuum. MeOH was added to the distilled resultant. The obtained solid was filtered under reduced pressure, and subjected to column chromatography to obtain compound 1-5 (8 g, yield: 88%).

Preparation of Compound 1-6

After dissolving compound 1-5 (8 g, 15 mmol), tricyclohexyl phosphonium tetrafluoroborate (0.6 g, 1.5 mmol), Cs$_2$CO$_3$ (15 g, 45 mmol), and Pd(OAc) (0.2 g, 0.75 mmol) in dimethylacetamide (DMA) (50 mL), the mixture was stirred under reflux for 4 hours. After completion of the reaction, the mixture was cooled to room temperature. MeOH was added to the mixture. The obtained solid was filtered under reduced pressure, and subjected to column chromatography to obtain compound 1-6 (8 g, yield: 65%).

Preparation of Compound H-12

After dissolving compound 1-6 (2.3 g, 4.5 mmol), iodobenzene (1.4 g, 6.75 mmol), K$_3$PO$_4$ (3 g, 13.5 mmol), CuI (0.5 g, 2.3 mmol), and ethylene diamine (EDA) (0.3 mL, 4.5 mmol) in toluene (50 mL), the mixture was stirred under reflux for 4 hours. After completion of the reaction, the mixture was cooled to room temperature. MeOH was added to the mixture. The obtained solid was filtered under reduced pressure, and subjected to column chromatography to obtain compound H-12 (2 g, yield: 75%).

[Physical properties] Melting point: 309° C., UV 391 nm (in toluene), PL 527 nm (in toluene), MS/EIMS 586.08

[Device Example 1] OLED Using the Organic Electroluminescent Compound of the Present Disclosure OLED was produced using the organic electroluminescent compound of the present disclosure as follows. A transparent electrode indium tin oxide (ITO) thin film (10

Ω/sq) on a glass substrate for an OLED (Geomatec) was subjected to an ultrasonic washing with acetone, ethanol, and distilled water sequentially, and was then stored in isopropanol. The ITO substrate was then mounted on a substrate holder of a vacuum vapor depositing apparatus. HI-1 was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. HI-2 was then introduced into another cell of said vacuum vapor depositing apparatus, and evaporated by applying electric current to the cell, thereby forming a second hole injection layer having a thickness of 5 nm on the first hole injection layer. HT-1 was introduced into one cell of the vacuum vapor depositing apparatus, and evaporated by applying electric current to the cell, thereby forming a first hole transport layer having a thickness of 10 nm on the second hole injection layer. HT-2 was introduced into another cell of the vacuum vapor depositing apparatus, and evaporated by applying electric current to the cell, thereby forming a second hole transport layer having a thickness of 60 nm on the first hole transport layer. Thereafter, compound H-12 was introduced into one cell of the vacuum vapor depositing apparatus as a host, and compound D-96 was introduced into another cell as a dopant. The two materials were evaporated at different rates, so that the dopant was deposited in a doping amount of 3 wt % based on the total amount of the host and dopant to form a light-emitting layer having a thickness of 40 nm on the hole transport layer. ET-1 and EI-1 were introduced into two cells of the vacuum vapor depositing apparatus, respectively, and evaporated at a 1:1 rate to form an electron transport layer having a thickness of 30 nm on the light-emitting layer. After depositing EI-1 as an electron injection layer having a thickness of 2 nm, an Al cathode having a thickness of 80 nm was then deposited by another vacuum vapor deposition apparatus on the electron injection layer to produce an OLED.

The produced OLED showed a red emission and an efficiency of 10.4 cd/A at 1,000 nit.

HI-1

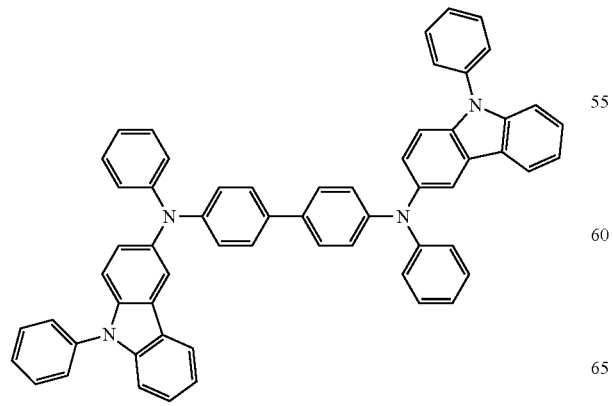

HI-2

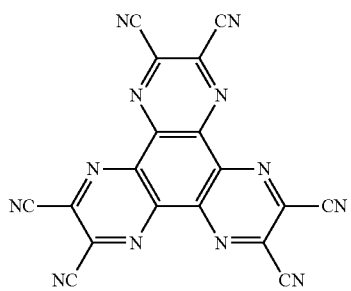

HT-1

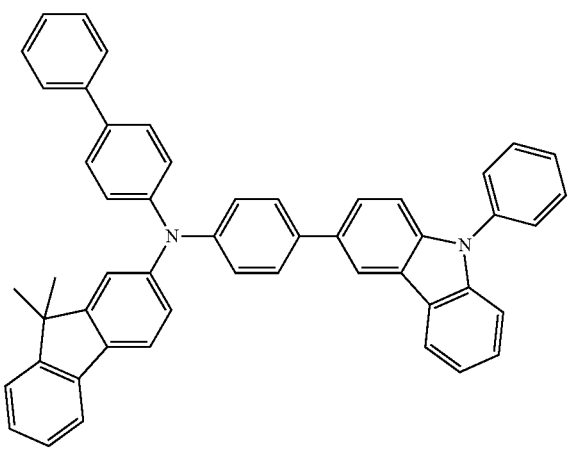

HT-2

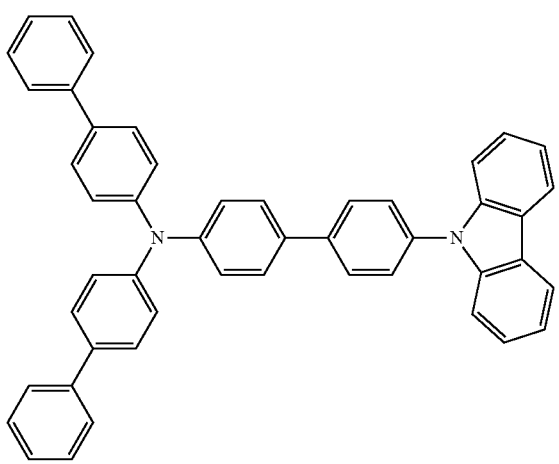

ET-1

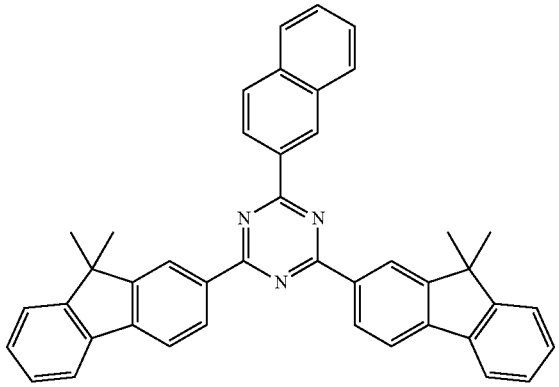

-continued

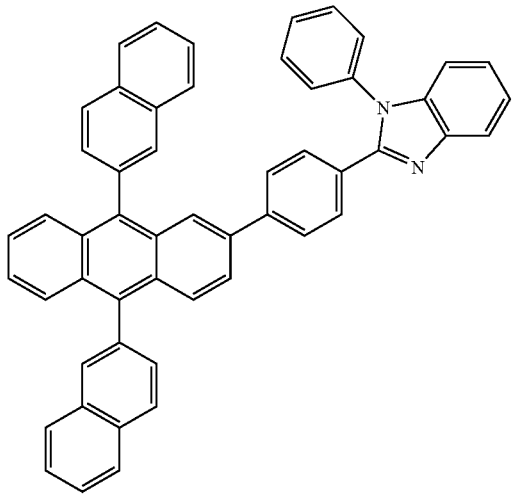

ET-2

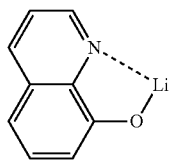

EI-1

[Comparative Example 1] OLED Using a Conventional Organic Electroluminescent Compound OLED was produced in the same manner as in Device Example 1, except that the following comparative compound-1 was used as a host material of a light-emitting layer, and ET-2 was used for an electron transport layer instead of ET-1. The produced OLED showed a red emission and an efficiency of 8.8 cd/A at 1,000 nit.

Comparative compound-1

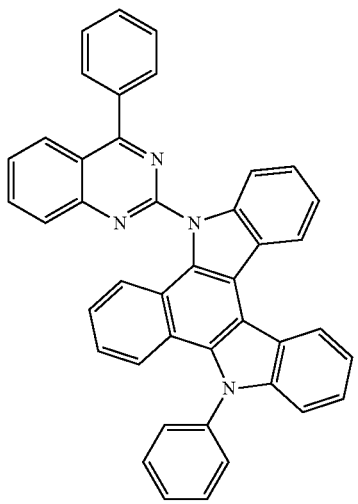

As confirmed in the Device Example above, the organic electroluminescent compound of the present disclosure provides better luminous efficiency (in particular, current efficiency) than conventional organic electroluminescent compounds.

The invention claimed is:

1. An organic electroluminescent compound represented by the following formula 1:

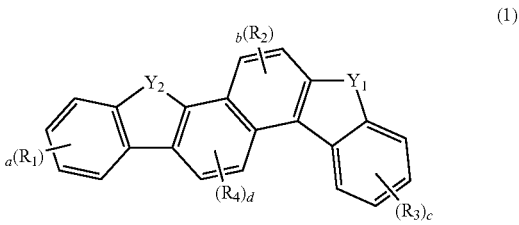

(1)

wherein $Y_1$ and $Y_2$, each independently, represent $NR_{11}$, $CR_{12}R_{13}$, O, or S; with the proviso that at least one of $Y_1$ and $Y_2$ represents $NR_{11}$;

$R_{11}$ represents *-$L_1$-Ar;

* represents a bonding site;

$L_1$ represents a single bond, a substituted or unsubstituted (C6-C30)arylene, or a substituted or unsubstituted 5- to 30-membered heteroarylene;

Ar represents a substituted or unsubstituted (C6-C30)aryl, or a substituted or unsubstituted 5- to 30-membered heteroaryl;

$R_{12}$ and $R_{13}$, each independently, represent a substituted or unsubstituted (C1-C30)alkyl, a substituted or unsubstituted (C6-C30)aryl, or a substituted or unsubstituted 5- to 30-membered heteroaryl; or may be linked to an adjacent substituent(s) to form a substituted or unsubstituted, (C3-C30), mono- or polycyclic, alicyclic or aromatic ring, whose carbon atom(s) may be replaced with at least one hetero atom selected from nitrogen, oxygen, and sulfur;

$R_1$ and $R_3$, each independently, represent hydrogen, deuterium, a halogen, a cyano, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted 3- to 7-membered heterocycloalkyl, a substituted or unsubstituted (C1-C30)alkoxy, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent(s) to form a substituted or unsubstituted, (C3-C30), mono- or polycyclic, alicyclic or aromatic ring, whose carbon atom(s) may be replaced with at least one hetero atom selected from nitrogen, oxygen, and sulfur;

$R_2$ and $R_4$, each independently, represent hydrogen, deuterium, a halogen, a cyano, a substituted or unsubstituted (C1-C30)alkyl, a substituted or unsubstituted (C6-C30)aryl, a substituted or unsubstituted (C3-C30)cycloalkyl, a substituted or unsubstituted 3- to 7-membered heterocycloalkyl, a substituted or unsubstituted (C1-C30)alkoxy, a substituted or unsubstituted tri(C1-C30)alkylsilyl, a substituted or unsubstituted tri(C6-

C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

a and c, each independently, represent an integer of 1 to 4; where a or c is an integer of 2 or more, each of $R_1$ or $R_3$ may be the same or different;

b and d, each independently, represent an integer of 1 to 2; where b or d is an integer of 2 or more, each of $R_2$ or $R_4$ may be the same or different; and the heteroaryl(ene) and heterocycloalkyl, each independently, contain at least one hetero atom selected from B, N, O, S, Si, and P.

2. The organic electroluminescent compound according to claim 1, wherein the substituents for the substituted alkyl, the substituted aryl(ene), the substituted heteroaryl(ene), the substituted cycloalkyl, the substituted heterocycloalkyl, the substituted alkoxy, the substituted trialkylsilyl, the substituted triarylsilyl, the substituted dialkylarylsilyl, the substituted alkyldiarylsilyl, the substituted mono- or di-alkylamino, the substituted mono- or di-arylamino, the substituted alkylarylamino, and the substituted mono- or polycyclic, alicyclic or aromatic ring in $L_1$, Ar, $R_{12}$, $R_{13}$, and $R_1$ to $R_4$, each independently, are at least one selected from the group consisting of deuterium, a halogen, a cyano, a carboxy, a nitro, a hydroxy, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 3- to 30-membered heteroaryl unsubstituted or substituted with a (C6-C30)aryl, a (C6-C30)aryl unsubstituted or substituted with a 3- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

3. The organic electroluminescent compound according to claim 1, wherein at least one of $Y_1$ and $Y_2$ represents $NR_{11}$ in which $L_1$ represents a single bond or a substituted or unsubstituted (C6-C21)arylene and Ar represents a substituted or unsubstituted 5- to 30-membered heteroaryl.

4. The organic electroluminescent compound according to claim 1, wherein one of $Y_1$ and $Y_2$ is $NR_{11a}$ and the other is $NR_{11b}$, $CR_{12}R_{13}$, O, or S;

$R_{11a}$ represents *-$L_{1a}$-$Ar_a$; $R_{11b}$ represents *-$L_{1b}$-$Ar_b$;

$L_{1a}$ and $L_{1b}$, each independently, represent a single bond or a substituted or unsubstituted (C6-C21)arylene;

$Ar_a$ represents a substituted or unsubstituted 5- to 30-membered heteroaryl;

$Ar_b$ represents a substituted or unsubstituted (C6-C30)aryl; and $R_{12}$ and $R_{13}$, each independently, represent a substituted or unsubstituted (C1-C10)alkyl, a substituted or unsubstituted (C6-C21)aryl, or a substituted or unsubstituted 5- to 21-membered heteroaryl, or may be linked to an adjacent substituent(s) to form a substituted or unsubstituted, (C3-C30), mono- or polycyclic aromatic ring.

5. The organic electroluminescent compound according to claim 4, wherein $L_{1a}$ represents a single bond, a substituted or unsubstituted phenylene, a substituted or unsubstituted biphenylene, or a substituted or unsubstituted naphthylene; $Ar_a$ represents a substituted or unsubstituted pyridyl, a substituted or unsubstituted pyrimidyl, a substituted or unsubstituted triazinyl, a substituted or unsubstituted pyrazinyl, a substituted or unsubstituted quinolyl, a substituted or unsubstituted isoquinolyl, a substituted or unsubstituted quinazolinyl, a substituted or unsubstituted quinoxalinyl, a substituted or unsubstituted naphthyridinyl, a substituted or unsubstituted carbazolyl, a substituted or unsubstituted dibenzothiophenyl, or a substituted or unsubstituted dibenzofuranyl.

6. The organic electroluminescent compound according to claim 5, wherein $Ar_a$ is selected from the following formulae 2-1 to 2-7:

(2-1)

(2-2)

(2-3)

(2-4)

(2-5)

(2-6)

-continued (2-7)

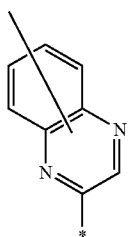

wherein $R_{21}$ to $R_{27}$, each independently, represent hydrogen, deuterium, a halogen, a cyano, a (C1-C30)alkyl, a (C3-C30)cycloalkyl, a (C6-C30)aryl unsubstituted or substituted with a halogen, a cyano, a (C1-C30)alkyl, a 5- to 18-membered heteroaryl, a di(C1-C30)alkyl(C6-C30)arylsilyl, a (C1-C30)alkyldi(C6-C30)arylsilyl, or a tri(C6-C30)arylsilyl, a 5- to 30-membered heteroaryl unsubstituted or substituted with a halogen, a cyano, a (C1-C30)alkyl, a (C6-C18)aryl, a di(C1-C30)alkyl(C6-C30)arylsilyl, a (C1-C30)alkyldi(C6-C30)arylsilyl, or a tri(C6-C30)arylsilyl, a di(C1-C30)alkyl(C6-C30)arylsilyl, a (C1-C30)alkyldi(C6-C30)arylsilyl, or a tri (C6-C30)arylsilyl;

f represents an integer of 1 to 4; g represents an integer of 1 to 3; h represents an integer of 1 to 2; i represents an integer of 1 to 6; j, k, and m, each independently, represent an integer of 1 to 5; where f, g, h, i, j, k, or m is an integer of 2 or more, each of $R_{21}$, $R_{22}$, $R_{23}$, $R_{24}$, $R_{25}$, $R_{26}$, or $R_{27}$ may be the same or different; and the heteroaryl contains at least one hetero atom selected from N, O, and S.

7. The organic electroluminescent compound according to claim 1, wherein the compound represented by formula 1 is selected from the group consisting of:

H-1

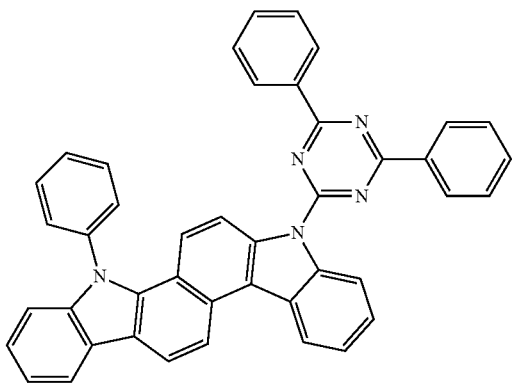

H-2

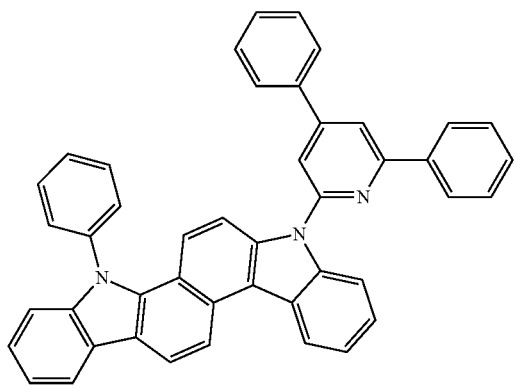

H-3

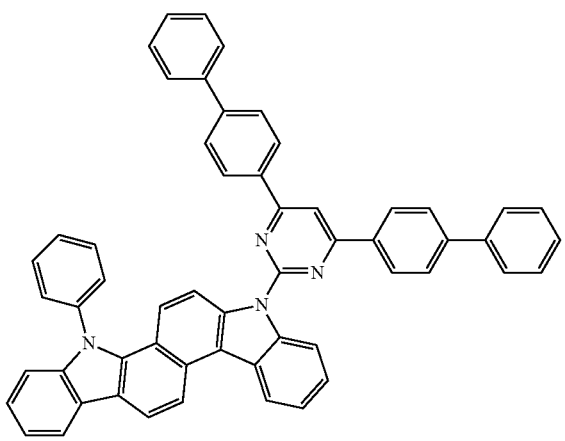

H-4

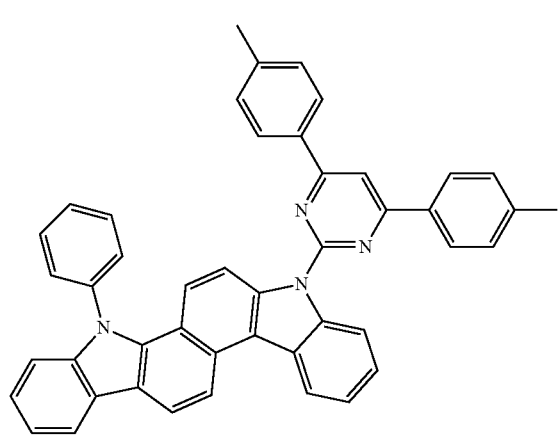

H-5

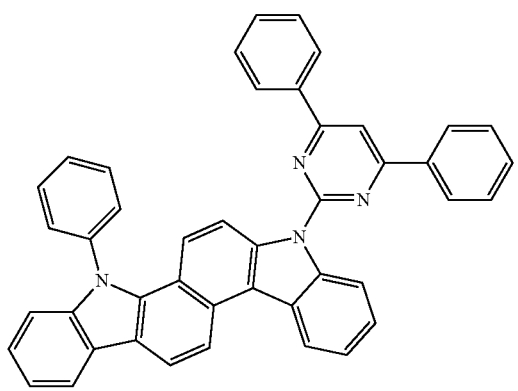

H-6
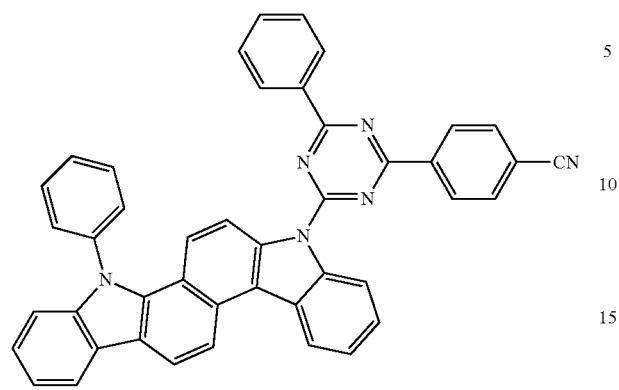
H-10
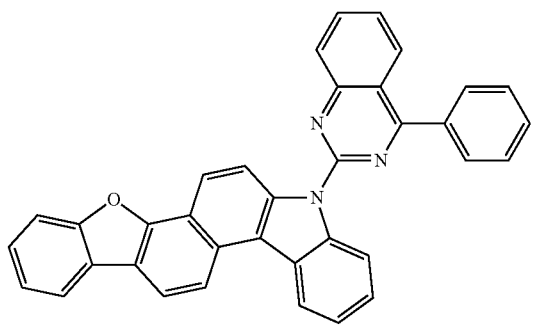
H-7
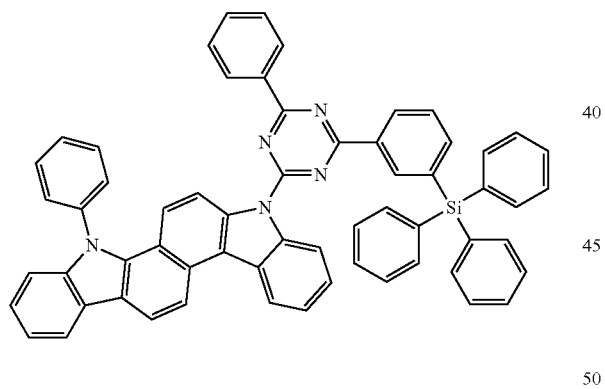
H-11
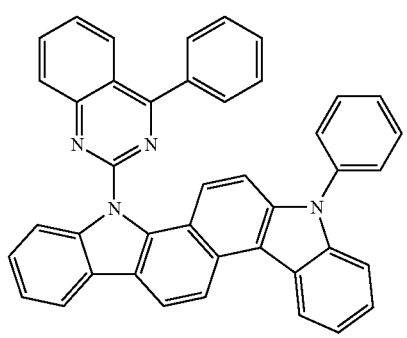
H-8
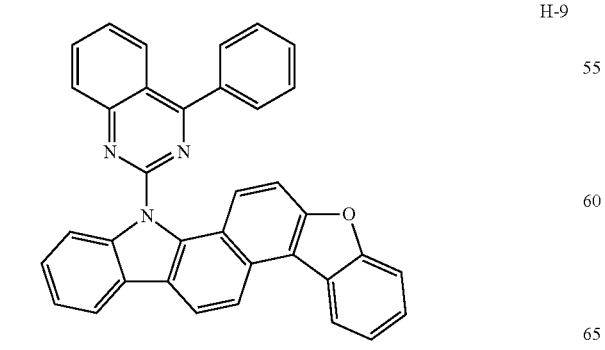
H-12
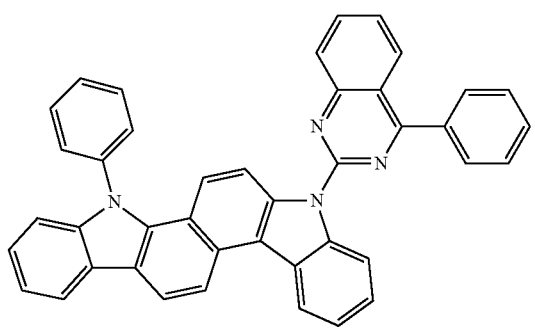
H-9
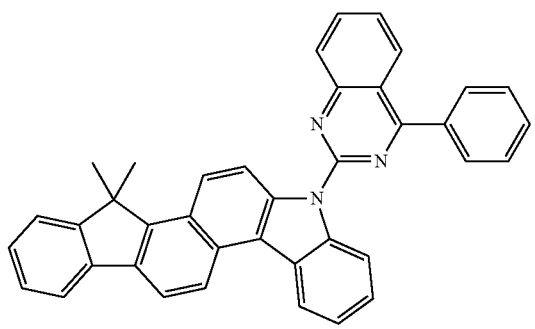
H-13

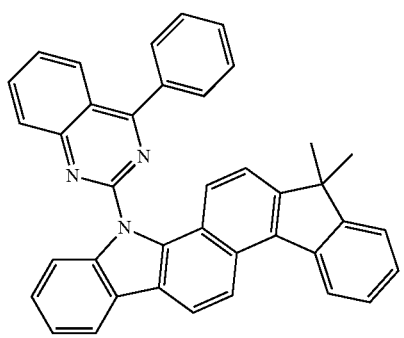
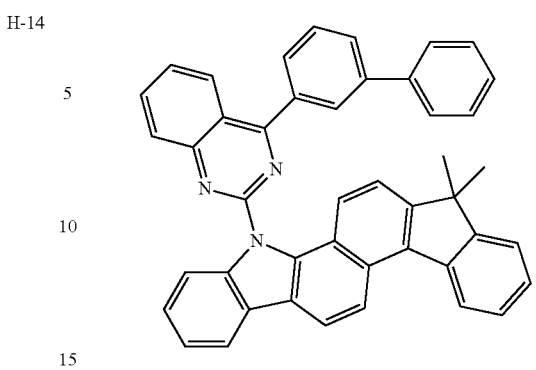

H-22
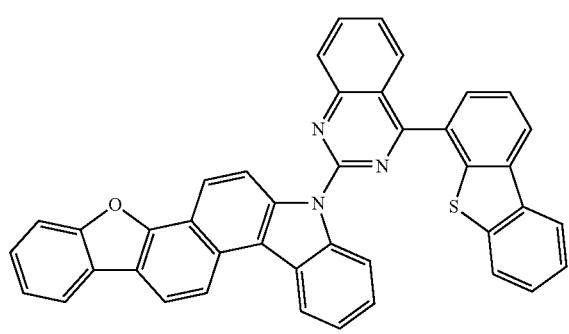
H-23
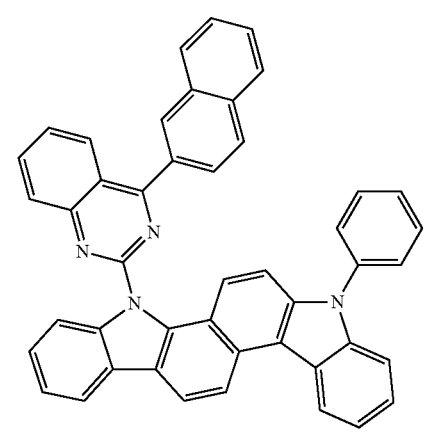
H-24
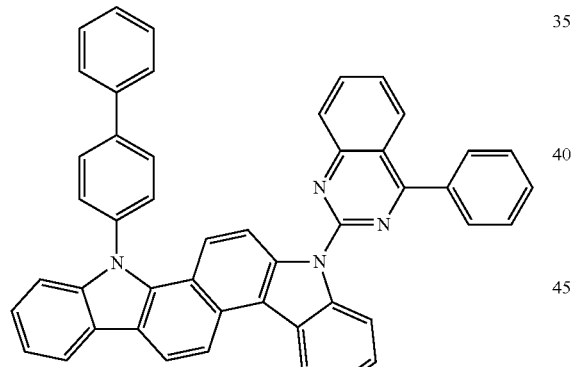
H-25
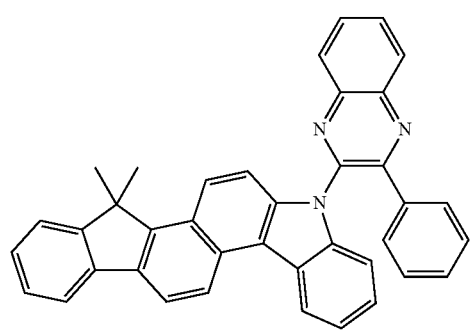
H-26
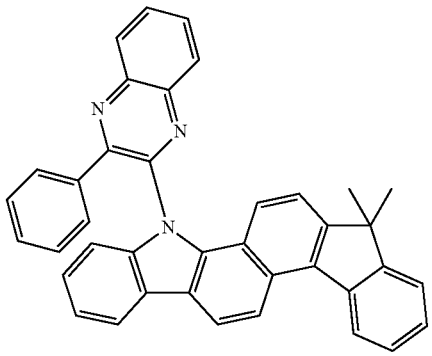
H-27
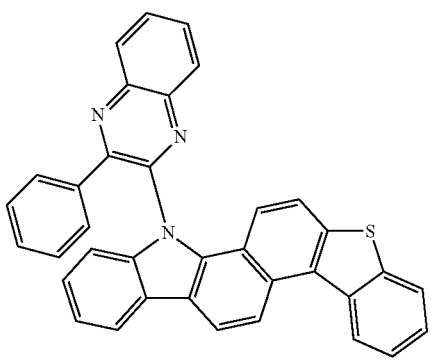
H-28
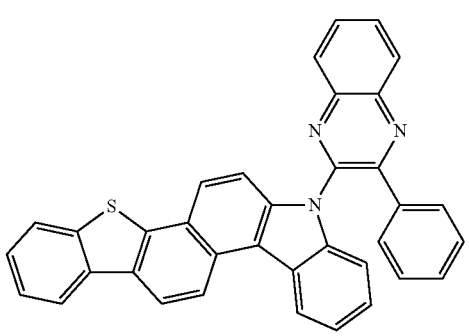
H-29
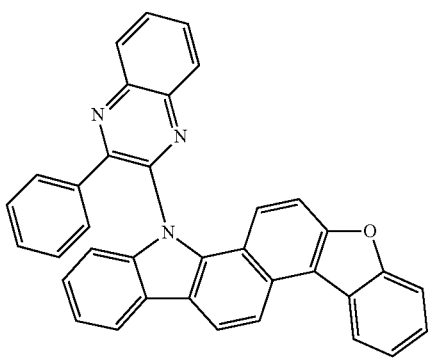

-continued
H-30
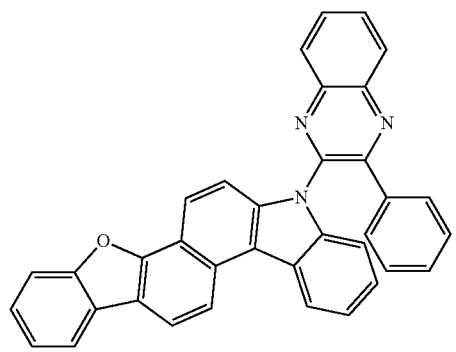
H-31
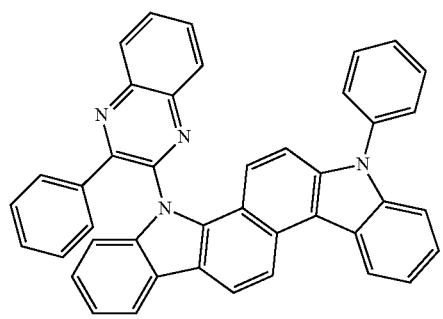
H-32
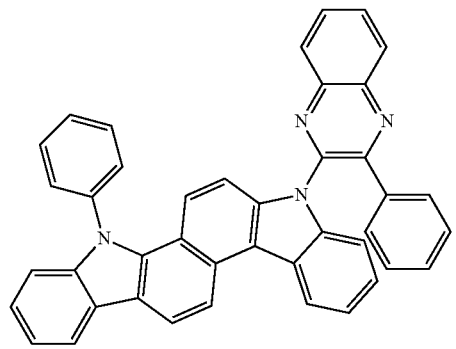
H-33
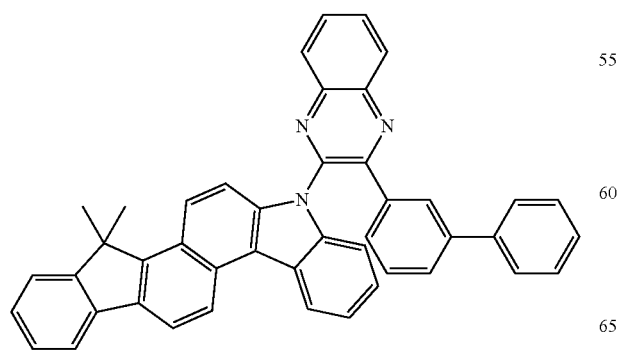
-continued
H-34
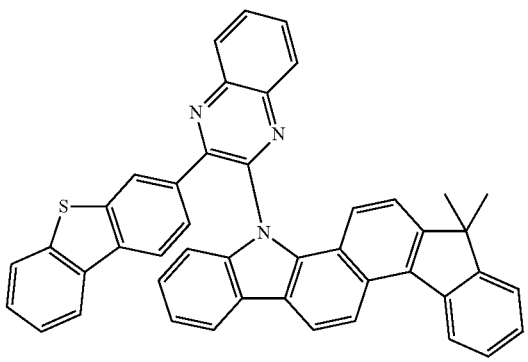
H-35
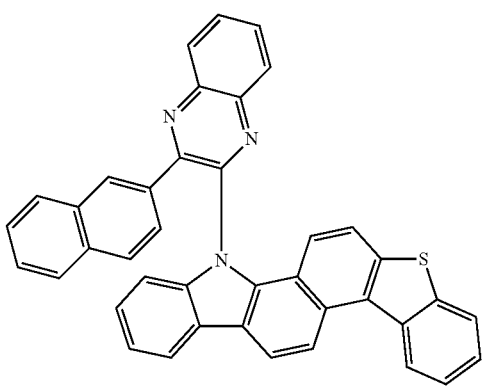
H-36
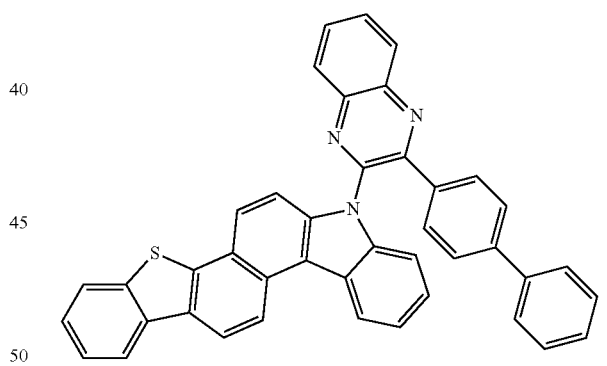
H-37
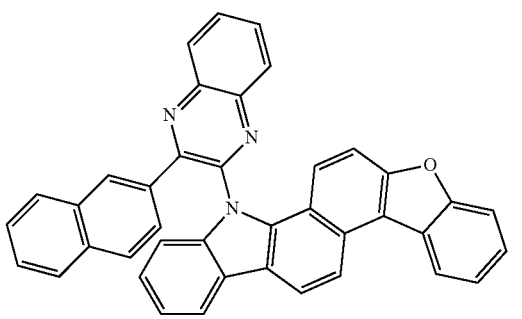

H-38
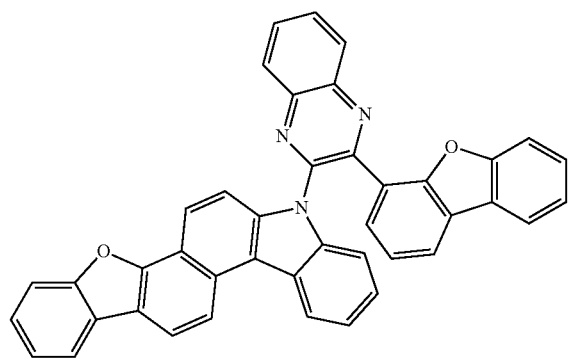
H-39
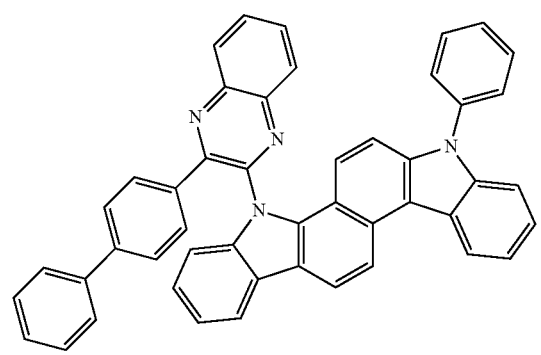
H-40
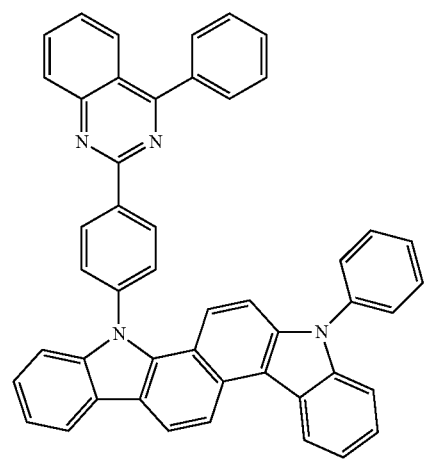
H-41
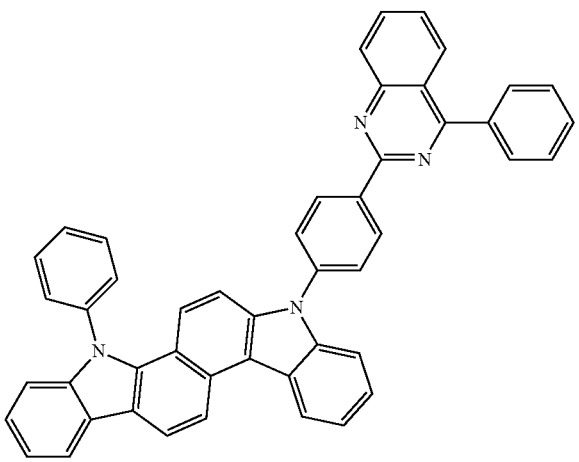
H-42
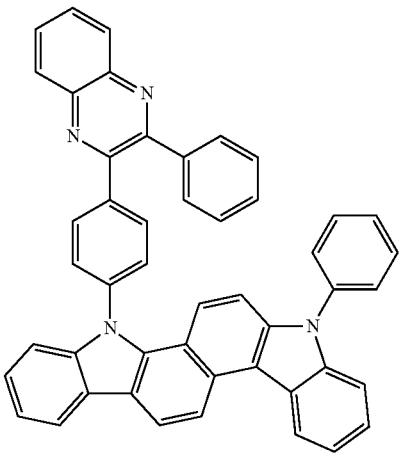
H-43
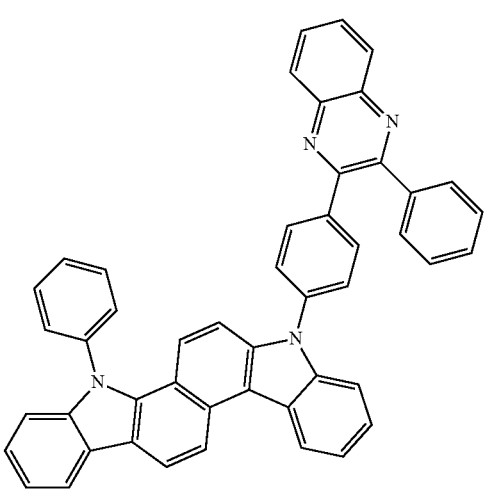

H-44
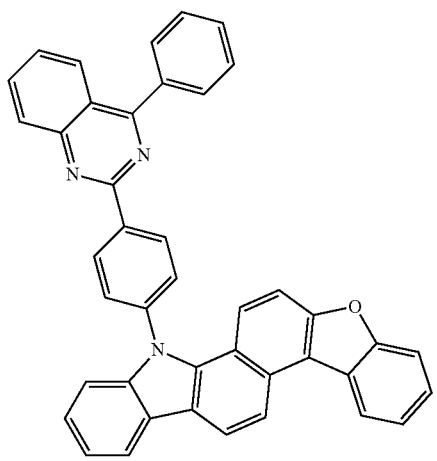
H-45
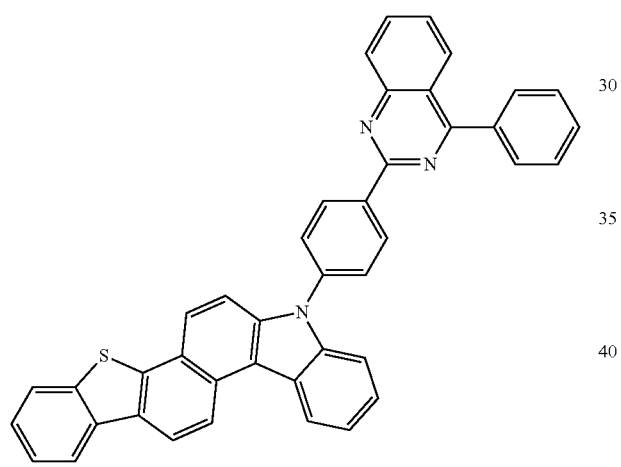
H-46
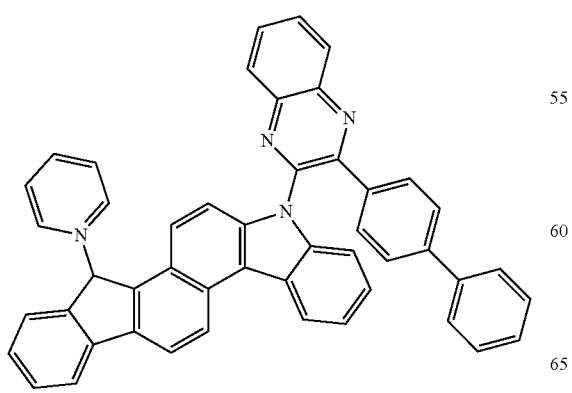
H-47
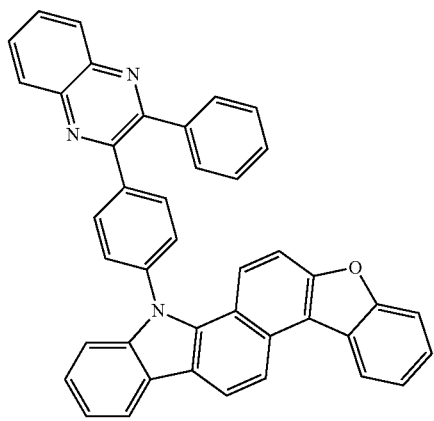
H-48
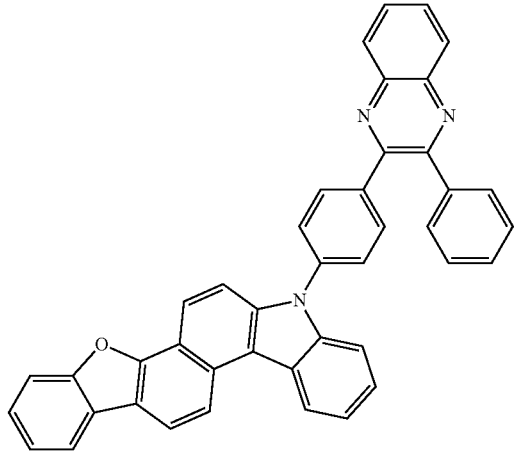
H-49

-continued
H-50
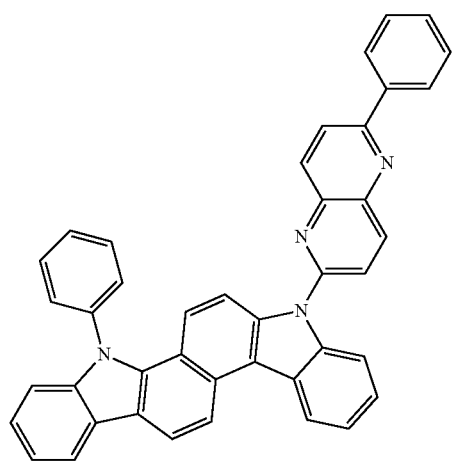
H-51
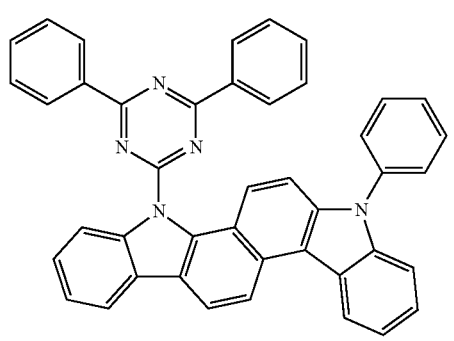
H-52
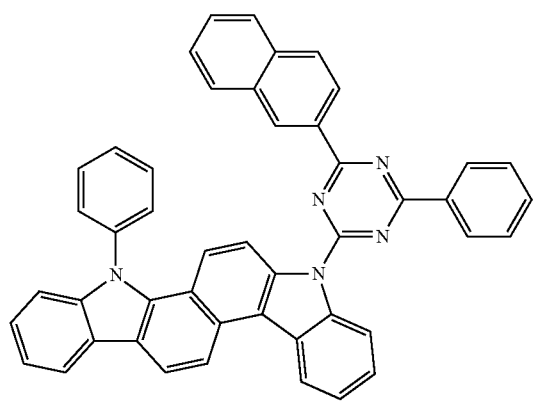
H-53
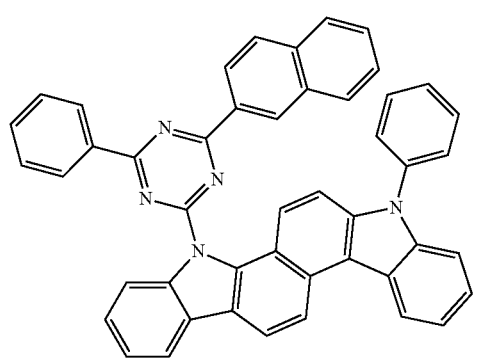
-continued
H-54
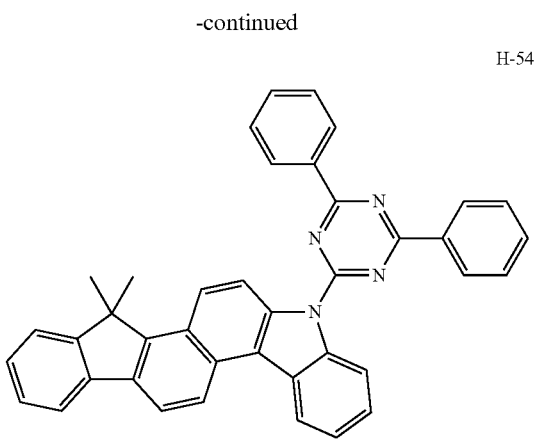
H-55
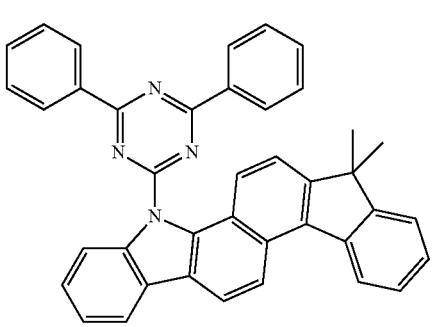
H-56
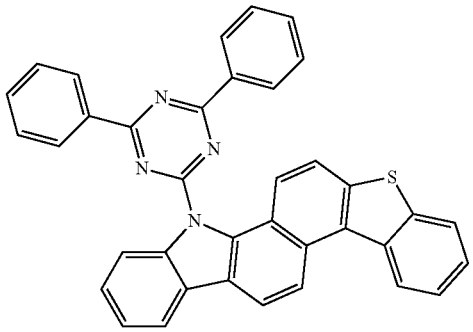
H-57
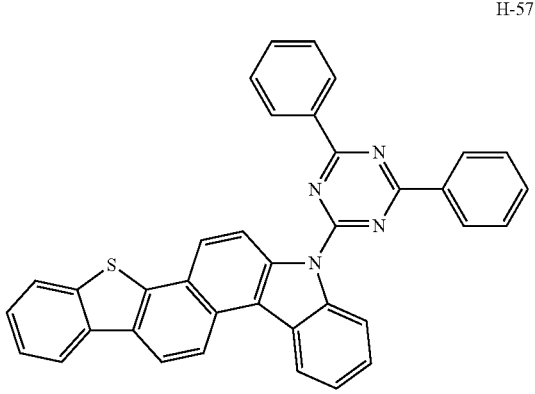

-continued
H-58
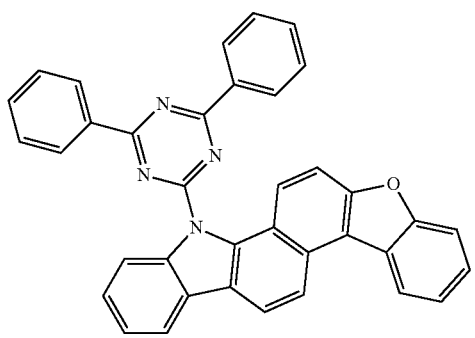
H-59
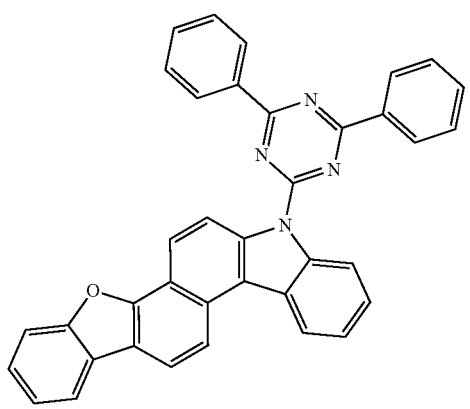
H-60
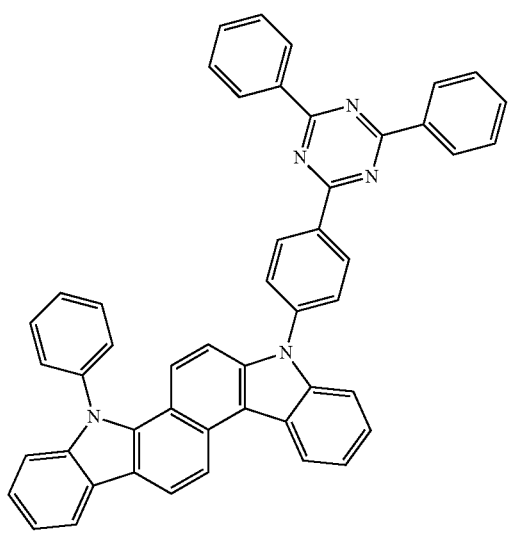
-continued
H-61
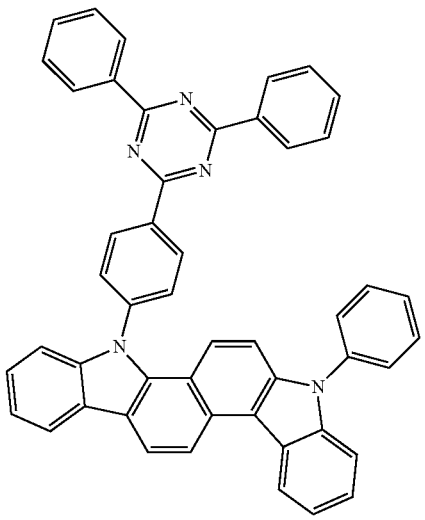
H-62
H-63
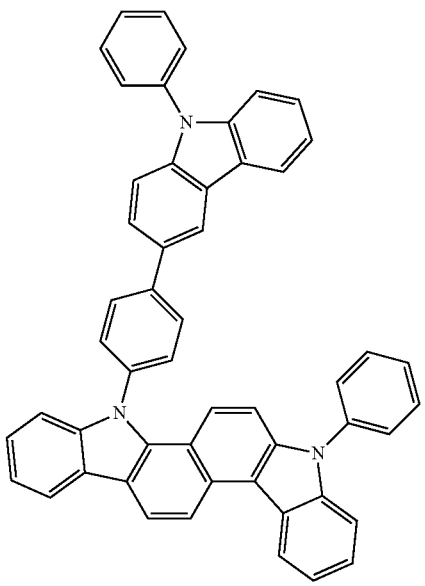

H-64
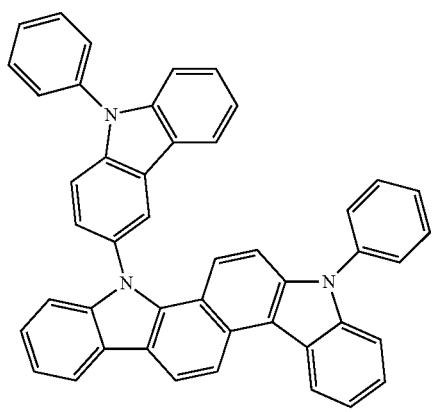
H-65
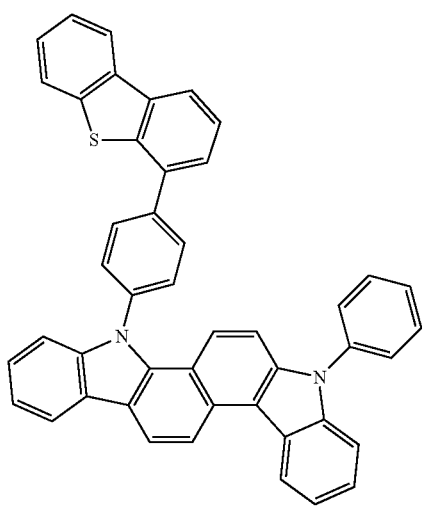
H-66
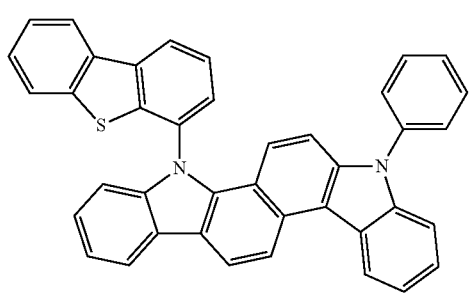
H-67
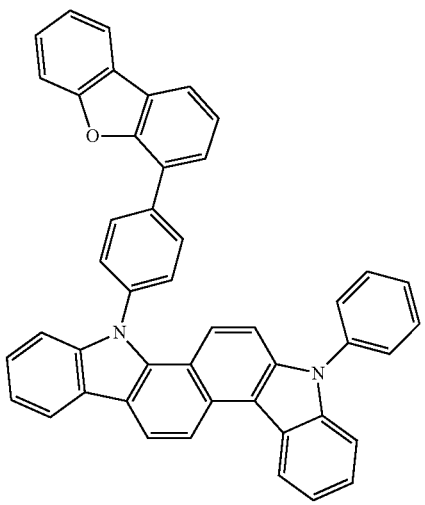
H-68
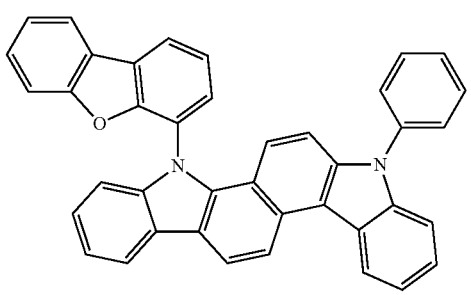
H-69
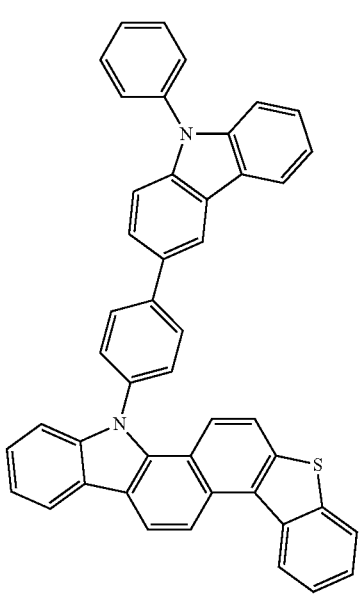

-continued
H-70
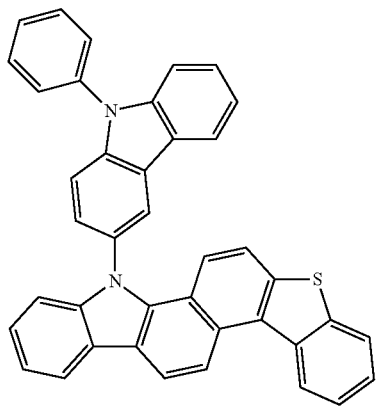
H-71
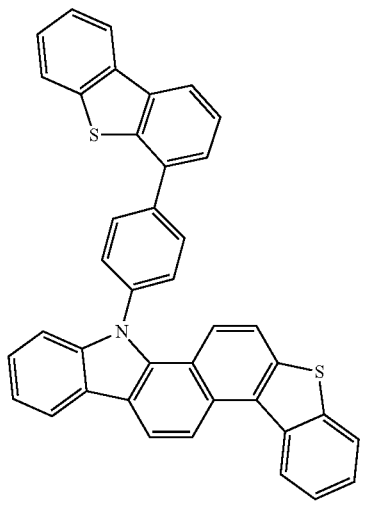
H-72
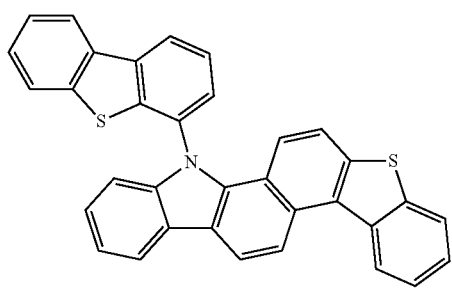
-continued
H-73
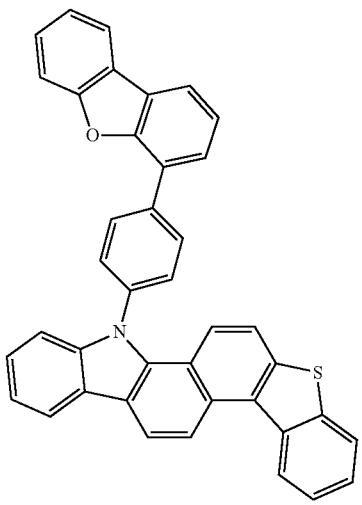
H-74
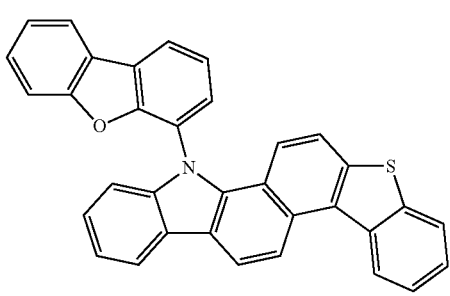
H-75
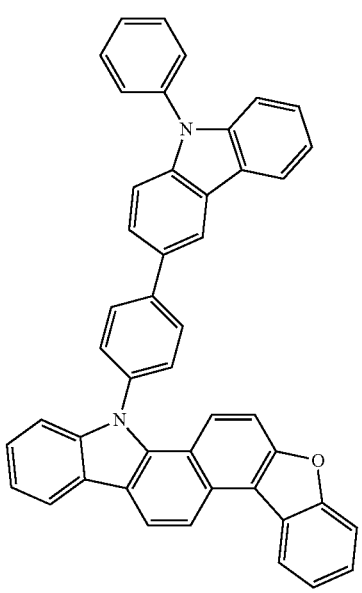

H-76
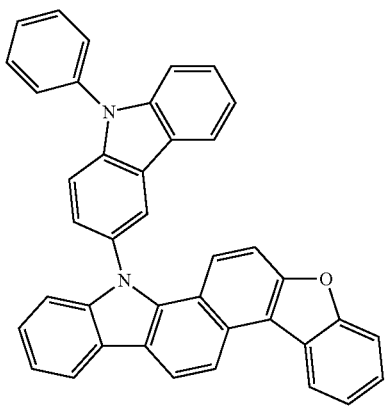
H-77
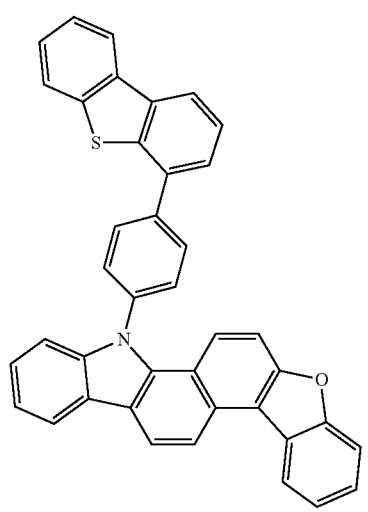
H-78
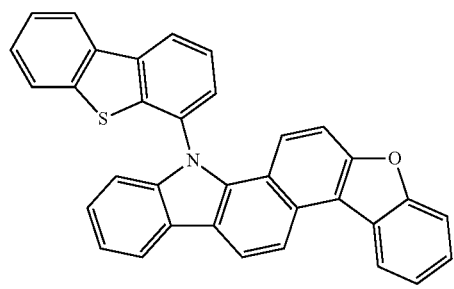
H-79
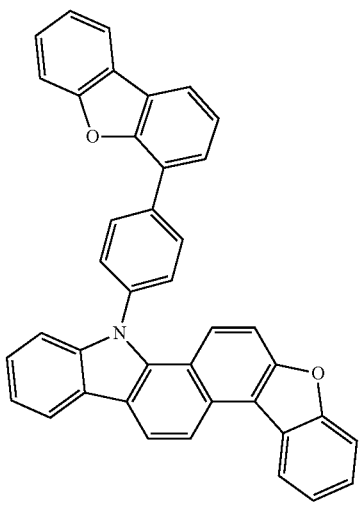
H-80
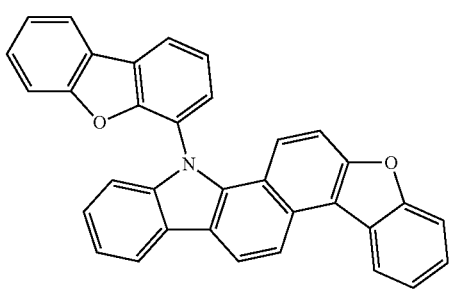
H-81
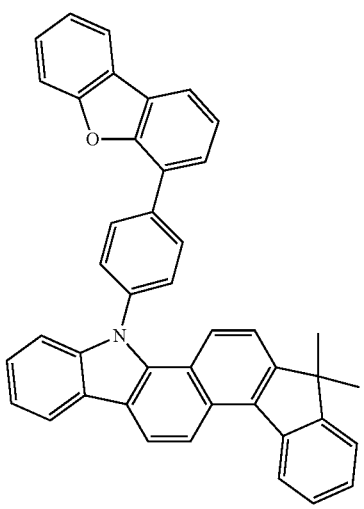

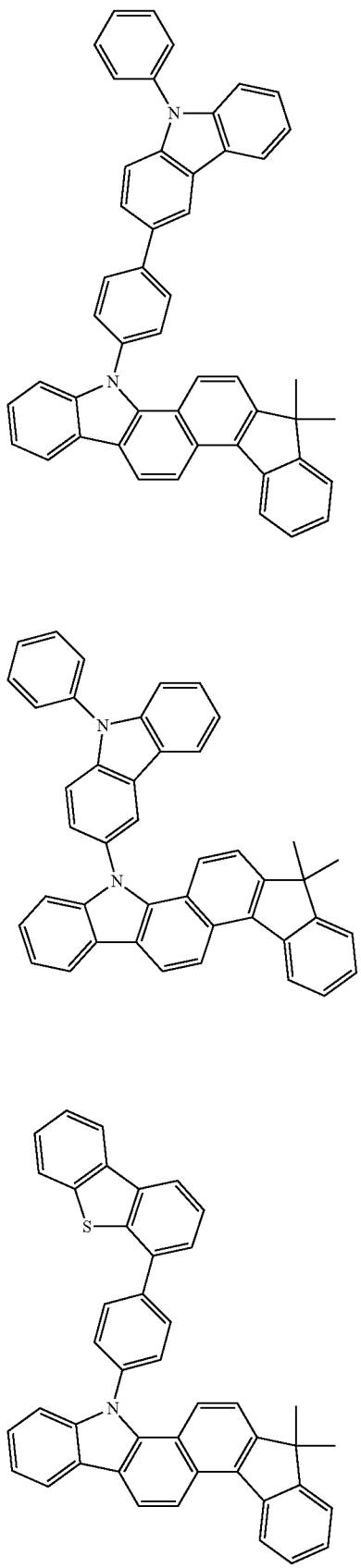
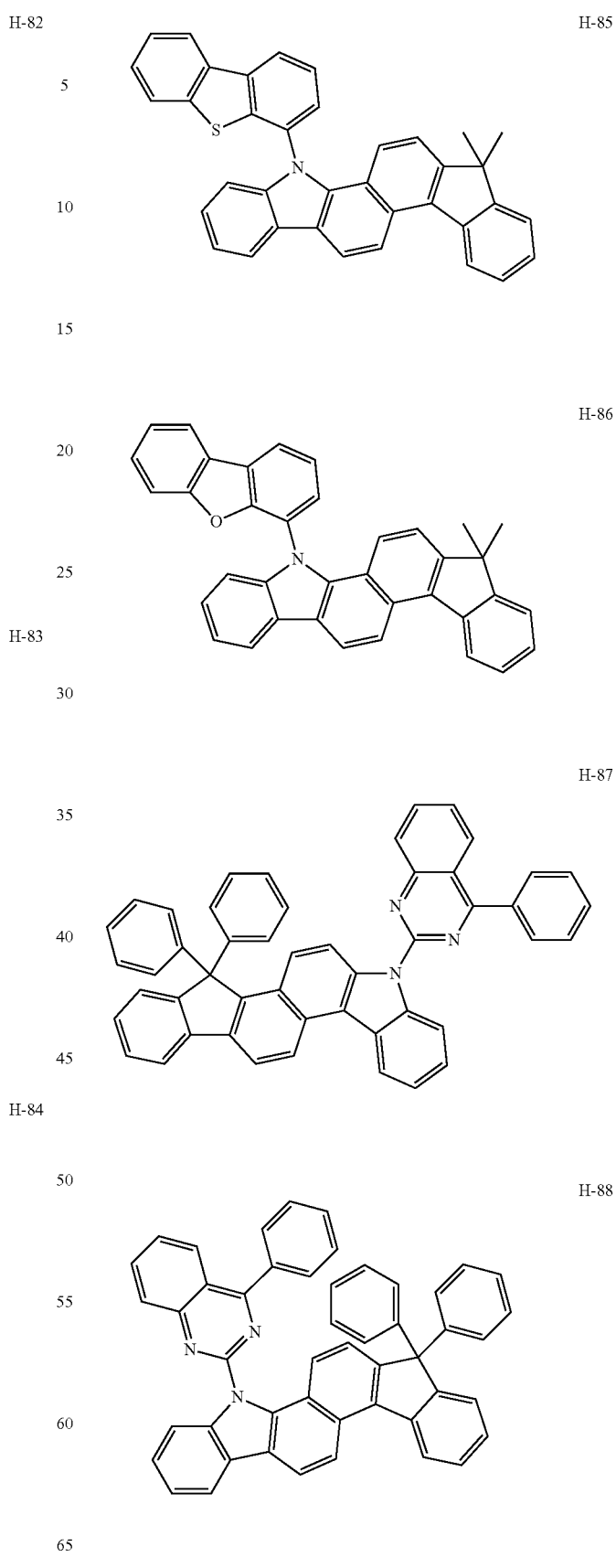

H-89
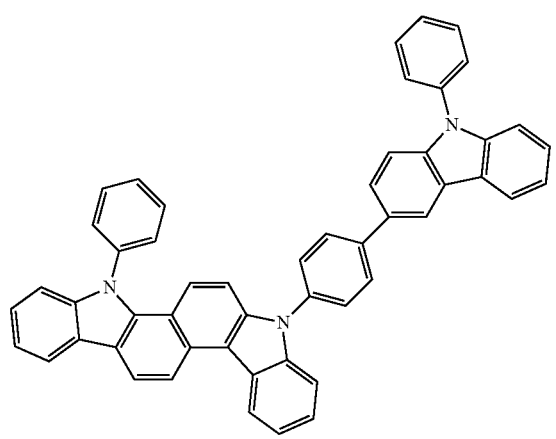
H-90
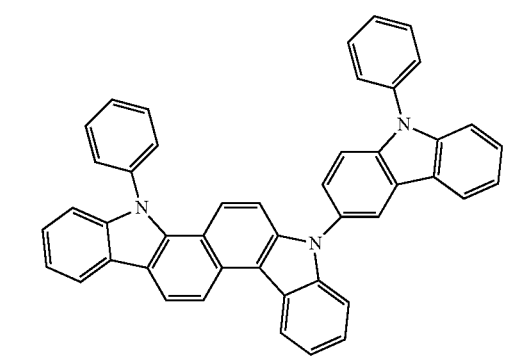
H-91
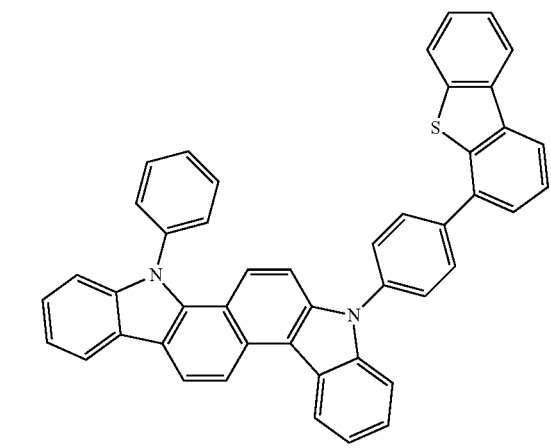
H-92
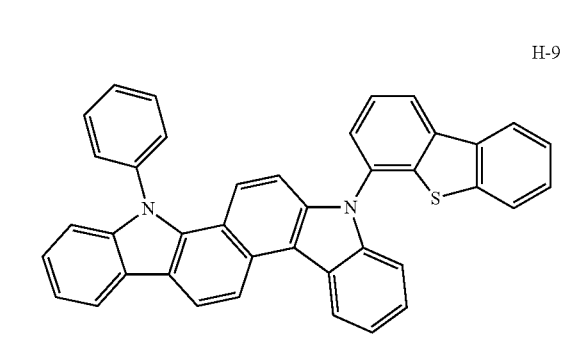
H-93
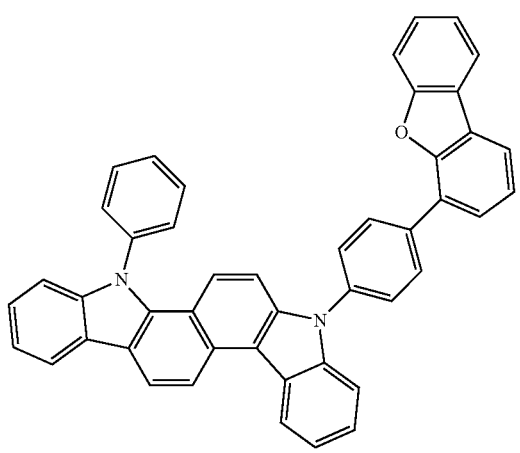
H-94
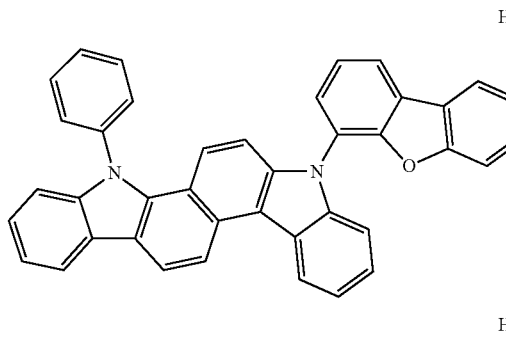
H-95
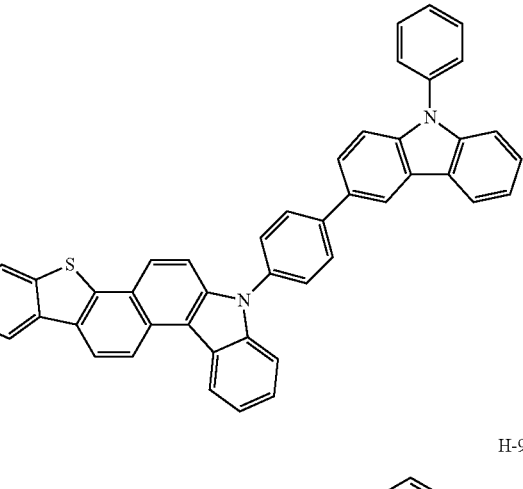
H-96
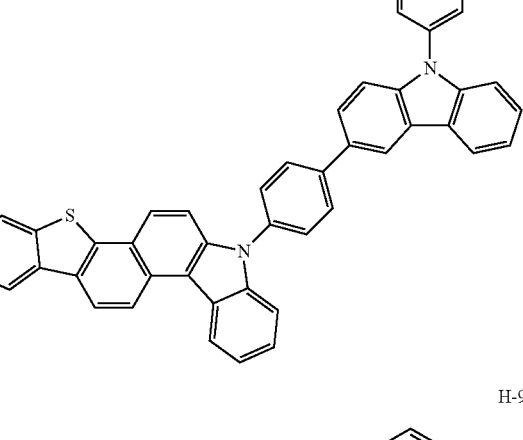

-continued
H-97
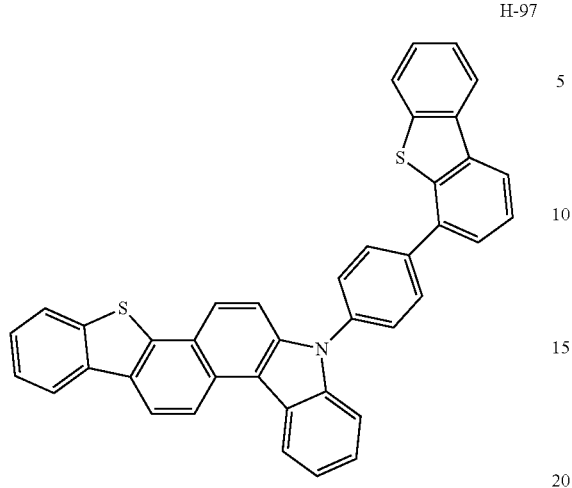
H-98
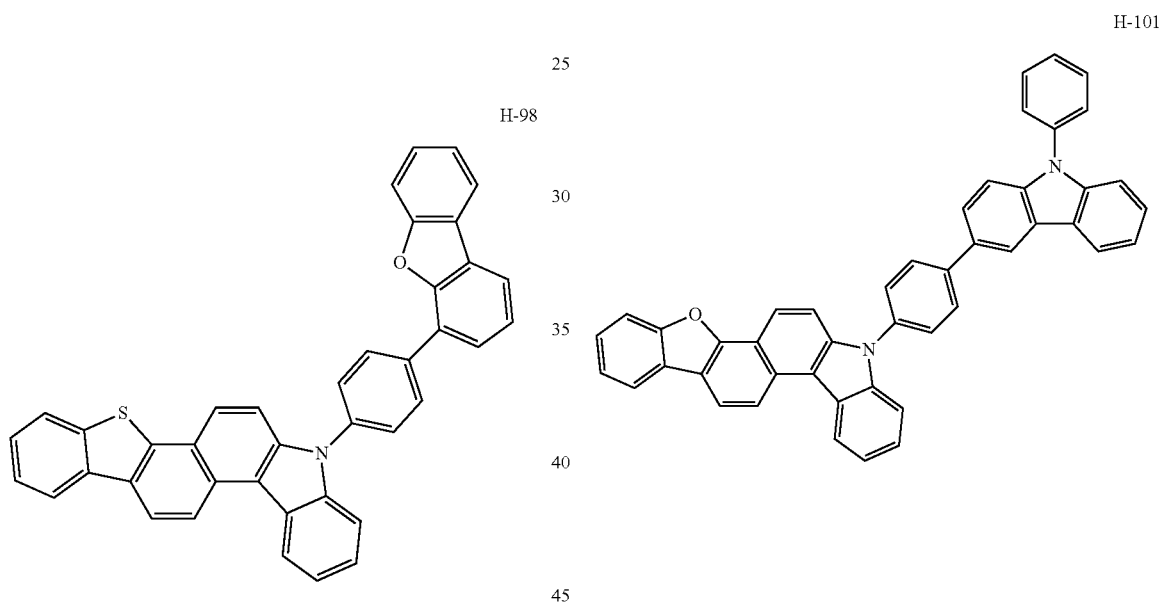
H-99
-continued
H-100
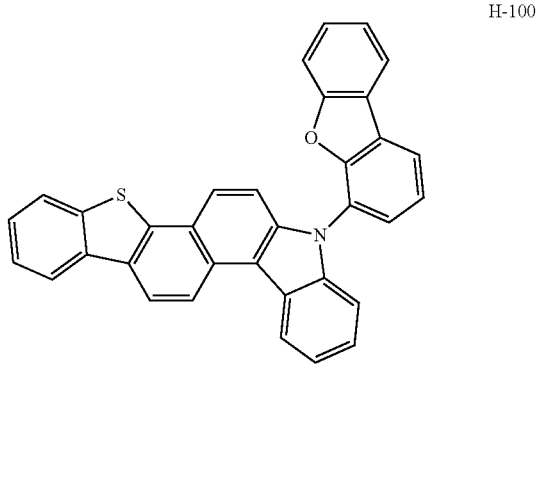
H-101
H-102
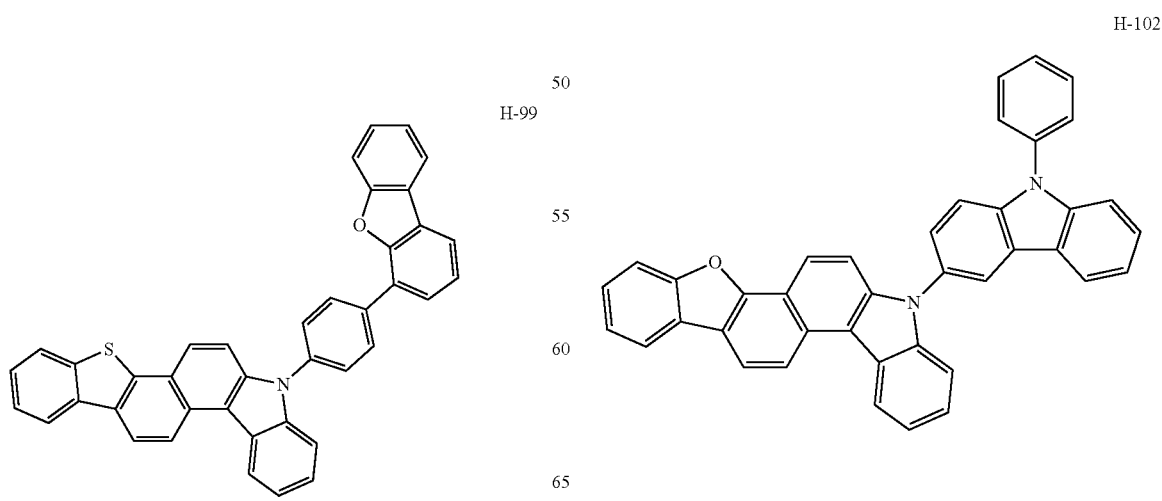

H-103
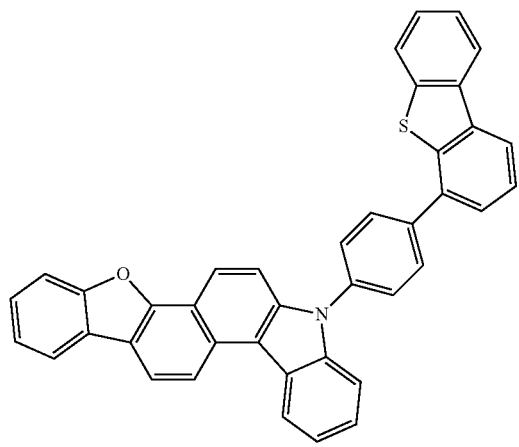
H-104
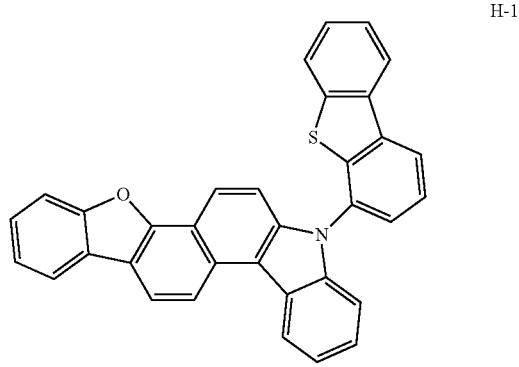
H-105
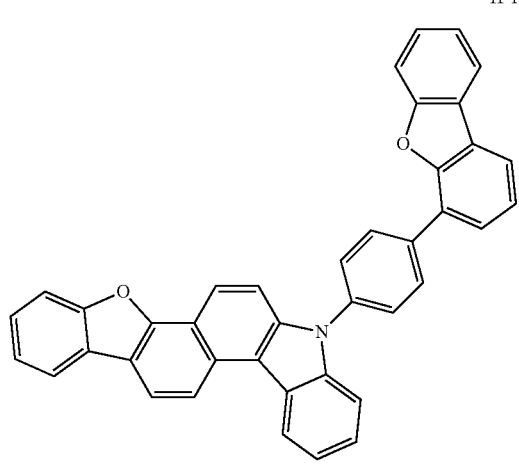
H-106
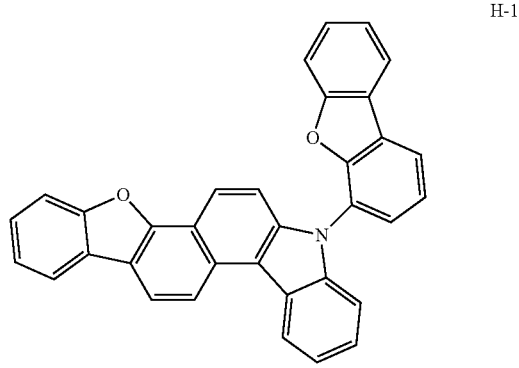
H-107
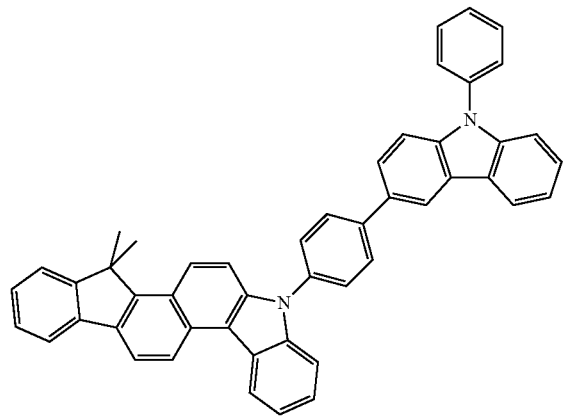
H-108
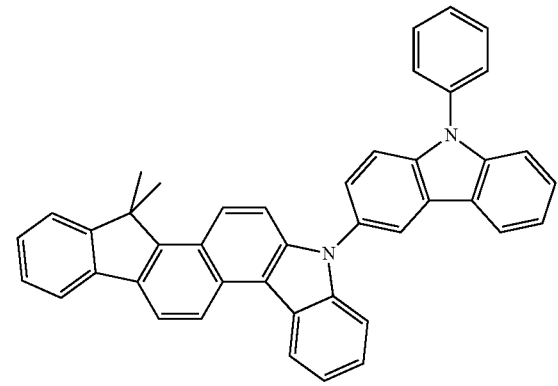
H-109
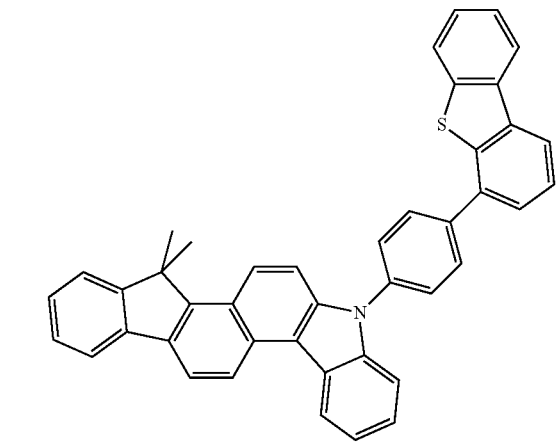

-continued
H-110
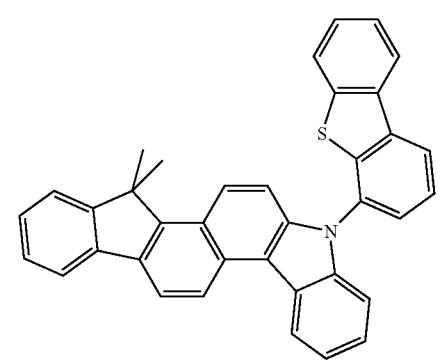
H-111
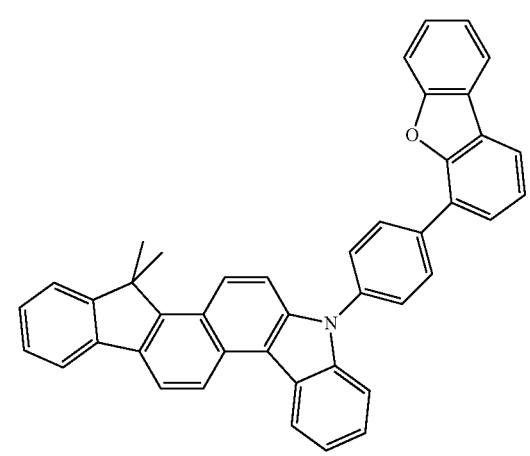
H-112
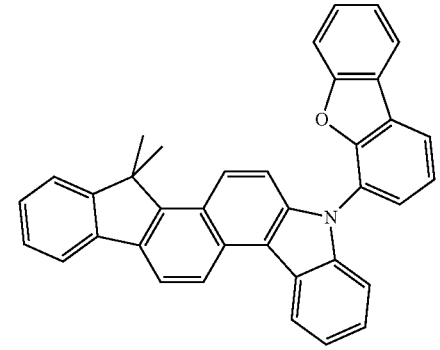
H-113
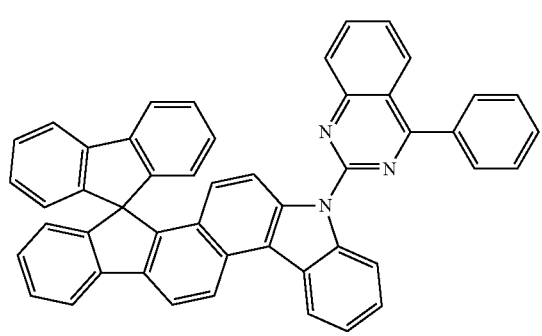
-continued
H-114
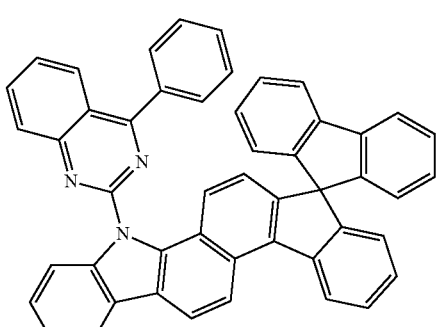
H-115
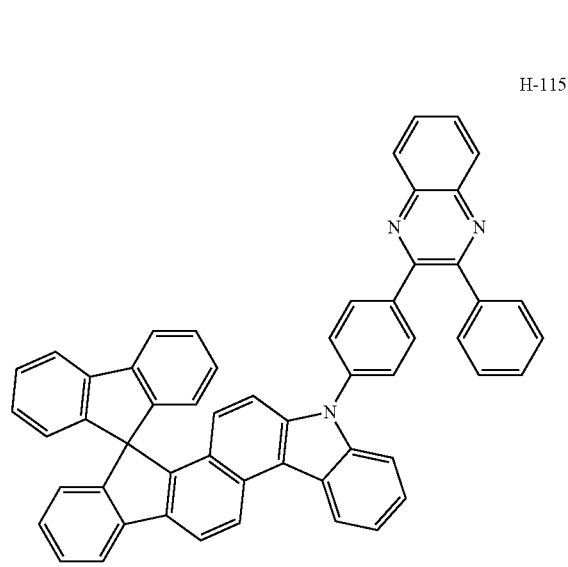
H-116
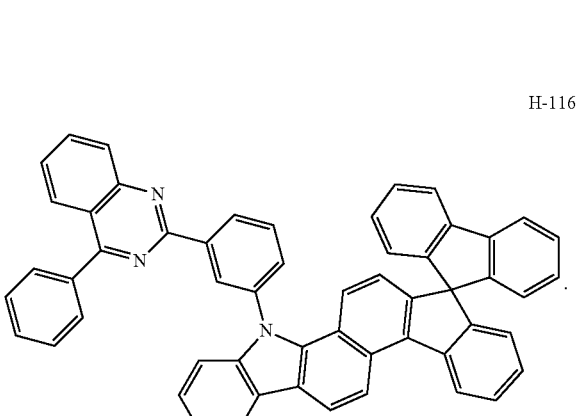
8. An organic electroluminescent device comprising the organic electroluminescent compound according to claim 1.
* * * * *